US008008255B2

(12) United States Patent
Ong et al.

(10) Patent No.: US 8,008,255 B2
(45) Date of Patent: *Aug. 30, 2011

(54) METHODS AND COMPOSITIONS FOR ENHANCED TRANSMUCOSAL DELIVERY OF PEPTIDES AND PROTEINS

(75) Inventors: John Ong, San Marcos, CA (US); Robert Jennings, San Diego, CA (US); Gregg Stetsko, San Diego, CA (US)

(73) Assignee: Amylin Pharmaceuticals, Inc., San Diego, CA (US)

( * ) Notice: Subject to any disclaimer, the term of this patent is extended or adjusted under 35 U.S.C. 154(b) by 1220 days.

This patent is subject to a terminal disclaimer.

(21) Appl. No.: 10/559,595

(22) PCT Filed: May 28, 2004

(86) PCT No.: PCT/US2004/017456
§ 371 (c)(1),
(2), (4) Date: Nov. 30, 2005

(87) PCT Pub. No.: WO2005/000222
PCT Pub. Date: Jan. 6, 2005

(65) Prior Publication Data
US 2006/0172001 A1    Aug. 3, 2006

Related U.S. Application Data

(60) Provisional application No. 60/474,233, filed on May 30, 2003.

(51) Int. Cl.
*A61K 38/00* (2006.01)
*A61K 38/22* (2006.01)
*A61K 38/26* (2006.01)
*C07K 14/00* (2006.01)
*C07K 14/575* (2006.01)
*C07K 14/605* (2006.01)

(52) U.S. Cl. .......... 514/11.7; 514/1.1; 514/1.2; 514/7.2; 530/300; 530/308; 530/324

(58) Field of Classification Search .................. None
See application file for complete search history.

(56) References Cited

U.S. PATENT DOCUMENTS

| | | | |
|---|---|---|---|
| 4,476,116 A | 10/1984 | Shabbir | |
| 4,847,240 A | 7/1989 | Ryser et al. | |
| 5,116,817 A | 5/1992 | Shabbir | |
| 5,124,314 A | 6/1992 | Cooper | |
| 5,330,761 A * | 7/1994 | Baichwal | 424/469 |
| 5,367,052 A | 11/1994 | Cooper et al. | |
| 5,424,286 A * | 6/1995 | Eng | 514/2 |
| 5,512,549 A | 4/1996 | Chen | |
| 5,554,388 A | 9/1996 | Illum | |
| 5,574,008 A | 11/1996 | Johnson et al. | |
| 5,580,953 A | 12/1996 | Albrecht et al. | |
| 5,686,411 A | 11/1997 | Gaeta et al. | |
| 5,705,483 A | 1/1998 | Galloway et al. | |
| 5,788,959 A | 8/1998 | Singh | |
| 5,804,212 A | 9/1998 | Illum | |
| 5,846,937 A * | 12/1998 | Drucker | 514/12 |
| 5,977,070 A | 11/1999 | Piazza et al. | |
| 5,981,488 A | 11/1999 | Hoffmann | |
| 6,294,153 B1 | 9/2001 | Modi | |
| 6,346,274 B1 | 2/2002 | Koll et al. | |
| 6,391,318 B1 | 5/2002 | Illum et al. | |
| 6,440,392 B1 | 8/2002 | Stern | |
| 6,528,486 B1 | 3/2003 | Larsen et al. | |
| 6,610,824 B2 | 8/2003 | Gaeta et al. | |
| 6,703,359 B1 * | 3/2004 | Young et al. | 514/2 |
| 6,767,887 B1 * | 7/2004 | Hoffmann et al. | 514/2 |
| 2002/0009491 A1 * | 1/2002 | Rothbard et al. | 424/484 |
| 2002/0137666 A1 * | 9/2002 | Beeley et al. | 514/2 |
| 2002/0141985 A1 | 10/2002 | Pittner et al. | |
| 2003/0087820 A1 | 5/2003 | Young et al. | |
| 2003/0087821 A1 * | 5/2003 | Beeley et al. | 514/12 |
| 2003/0220243 A1 | 11/2003 | Glaesner et al. | |
| 2004/0053819 A1 | 3/2004 | Dodd et al. | |
| 2005/0215475 A1 * | 9/2005 | Ong et al. | 514/12 |

FOREIGN PATENT DOCUMENTS

| | | |
|---|---|---|
| DE | 19921537 A1 * | 11/2000 |
| JP | 1998095738 A | 4/1998 |
| JP | 2000281589 A | 10/2000 |
| WO | WO 99/07404 A1 | 2/1999 |
| WO | WO 9907404 A1 * | 2/1999 |
| WO | WO 99/25727 A2 | 5/1999 |
| WO | WO 99/25728 A1 | 5/1999 |
| WO | WO 9940788 A1 * | 8/1999 |
| WO | WO 00/41546 A2 | 7/2000 |
| WO | WO 00/66629 A1 | 11/2000 |
| WO | WO 01/04156 A1 | 1/2001 |
| WO | WO 01/98331 A2 | 12/2001 |

(Continued)

OTHER PUBLICATIONS

NPL-PYY sequence from NCBI GenBank Accession No. P68005. Accessed Apr. 23, 2008.*
Walker, et al. , Pharmaceutical Research, 1999, vol. 16, pp. 1074-1080.
Callens, C., et al, "Evaluation of Starch-Maltodextrin-Carbopol 974 Mixtures for the Nasal Delivery of Insulin in Rabbits", J. Control Release, 2000, pp. 215-220, vol. 66(2-3).
Dyer, A.M., et al, "Nasal Delivery of Insulin Using Novel Chitosan Based Formulations: A Comparative Study . . . ", Pharm Res., 2002, pp. 998-1008, vol. 19(7).
Fernandez-Urrusuno, R., et al, "Enhancement of Nasal Absorption of Insulin Using Chitosan Nanoparticles", Pharm Res., Oct. 1999, pp. 1576-1581, vol. 16(10).

(Continued)

*Primary Examiner* — Julie Ha

(57) ABSTRACT

Provided are methods and compositions for enhancing the transmucosal absorption of bioactive peptides and proteins. More particularly, the invention provides compositions for enhancing the transmucosal absorption of bioactive peptides and proteins, such as exendin-4, PYY, $PYY_{3-36}$, and GLP-1 and their analogs and derivatives, wherein the compositions comprise an absorption enhancing mixture of a cationic polyamino acid and a buffer that is compatible with the polyamino acid. Also provided are methods for enhancing the transmucosal absorption and bioavailability of bioactive peptides and proteins using such compositions.

8 Claims, 2 Drawing Sheets

FOREIGN PATENT DOCUMENTS

| | | |
|---|---|---|
| WO | WO 02/47712 A2 | 6/2002 |
| WO | WO 02/48192 A2 | 6/2002 |
| WO | WO02/098348 | 12/2002 |
| WO | WO 03/026591 A2 | 4/2003 |

OTHER PUBLICATIONS

Illum, L., et al, "Chitosan as a Novel Nasal Delivery System for Peptide Drugs", Pharm Res., Aug. 1994, pp. 1186-1189, vol. 11(8).

Kyte, J., et al, "A Simple Method for Displaying the Hydropathic Character of a Protein", J Mol Biol., May 1982, pp. 105-132, vol. 157(1).

McEwan, G.T., et al, "Polycation-Induced Enhancement of Epithelial Paracellular Permeability . . . ", Biochem Biophys Acta., May 14, 1993, pp. 51-60, vol. 1148(1).

Miyamoto, M., et al, "Improved Nasal Absorption of Drugs Using Poly-L-Arginine: Effects of Concentration . . . ", Eur J Pharm Biopharm, Jul. 2001, pp. 21-30, vol. 52(1).

Miyamoto, M., et al, "Effect of Poly-L-Arginine on the Nasal Absorption . . . ", Int J Pharm., Sep. 11, 2001, pp. 127-138, vol. 226(1-2).

Natsume, H., et al, "Screening of Cationic Compound as an Absorption Enhancer . . . ", Int J Pharm., Aug. 5, 1999, pp. 1-12, vol. 185(1).

Ohtake, K., et al, "Analysis of Transient and Reversible Effects of Poly-L-Arginine on the In Vivo Nasal . . . ", J Control Release, Aug. 21, 2002, pp. 263-275, vol. 82(2-3).

Ohtake, K., et al, "Poly-L-Arginine Enhances Paracellular Permeability Via Serine/Threonine Phosphorylation . . . " Pharm Res., Nov. 2003, pp. 1838-1845, vol. 20(11).

Uchida, D.A., et al, "Cationic Proteins Increase the Permeability of Cultured Rabbit Tracheal Epithelial . . . " Exp Lung Res., Jan. 1996-Feb. 1996, pp. 85-99, vol. 22(1).

\* cited by examiner

METHODS AND COMPOSITIONS FOR ENHANCED TRANSMUCOSAL DELIVERY OF PEPTIDES AND PROTEINS

CROSS-REFERENCE TO RELATED APPLICATIONS

This application is a national stage filing of International Patent Application PCT/US2004/017456, filed May 28, 2004 which claims the benefit of U.S. Provisional Patent Application Ser. No. 60/474,233, filed May 30, 2003, each of which is incorporated herein by reference in its entirety for all purposes.

INCORPORATION-BY-REFERENCE OF MATERIAL SUBMITTED ON COMPACT DISCS

The sequence listing in the present application is being submitted on two compact discs labeled "Sequence Listing-Copy 1" and "Sequence Listing-Copy 2"; each containing a file of 142 KB in size named "0501_UTL_0.ST25.txt" created on Nov. 29, 2005, the contents of which are hereby incorporated by reference.

BACKGROUND

The administration of therapeutically active peptides and proteins has generally been limited to injection due to difficulties in achieving the required bioavailability via alternative, less invasive routes such as oral, transmucosal, or transdermal. For instance, administration by ingestion can result in chemical and enzymatic degradation in the gastrointestinal tract, resulting in a substantial loss of activity and low bioavailability. Transmucosal delivery through absorptive mucous membranes such as oral, buccal, sublingual, eye, nasal, pulmonary, rectal, and vaginal membranes, on the other hand, has the advantage of being noninvasive and of bypassing hepato/gastrointestinal clearance (at least initially). Peptides and proteins, however, are generally not well absorbed through mucosae because of their molecular size and hydrophilicity. In general, enzyme inhibitors and absorption enhancers need to be coadministered for successful transmucousal delivery of bioactive peptides and proteins.

Classes of absorption enhancers used for transmucosal delivery include bile salts and their derivatives, taurodihydrofusidates, mono- and polycarboxylic acids, cyclodextrins, surfactants (especially non-ionic), chelating agents, cationic polymers, lipids and phospholipids (see Davis and Illum, *Clin Pharmacokinet.*, 42:1107-1128, 2003 for a review). Each of these agents exerts its enhancing effects by a different mechanism, and many have been associated with various degrees of adverse effects. Nonetheless, these enhancers have been demonstrated to enhance the absorption and, consequently, bioavailability of peptides and proteins across the mucous membrane.

The nasal cavity provides an attractive route for peptide and protein delivery because of its relatively high permeability and ease of administration. Nasal spray compositions containing a chelating agent such as disodium ethylenediaminetetraacetate, or bile salt have been shown to enhance the absorption of nona- and deca-peptides having LHRH agonist or antagonist activity (U.S. Pat. Nos. 4,476,116 and 5,116, 817). A combination of bile salt and dimethyl-β-cyclodextrin has been used to enhance the nasal absorption of parathyroid hormones (U.S. Pat. No. 5,977,070). Lysophospholipids, acylcamitines and polyoxyethylene(20) sorbitan monooleate (Tween® 80) have also been used as enhancers for the delivery of insulin and calcitonin across mucous membranes (U.S. Pat. Nos. 5,804,212 and 6,440,392). The cationic polysaccharide chitosan, used as powder, nanoparticle, or in solution, has been demonstrated to enhance mucosal absorption of insulin, other peptides and proteins, and vaccines (U.S. Pat. No. 6,391,318; Dyer et al., *Pharm. Res.*, 19:998-1008, 2002; Illum et al., *Pharm. Res.*, 11:1186-1189, 1994; Fernandez-Urrusuno et al., *Pharm. Res.*, 16:1576-1581, 1999). Additionally, bioadhesive agents, such as carbomers and polycarbophil, have been used to increase the residence time and therefore the bioavailability of insulin from a powder dosage form (Callen and Remon, *Controlled Rel.*, 66:215-220, 2000).

The cationic polyamino acid, polylysine, was mentioned in an aerosol formulation for pulmonary and nasal delivery, but no rationale for its function was given (U.S. Pat. No. 6,294, 153). Another cationic polyamino acid, poly-L-arginine was reported to enhance the absorption of fluorescein isothiocyanate labeled dextran (Nasume et al., *Intl. J. Pharm.*, 185:1-12, 1999), but no bioactive peptides or proteins were investigated. Other applications for potential uses of cationic polyamino acids to improve transmucosal delivery of molecules can be found in U.S. Pat. Nos. 5,554,388 and 5,788, 959; Japanese Patent Applications 1998095738A, 2000281589A; McEwan et al., *Biochim. Biophys. Acta*, 1148: 51-60, 1993; Uchida et al., *Exp. Lung Res.*, 22:85-99, 1996; Natsume et al., *Drug Deliv. Systems*, 14:21-25, 1999; Miyamoto et al, *Intl. J. Pharma.*, 226:127-138, 2001; Miyamoto et al., *Eur. J. Pharma Biopharma.*, 52:21-30, 2001; Ohtake et al., *J. Controlled Res.*, 82:263-275, 2002 and Ohtake et al., *Pharm. Res.*, 20:1838-1845, 2003. Many of these papers describe the use of cationic polyamino acids to deliver marker molecules such a labeled dextran rather than proteins or peptides. Thus, there remains a need for improved absorption enhancers for use in the transmucosal delivery of bioactive peptides and proteins.

SUMMARY

Among the several aspects of the invention is provided a pharmaceutical composition for the transmucosal administration of a bioactive peptide or protein of interest comprising the bioactive peptide or protein of interest, an absorption enhancing amount of a cationic polyamino acid, and a compatible buffer that does not cause precipitation of the cationic polyamino acid and has a mono-anionic or neutral net charge at the pH of the composition. The composition is further characterized in that the transmucosal absorption of the bioactive protein or peptide of interest is increased relative to the absorption of the protein or peptide in the absence or substantial absence of the cationic polyamino acid. In one embodiment the absorption of the bioactive protein or peptide is increased at least 2-fold, while in other embodiments it is increased at least 5-fold or at least 10-fold. In one embodiment, the pH of the composition ranges from about pH 3.0 to about pH 6.0, while in another embodiment the pH is between about pH 4.0 and about pH 5.0. In still a further embodiment, the pH of the composition is about pH 4.5. In another embodiment, the compatible buffer comprises glutamic acid, while in other embodiments the compatible buffer comprises acetic acid or ε-aminocaproic acid. In a further embodiment, the cationic polyamino acid comprises poly-arginine, while in other embodiments the cationic polyamino acid is poly-histidine, poly-lysine or any combination of poly-arginine, poly-histidine and poly-lysine. In one embodiment the cationic polyamino acid or acids has an average molecular weight of between about 10 kDa and about 200 kDa. In another embodiment, the cationic polyamino acid has an average molecular weight of between about 100 kDa and 200 kDa. In still a further embodiment, the cationic polyamino acid has an average molecular weight between about 140 kDa and about 150 kDa, while in yet another embodiment, the cationic polyamino acid has an average molecular weight of about 141 kDa.

In other embodiments, the composition further comprises a tonicifying agent, a viscosity-increasing agent, a bioadhesive agent, a preservative or any combination of a tonicifying agent, a viscosity-increasing agent, a bioadhesive agent, and a preservative. In one embodiment the tonicifying agent used is selected from sodium chloride, mannitol, sucrose, glucose and any combination of sodium chloride, mannitol, sucrose and glucose. In another embodiment in which a viscosity-increasing agent is used, the agent can be selected from hydroxypropyl cellulose, hydroxyproply methylcellulose, methylcellulose with an average molecular weight between about 10 and about 1500 kDa, starch, gums and any combination of the listed viscosity increasing agents. In another embodiment, in which a bioadhesive agent is used, the bioadhesive agent can be selected from carbomer, polycarbophil and any combination of carbomer and polycarbophil. In embodiments utilizing a preservative, the preservative can be selected from phenylethyl alcohol, methylparaben, ethylparaben, propylparaben, butylparaben, chlorbutanol, benzoic acid, sorbic acid, phenol, m-cresol, alcohol, and any combination of the preservatives listed herein.

In certain embodiments, the bioactive protein or peptide is an exendin, an exendin analog or an exendin derivative described herein or known in the art including polymer-modified compounds thereof. In various embodiments the bioactive peptide or protein is exendin-3, exendin-4 or one of the analogs or derivatives described by any of Formulas I, II or III or listed in Table 1. In specific embodiments, the exendin analogs or derivatives include but are not limited to exendin-4 acid, exendin-4 (1-30), exendin-4 (1-30) amide, exendin-4 (1-28) amide, $^{14}$Leu, $^{25}$Phe exendin-4 amide, and $^{14}$Leu, $^{25}$Phe exendin-4 (1-28) amide.

In other embodiments, the bioactive protein or peptide is GLP-1 or any of the GLP-1 analogs and derivatives listed herein or known in the art including polymer-modified compounds thereof. In still another embodiment, the bioactive protein or peptide is a PYY peptide or an analog or a derivative of a PYY peptide listed herein or known in the art including polymer-modified compounds thereof. In yet another embodiment, the bioactive protein or peptide is amylin or an analog or a derivative of amylin listed herein or known in the art including polymer-modified compounds thereof.

One embodiment provides a pharmaceutical composition for transmucosal administration of a bioactive peptide or protein of interest comprising about 0.01% to about 5.0% (w/v) of the bioactive peptide or protein of interest, such as an exendin, a GLP-1, an amylin, or a PYY peptide as well and analogs of, derivatives of, and polymer-modified exendin, a GLP-1, amylin, and PYY; about 0.01% to about 1.0% (w/v) of a cationic polyamino acid having a molecular weight between about 10 kDa and about 200 kDa; such as poly-arginine, poly-histidine and poly-lysine; and about 0.01% to about 10.0% (w/v) of a compatible buffer, that at between about pH 4.0 and about 5.0 does not cause precipitation of the cationic polyamino acid, and has a mono-anionic or neutral net charge. Additionally, the transmucosal absorption of the bioactive peptide or protein is increased relative the absorption of said bioactive peptide or protein in the absence of said cationic polyamino acid.

In a particular embodiment is provided a pharmaceutical composition for transmucosal administration comprising about 0.5% (w/v) of exendin-4; about 0.5% (w/v) of poly-L-arginine hydrochloride having an average molecular weight of about 141 kDa; about 0.72% (w/v) sodium chloride; and about 0.56% monosodium glutamate, monohydrate (w/v) at a pH of about 4.5.

In another particular embodiment is provided a pharmaceutical composition for transmucosal administration comprising about 0.5% (w/v) of exendin-4; about 1.0% (w/v) of poly-L-arginine hydrochloride having an average molecular weight of about 141 kDa; about 0.72% (w/v) sodium chloride; and about 0.56% monosodium glutamate, monohydrate (w/v) at a pH of about 4.5.

Further embodiments provide a method for transmucosal administration of a bioactive peptide or protein comprising contacting a mucosal surface with any of the pharmaceutical compositions described herein for a time sufficient for a therapeutically effective amount of the bioactive peptide or protein of interest to cross the mucosa such that the transmucosal absorption of the bioactive protein or peptide is increased relative to the absorption of the bioactive protein or peptide in the absence or substantial absence of a cationic polyamino acid, such as in the compositions described herein. In one embodiment, the bioactive peptide or protein is an exendin, an exendin analog, or an exendin derivative described herein or known in the art including polymer-modified compounds thereof. In another embodiment, the bioactive peptide or protein is GLP-1, a GLP-1 analog or a GLP-1 derivative described herein or known in the art including polymer-modified compounds thereof. In still another embodiment, the bioactive peptide or protein is a PYY peptide, a PYY peptide analog, or a PYY peptide derivative described herein or known in the art including polymer-modified compounds thereof. In yet another embodiment, the bioactive peptide or protein is amylin, an amylin analog, or an amylin derivative described herein or known in the art including polymer-modified compounds thereof.

Also provided are methods for increasing the bioavailability of a bioactive protein or peptide of interest comprising administering to a subject any of the pharmaceutical compositions described herein for a time sufficient to allow transmucosal absorption of the protein or peptide such that the bioavailability of the bioactive peptide or protein of interest is greater than when the peptide or protein is administered alone, that is in the absence or substantial absence of the cationic polyamino acid. In one embodiment, the method is used to increase the bioavailability of an exendin, an exendin analog, or an exendin derivative described herein or known in the art including polymer-modified compounds thereof. In another embodiment, the method is used to increase the bioavailability of GLP-1, a GLP-1 analog, or a GLP-1 derivative described herein or known in the art, including polymer modified compounds thereof. In yet another embodiment, the method is used to increase the bioavailability of a PYY peptide, a PYY analog, or a PYY derivative described herein or known in the art including polymer-modified compounds thereof. In still another embodiment, the method is used to increase the bioavailability of amylin, an amylin analog, or an amylin derivative described herein or known in the art including polymer-modified compounds thereof.

DETAILED DESCRIPTION

Figure 1:
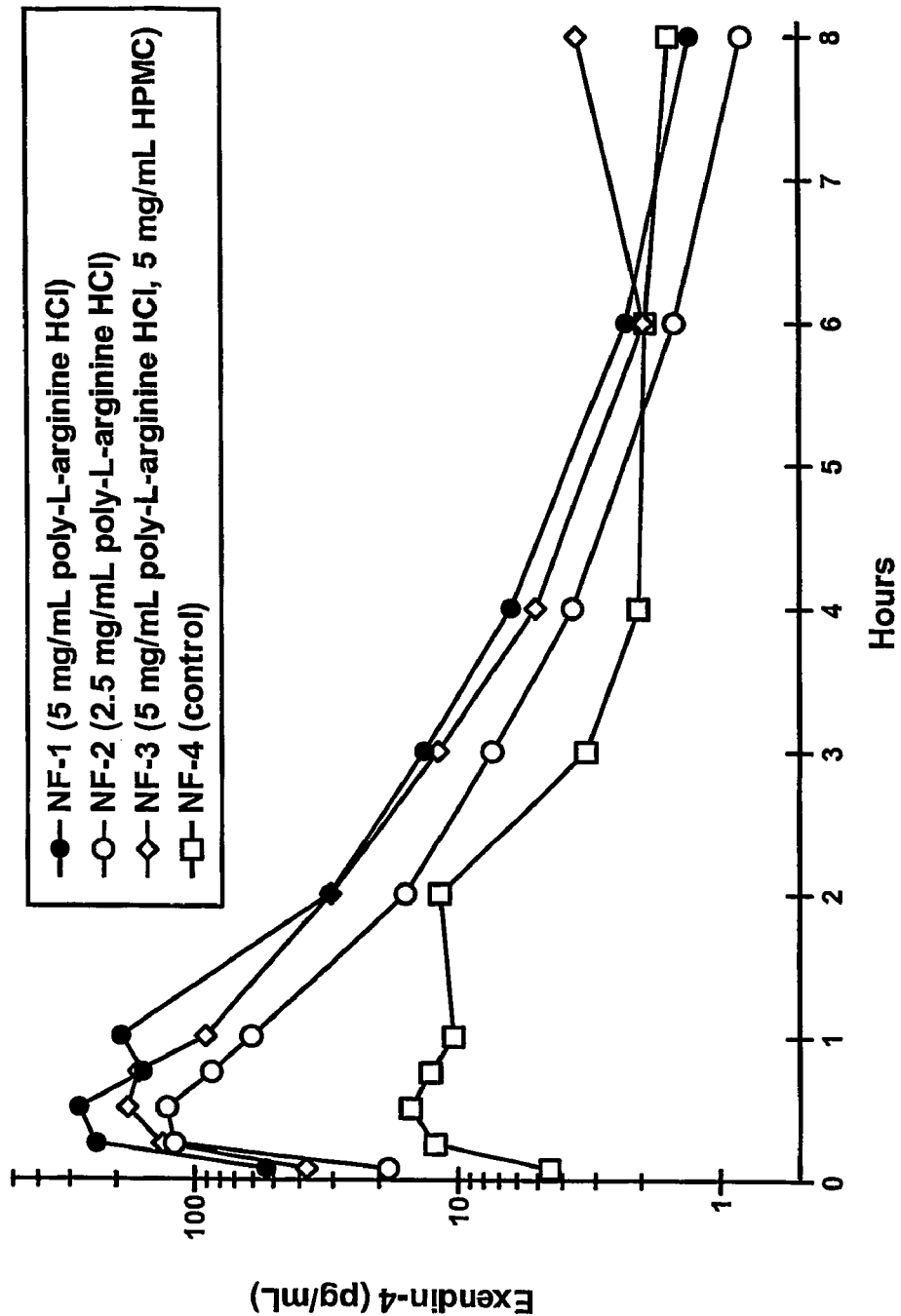
FIG. 1 depicts the bioavailability enhancement of three exendin-4 aqueous solutions containing poly-L-arginine with or without hydroxypropyl methylcellulose as compared to a control exendin-4 solution without poly-L-arginine. Shown are the pharmacokinetic profiles of exendin-4 in Cynomolgus monkeys (n=3) after intranasal doses normalized to 1 μg/kg.

In one aspect, the present invention teaches the design of novel pharmaceutical compositions for the transmucosal delivery of bioactive peptides and proteins. The novel compositions of the invention may be used to effectively deliver bioactive peptides and proteins systemically to the blood subsequent to transmucosal administration.

More particularly, it has now been found that enhanced transmucosal absorption of bioactive peptides and proteins can be achieved when delivered in conjunction with an absorption enhancing composition comprising a cationic polyamino acid and a buffer which is compatible with the cationic polyamino acid.

Generally, peptides and proteins comprise hydrophobic, hydrophilic, and charged regions which are all capable of interaction with other molecules. As such, one of skill in the art may expect that cationic compounds, such as cationic polyamino acids, would interact with the negative charges of the peptides or proteins. Based on precipitation encountered when cationic polyamino acids are formulated with multi-anionic buffers, such interactions may be expected to result in precipitation or inactivity of the cationic polyamino acid as a permeation enhancer. However, it was unexpectedly discovered according to the invention that cationic polyamino acids, particularly when formulated with buffers that avoid interaction and/or precipitation of the polyamino acids with bioactive peptides or proteins, actually act as a transmucosal absorption enhancer. Increases in absorption can be at least 2-fold, at least 5-fold or at least 10 fold greater than that obtained in the absence or substantial absence of the cationic polyamino acid. The extent of the enhanced absorption exceeds what would be normally expected with traditional cationic absorption enhancers such as chitosan. Further, this enhanced transmucosal absorption results in an unexpected improvement in bioavailability of greater than 2-fold, greater than 5-fold or greater than 10-fold compared to transmucosal delivery in the absence or substantial absence of the absorption enhancing compositions described herein. It will be apparent to those skilled in the art that the exact increase in absorption or bioavailability may vary with known factors such as the size of the protein, the method of administration, the concentration of the bioactive protein or peptide, the amount of composition applied, and the particular mucosal surface to which the composition is applied.

Other aspects relate to methods for enhancing the transmucosal absorption of bioactive peptides and proteins, and methods for improving the bioavailability of bioactive peptides and proteins when administered via transmucosal delivery. The pharmaceutical compositions can be delivered to the mucous membrane absorption site by any means known in the art, for example, dropping or spraying from a bottle into the eye, nasal, buccal, or sublingual cavity; by aerosolizing from an inhaler into the pulmonary region; as well as by applying a tablet, capsule, permeable/soluble matrix, or other known dosage forms to the buccal, sublingual, rectal, or vaginal areas.

The pharmaceutical compositions described herein that provide enhanced transmucosal absorption generally comprise a bioactive peptide or protein in combination with an absorption enhancing mixture comprising a cationic polyamino acid and a buffer that is compatible with the cationic polyamino acid. Optionally, the pharmaceutical compositions of the invention may also include one or more excipients such as agent(s) to render the solution compatible with body tissue; viscosity-increasing agent(s), bioadhesive agents, preservative(s), and the like.

The bioactive peptides or proteins of the invention include peptides or proteins that are inherently compatible or formulated to be compatible with the cationic polyamino acids of the invention, i.e., those bioactive peptides and proteins which do not interact with or cause precipitation of the cationic polyamino acid when in solution. In one embodiment the peptide or protein has the same net charge as the polyamino acid at the pH of the composition. For example, at the pH of the composition both the protein and the polyamino acid have a net positive charge. In this situation, it is not necessary that the magnitude of the charge be identical, but only that the net charge be the same.

The bioactive peptides or proteins used in the composition can be any bioactive protein or peptide known in the art. In one embodiment the bioactive peptides and proteins comprise exendins, exendin analogs and exendin derivatives. Examples of suitable exendins include exendin-3, exendin-4, exendin-4 acid, exendin-4 (1-30), exendin-4 (1-30) amide, exendin-4 (1-28), exendin-4 (1-28) amide, $^{14}$Leu, $^{25}$Phe exendin-4 amide, and $^{14}$Leu, $^{25}$Phe exendin-4 (1-28) amide as well as other bioactive exendins known in the art such as those described in International Patent Application Publication Nos. WO 99/07404, WO 99/25727, WO 99/25728, and WO 01/04156; US Patent Application Publication Nos. US 2003-0087820, US 2002-137666 and US 2003-087821; and U.S. Pat. No. 6,528,486, all of which are herein incorporated by reference in their entireties and in particular the exendin-related sequences contained therein.

Exendins that can be used in the compositions disclosed herein include those described by Formula I (SEQ ID No. 3) which is as follows:

$Xaa_1$ $Xaa_2$ $Xaa_3$ Gly Thr $Xaa_6$ $Xaa_7$ $Xaa_8$ $Xaa_9$ $Xaa_{10}$ Ser Lys Gln $Xaa_{14}$ Glu Glu Glu Ala Val Arg Leu $Xaa_{22}$ $Xaa_{23}$ $Xaa_{24}$ $Xaa_{25}$ Leu Lys Asn Gly Gly $Xaa_{31}$ Ser Ser Gly Ala $Xaa_{36}$ $Xaa_{37}$ $Xaa_{38}$ $Xaa_{39}$-Z;

where:
  $Xaa_1$ is His, Arg or Tyr;
  $Xaa_2$ is Ser, Gly, Ala or Thr;
  $Xaa_3$ is Asp or Glu;
  $Xaa_6$ is Phe, Tyr or naphthylalanine;
  $Xaa_7$ is Thr or Ser;
  $Xaa_8$ is Ser or Thr;
  $Xaa_9$ is Asp or Glu;
  $Xaa_{10}$ is Leu, Ile, Val, pentylglycine or Met;
  $Xaa_{14}$ is Leu, Ile, pentylglycine, Val or Met;
  $Xaa_{22}$ is Phe, Tyr or naphthylalanine;
  $Xaa_{23}$ is Ile, Val, Leu, pentylglycine, tert-butylglycine or Met;
  $Xaa_{24}$ is Glu or Asp;
  $Xaa_{25}$ is Trp, Phe, Tyr, or naphthylalanine;
  $Xaa_{31}$, $Xaa_{36}$, $Xaa_{37}$ and $Xaa_{38}$ are independently Pro, homoproline, 3Hyp, 4Hyp, thioproline, N— alkylglycine, N-alkylpentylglycine or N-alkylalanine;
  $Xaa_{39}$ is Ser, Thr or Tyr; and
  Z is —OH or —NH2

Examples of additional exendins that can be used in the compositions disclosed herein include those described by Formula II (SEQ ID No. 4) which is as follows:

Xaa$_1$ Xaa$_2$ Xaa$_3$ Gly Xaa$_5$ Xaa$_6$ Xaa$_7$ Xaa$_8$ Xaa$_9$ Xaa$_{10}$ Xaa$_{11}$ Xaa$_{12}$ Xaa$_{13}$ Xaa$_{14}$ Xaa$_{15}$ Xaa$_{16}$ Xaa$_{17}$ Ala Xaa$_{19}$ Xaa$_{20}$ Xaa$_{21}$ Xaa$_{22}$ Xaa$_{23}$ Xaa$_{24}$ Xaa$_{25}$ Xaa$_{26}$ Xaa$_{27}$ Xaa$_{28}$-Z$_1$;

where

Xaa$_1$ is His, Arg or Tyr;
Xaa$_2$ is Ser, Gly, Ala or Thr;
Xaa$_3$ is Ala, Asp or Glu;
Xaa$_5$ is Ala or Thr;
Xaa$_6$ is Ala, Phe, Tyr or naphthylalanine;
Xaa$_7$ is Thr or Ser;
Xaa$_8$ is Ala, Ser or Thr;
Xaa$_9$ is Asp or Glu;
Xaa$_{10}$ is Ala, Leu, Ile, Val, pentylglycine or Met;
Xaa$_{11}$ is Ala or Ser;
Xaa$_{12}$ is Ala or Lys;
Xaa$_{13}$ is Ala or Gln;
Xaa$_{14}$ is Ala, Leu, Ile, pentylglycine, Val or Met;
Xaa$_{15}$ is Ala or Glu;
Xaa$_{16}$ is Ala or Glu;
Xaa$_{17}$ is Ala or Glu;
Xaa$_{19}$ is Ala or Val;
Xaa$_{20}$ is Ala or Arg;
Xaa$_{21}$ is Ala or Leu;
Xaa$_{22}$ is Ala, Phe, Tyr or naphthylalanine;
Xaa$_{23}$ is Ile, Val, Leu, pentylglycine, tert-butylglycine or Met;
Xaa$_{24}$ is Ala, Glu or Asp;
Xaa$_{25}$ is Ala, Trp, Phe, Tyr or naphthylalanine;
Xaa$_{26}$ is Ala or Leu;
Xaa$_{27}$ is Ala or Lys;
Xaa$_{28}$ is Ala or Asn;
Z$_1$ is —OH,
—NH$_2$,
Gly-Z$_2$,
Gly Gly-Z$_2$,
Gly Gly Xaa$_{31}$-Z$_2$,
Gly Gly Xaa$_{31}$ Ser-Z$_2$,
Gly Gly Xaa$_{31}$ Ser Ser-Z$_2$,
Gly Gly Xaa$_{31}$ Ser Ser Gly-Z$_2$,
Gly Gly Xaa$_{31}$ Ser Ser Gly Ala-Z$_2$,
Gly Gly Xaa$_{31}$ Ser Ser Gly Ala Xaa$_{36}$-Z$_2$,
Gly Gly Xaa$_{31}$ Ser Ser Gly Ala Xaa$_{36}$ Xaa$_{37}$-Z$_2$, or
Gly Gly Xaa$_{31}$ Ser Ser Gly Ala Xaa$_{36}$ Xaa$_{37}$ Xaa$_{38}$-Z$_2$;
Xaa$_{31}$ Xaa$_{36}$, Xaa$_{37}$ and Xaa$_{38}$ are independently Pro, homoproline, 3Hyp, 4Hyp, thioproline, N-alkylglycine, N-alkylpentylglycine or N-alkylalanine; and
Z$_2$ is —OH or —NH$_2$;
provided that no more than three of Xaa$_3$, Xaa$_5$, Xaa$_6$, Xaa$_8$, Xaa$_{10}$, Xaa$_{11}$, Xaa$_{12}$, Xaa$_{13}$, Xaa$_{14}$, Xaa$_{15}$, Xaa$_{16}$, Xaa$_{17}$, Xaa$_{19}$, Xaa$_{20}$, Xaa$_{21}$, Xaa$_{24}$, Xaa$_{25}$, Xaa$_{26}$, Xaa$_{27}$ and Xaa$_{28}$ are Ala Additional examples of exendins that are suitable for use in the compositions disclosed herein are those described by Formula III (SEQ ID No. 5) which is as follows:

Xaa$_1$ Xaa$_2$ Xaa$_3$ Xaa$_4$ Xaa$_5$ Xaa$_6$ Xaa$_7$ Xaa$_8$ Xaa$_9$ Xaa$_{10}$ Xaa$_{11}$ Xaa$_{12}$ Xaa$_{13}$ Xaa$_{14}$ Xaa$_{15}$ Xaa$_{16}$ Xaa$_{17}$ Ala Xaa$_{19}$ Xaa$_{20}$ Xaa$_{21}$ Xaa$_{22}$ Xaa$_{23}$ Xaa$_{24}$ Xaa$_{25}$ Xaa$_{26}$ Xaa$_{27}$ Xaa$_{28}$-Z$_1$;

wherein

Xaa$_1$ is His, Arg, Tyr, Ala, Norval, Val or Norleu;
Xaa$_2$ is Ser, Gly, Ala or Thr;
Xaa$_3$ is Ala, Asp or Glu;
Xaa$_4$ is Ala, Norval, Val, Norleu or Gly;
Xaa$_5$ is Ala or Thr;
Xaa$_6$ is Ala, Phe, Tyr or naphthylalanine;
Xaa$_7$ is Thr or Ser;
Xaa$_8$ is Ala, Ser or Thr;
Xaa$_9$ is Ala, Norval, Val, Norleu, Asp or Glu;
Xaa$_{10}$ is Ala, Leu, Ile, Val, pentylglycine or Met;
Xaa$_{11}$ is Ala or Ser;
Xaa$_{12}$ is Ala or Lys;
Xaa$_{13}$ is Ala or Gln;
Xaa$_{14}$ is Ala, Leu, Ile, pentylglycine, Val or Met;
Xaa$_{15}$ is Ala or Glu;
Xaa$_{16}$ is Ala or Glu;
Xaa$_{17}$ is Ala or Glu;
Xaa$_{19}$ is Ala or Val;
Xaa$_{20}$ is Ala or Arg;
Xaa$_{21}$ is Ala or Leu;
Xaa$_{22}$ is Phe, Tyr or naphthylalanine;
Xaa$_{23}$ is Ile, Val, Leu, pentylglycine, tert-butylglycine or Met;
Xaa$_{24}$ is Ala, Glu or Asp;
Xaa$_{25}$ is Ala, Trp, Phe, Tyr or naphthylalanine;
Xaa$_{26}$ is Ala or Leu;
Xaa$_{27}$ is Ala or Lys;
Xaa$_{28}$ is Ala or Asn;
Z$_1$ is —OH,
—NH$_2$,
Gly-Z$_2$,
Gly Gly-Z$_2$,
Gly Gly Xaa$_{31}$-Z$_2$,
Gly Gly Xaa$_{31}$ Ser-Z$_2$,
Gly Gly Xaa$_{31}$ Ser Ser-Z$_2$,
Gly Gly Xaa$_{31}$ Ser Ser Gly-Z$_2$,
Gly Gly Xaa$_{31}$ Ser Ser Gly Ala-Z$_2$,
Gly Gly Xaa$_{31}$ Ser Ser Gly Ala Xaa$_{36}$-Z$_2$,
Gly Gly Xaa$_{31}$ Ser Ser Gly Ala Xaa$_{36}$ Xaa$_{37}$-Z$_2$,
Gly Gly Xaa$_{31}$ Ser Ser Gly Ala Xaa$_{36}$ Xaa$_{37}$ Xaa$_{38}$-Z$_2$,
or Gly Gly Xaa$_{31}$ Ser Ser Gly Ala Xaa$_{36}$ Xaa$_{37}$ Xaa$_{38}$ Xaa$_{39}$-Z$_2$;

where:

Xaa$_{31}$, Xaa$_{36}$, Xaa$_{37}$ and Xaa$_{38}$ are independently Pro, homoproline, 3Hyp, 4Hyp, thioproline, N-alkylglycine, N-alkylpentylglycine or N-alkylalanine;
Xaa$_{39}$ is Ser, Thr or Tyr; and
Z$_2$ is —OH or —NH$_2$;
provided that no more than three of Xaa$_3$, Xaa$_4$, Xaa$_5$, Xaa$_6$, Xaa$_8$, Xaa$_9$, Xaa$_{10}$, Xaa$_{11}$, Xaa$_{12}$, Xaa$_{13}$, Xaa$_{14}$, Xaa$_{15}$, Xaa$_{16}$, Xaa$_{17}$, Xaa$_{19}$, Xaa$_{20}$, Xaa$_{21}$, Xaa$_{24}$, Xaa$_{25}$, Xaa$_{26}$, Xaa$_{27}$ and Xaa$_{28}$ are Ala;
and provided also that, if Xaa$_1$ is His, Arg or Tyr, then at least one of Xaa$_3$, Xaa$_4$ and Xaa$_9$ is Ala.

Examples of particular exendins, exendin analogs and exendin derivatives that can be used in the compositions described herein, include, but are not limited to those described in Table 1. In one embodiment, the bioactive peptide or protein is exendin-4.

TABLE 1

Exendins, Exendin Analogs and Exendin Derivatives

| SEQ ID NO | Sequence |
|---|---|
| 1 | His Ser Asp Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro Ser |
| 2 | His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro Ser |
| 6 | His Gly Glu Gly Thr Phe Thr Ser Asp Leu Ser Lys Gln Met Glu Glu Glu Ala Val Arg Leu Phe Ile Glu Trp Leu Lys Asn Gly Gly |
| 7 | His Gly Glu Gly Thr Phe Thr Ser Asp Leu Ser Lys Gln Met Glu Glu Glu Ala Val Arg Leu Phe Ile Glu Trp Leu Lys Asn Gly Gly-NH$_2$ |
| 8 | His Gly Glu Gly Thr Phe Thr Ser Asp Leu Ser Lys Gln Leu Glu Glu Glu Ala Val Arg Leu Ala Ile Glu Phe Leu Lys Asn-NH$_2$ |
| 9 | His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly Ala Pro Pro Pro Ser-NH$_2$ |
| 10 | His Gly Glu Gly Thr Phe Thr Ser Asp Leu Ser Lys Gln Leu Glu Glu Glu Ala Val Arg Leu Phe Ile Glu Trp Leu Lys Asn Gly Gly Pro Ser Ser Gly Ala Pro Pro Pro Ser NH$_2$ |
| 11 | His Gly Glu Gly Thr Phe Thr Ser Asp Leu Ser Lys Gln Met Glu Glu Glu Ala Val Arg Leu Phe Ile Glu Phe Leu Lys Asn Gly Gly Pro Ser Ser Gly Ala Pro Pro Pro Ser NH$_2$ |
| 12 | Tyr Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro Ser NH$_2$ |
| 13 | His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro Tyr NH$_2$ |
| 14 | His Gly Asp Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro Ser NH$_2$ |
| 15 | His Gly Glu Gly Thr napthylAla Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro Ser NH$_2$ |
| 16 | His Gly Glu Gly Thr Phe Ser Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro Ser NH$_2$ |
| 17 | His Gly Glu Gly Thr Phe Ser Thr Asp Leu Ser Lys Gln Met Glu Glu Glu Ala Val Arg Leu Phe Ile Glu Trp Leu Lys Asn Gly Gly Pro Ser Ser Gly Ala Pro Pro Pro Ser NH$_2$ |
| 18 | His Gly Glu Gly Thr Phe Thr Thr Asp Leu Ser Lys Gln Met Glu Glu Glu Ala Val Arg Leu Phe Ile Glu Trp Leu Lys Asn Gly Gly Pro Ser Ser Gly Ala Pro Pro Pro Ser NH$_2$ |
| 19 | His Gly Glu Gly Thr Phe Thr Ser Glu Leu Ser Lys Gln Met Glu Glu Glu Ala Val Arg Leu Phe Ile Glu Trp Leu Lys Asn Gly Gly Pro Ser Ser Gly Ala Pro Pro Pro Ser NH$_2$ |
| 20 | His Gly Glu Gly Thr Phe Thr Ser Asp pentylGly Ser Lys Gln Met Glu Glu Glu Ala Val Arg Leu Phe Ile Glu Trp Leu Lys Asn Gly Gly Pro Ser Ser Gly Ala Pro Pro Pro Ser NH$_2$ |
| 21 | His Gly Glu Gly Thr Phe Thr Ser Asp pentylGly Ser Lys Gln Leu Glu Glu Glu Ala Val Arg Leu Phe Ile Glu Phe Leu Lys Asn Gly Gly Pro Ser Ser Gly Ala Pro Pro Pro Ser NH$_2$ |
| 22 | His Gly Glu Gly Thr Phe Thr Ser Asp Leu Ser Lys Gln pentylGly Glu Glu Glu Ala Val Arg Leu Phe Ile Glu Trp Leu Lys Asn Gly Gly Pro Ser Ser Gly Ala Pro Pro Pro Ser NH$_2$ |
| 23 | His Gly Glu Gly Thr Phe Thr Ser Asp Leu Ser Lys Gln pentylGly Glu Glu Glu Ala Val Arg Leu Phe Ile Glu Phe Leu Lys Asn Gly Gly Pro Ser Ser Gly Ala Pro Pro Pro Ser NH$_2$ |
| 24 | His Gly Glu Gly Thr Phe Thr Ser Asp Leu Ser Lys Gln Met Glu Glu Glu Ala Val Arg Leu napthylAla Ile Glu Trp Leu Lys Asn Gly Gly Pro Ser Ser Gly Ala Pro Pro Pro Ser NH$_2$ |
| 25 | His Gly Glu Gly Thr Phe Thr Ser Asp Leu Ser Lys Gln Met Glu Glu Glu Ala Val Arg Leu Phe Val Glu Trp Leu Lys Asn Gly Gly Pro Ser Ser Gly Ala Pro Pro Pro Ser NH$_2$ |
| 26 | His Gly Glu Gly Thr Phe Thr Ser Asp Leu Ser Lys Gln Leu Glu Glu Glu Ala Val Arg Leu Phe Val Glu Phe Leu Lys Asn Gly Gly Pro Ser Ser Gly Ala Pro Pro Pro Ser NH$_2$ |
| 27 | His Gly Glu Gly Thr Phe Thr Ser Asp Leu Ser Lys Gln Met Glu Glu Glu Ala Val Arg Leu Phe tbutylGly Glu Trp Leu Lys Asn Gly Gly Pro Ser Ser Gly Ala Pro Pro Pro Ser NH$_2$ |
| 28 | His Gly Glu Gly Thr Phe Thr Ser Asp Leu Ser Lys Gln Leu Glu Glu Glu Ala Val Arg Leu Phe tbutylGly Glu Phe Leu Lys Asn Gly Gly Pro Ser Ser Gly Ala Pro Pro Pro Ser NH$_2$ |
| 29 | His Gly Glu Gly Thr Phe Thr Ser Asp Leu Ser Lys Gln Met Glu Glu Glu Ala Val Arg Leu Phe Ile Asp Trp Leu Lys Asn Gly Gly Pro Ser Ser Gly Ala Pro Pro Pro Ser NH$_2$ |
| 30 | His Ala Glu Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly Ala Pro Pro Pro Ser NH$_2$ |
| 31 | His Gly Glu Gly Thr Phe Thr Ser Asp Leu Ser Lys Gln Met Glu Glu Glu Ala Val Arg Leu Phe Ile Glu Trp Leu Lys Asn Gly Gly thioPro Ser Ser Gly Ala thioPro thioPro thioPro Ser NH$_2$ |
| 32 | His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala thioPro thioPro thioPro Ser NH$_2$ |
| 33 | His Gly Glu Gly Thr Phe Thr Ser Asp Leu Ser Lys Gln Met Glu Glu Glu Ala Val Arg Leu Phe Ile Glu Trp Leu Lys Asn Gly Gly homoPro Ser Ser Gly Ala homoPro homoPro homoPro Ser NH$_2$ |
| 34 | His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala homoPro homoPro homoPro Ser NH$_2$ |
| 35 | His Gly Glu Gly Thr Phe Thr Ser Asp Leu Ser Lys Gln Leu Glu Glu Glu Ala Val Arg Leu Phe Ile Glu Phe Leu Lys Asn Gly Gly thioPro Ser Ser Gly Ala thioPro thioPro thioPro Ser NH$_2$ |
| 36 | His Gly Glu Gly Thr Phe Thr Ser Asp Leu Ser Lys Gln Leu Glu Glu Glu Ala Val Arg Leu Phe Ile Glu Phe Leu Lys Asn Gly Gly homoPro Ser Ser Gly Ala homoPro homoPro homoPro Ser NH$_2$ |
| 37 | His Gly Glu Gly Thr Phe Thr Ser Asp Leu Ser Lys Gln Met Glu Glu Glu Ala Val Arg Leu Phe Ile Glu Trp Leu Lys Asn Gly Gly NmethylAla Ser Ser Gly Ala NmethylAla NmethylAla NmethylAla Ser NH$_2$ |

TABLE 1-continued

Exendins, Exendin Analogs and Exendin Derivatives

| SEQ ID NO | Sequence |
|---|---|
| 38 | His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala NmethylAla NmethylAla NmethylAla Ser NH$_2$ |
| 39 | His Gly Glu Gly Thr Phe Thr Ser Asp Leu Ser Lys Gln Leu Glu Glu Glu Ala Val Arg Leu Phe Ile Glu Phe Leu Lys Asn Gly Gly NmethylAla Ser Ser Gly Ala NmethylAla NmethylAla NmethylAla Ser NH$_2$ |
| 40 | His Gly Glu Gly Thr Phe Thr Ser Asp Leu Ser Lys Gln Met Glu Glu Glu Ala Val Arg Leu Phe Ile Glu Trp Leu Lys Asn-NH$_2$ |
| 41 | His Gly Glu Gly Thr Phe Thr Ser Asp Leu Ser Lys Gln Leu Glu Glu Glu Ala Val Arg Leu Phe Ile Glu Phe Leu Lys Asn-NH$_2$ |
| 42 | His Ala Glu Gly Thr Phe Thr Ser Asp Leu Ser Lys Gln Leu Glu Glu Glu Ala Val Arg Leu Phe Ile Glu Phe Leu Lys Asn-NH$_2$ |
| 43 | His Gly Glu Gly Ala Phe Thr Ser Asp Leu Ser Lys Gln Leu Glu Glu Glu Ala Val Arg Leu Phe Ile Glu Phe Leu Lys Asn-NH$_2$ |
| 44 | His Gly Glu Gly Thr Ala Thr Ser Asp Leu Ser Lys Gln Leu Glu Glu Glu Ala Val Arg Leu Phe Ile Glu Phe Leu Lys Asn-NH$_2$ |
| 45 | His Gly Glu Gly Thr Phe Thr Ala Asp Leu Ser Lys Gln Leu Glu Glu Glu Ala Val Arg Leu Phe Ile Glu Phe Leu Lys Asn-NH$_2$ |
| 46 | His Gly Glu Gly Thr Phe Thr Ser Asp Ala Ser Lys Gln Leu Glu Glu Glu Ala Val Arg Leu Phe Ile Glu Phe Leu Lys Asn-NH$_2$ |
| 47 | His Gly Glu Gly Thr Phe Thr Ser Asp Leu Ala Lys Gln Leu Glu Glu Glu Ala Val Arg Leu Phe Ile Glu Phe Leu Lys Asn-NH$_2$ |
| 48 | His Gly Glu Gly Thr Phe Thr Ser Asp Leu Ser Ala Gln Leu Glu Glu Glu Ala Val Arg Leu Phe Ile Glu Phe Leu Lys Asn-NH$_2$ |
| 49 | His Gly Glu Gly Thr Phe Thr Ser Asp Leu Ser Lys Ala Leu Glu Glu Glu Ala Val Arg Leu Phe Ile Glu Phe Leu Lys Asn-NH$_2$ |
| 50 | His Gly Glu Gly Thr Phe Thr Ser Asp Leu Ser Lys Gln Ala Glu Glu Glu Ala Val Arg Leu Phe Ile Glu Phe Leu Lys Asn-NH$_2$ |
| 51 | His Gly Glu Gly Thr Phe Thr Ser Asp Leu Ser Lys Gln Leu Ala Glu Glu Ala Val Arg Leu Phe Ile Glu Phe Leu Lys Asn-NH$_2$ |
| 52 | His Gly Glu Gly Thr Phe Thr Ser Asp Leu Ser Lys Gln Leu Glu Ala Glu Ala Val Arg Leu Phe Ile Glu Phe Leu Lys Asn-NH$_2$ |
| 53 | His Gly Glu Gly Thr Phe Thr Ser Asp Leu Ser Lys Gln Leu Glu Glu Ala Ala Val Arg Leu Phe Ile Glu Phe Leu Lys Asn-NH$_2$ |
| 54 | His Gly Glu Gly Thr Phe Thr Ser Asp Leu Ser Lys Gln Leu Glu Glu Glu Ala Ala Arg Leu Phe Ile Glu Phe Leu Lys Asn-NH$_2$ |
| 55 | His Gly Glu Gly Thr Phe Thr Ser Asp Leu Ser Lys Gln Leu Glu Glu Glu Ala Val Ala Leu Phe Ile Glu Phe Leu Lys Asn-NH$_2$ |
| 56 | His Gly Glu Gly Thr Phe Thr Ser Asp Leu Ser Lys Gln Leu Glu Glu Glu Ala Val Arg Ala Phe Ile Glu Phe Leu Lys Asn-NH$_2$ |
| 57 | His Gly Glu Gly Thr Phe Thr Ser Asp Leu Ser Lys Gln Leu Glu Glu Glu Ala Val Arg Leu Phe Ile Ala Phe Leu Lys Asn-NH$_2$ |
| 58 | His Gly Glu Gly Thr Phe Thr Ser Asp Leu Ser Lys Gln Leu Glu Glu Glu Ala Val Arg Leu Phe Ile Glu Ala Leu Lys Asn-NH$_2$ |
| 59 | His Gly Glu Gly Thr Phe Thr Ser Asp Leu Ser Lys Gln Leu Glu Glu Glu Ala Val Arg Leu Phe Ile Glu Phe Ala Lys Asn-NH$_2$ |
| 60 | His Gly Glu Gly Thr Phe Thr Ser Asp Leu Ser Lys Gln Leu Glu Glu Glu Ala Val Arg Leu Phe Ile Glu Phe Leu Ala Asn-NH$_2$ |
| 61 | His Gly Glu Gly Thr Phe Thr Ser Asp Leu Ser Lys Gln Leu Glu Glu Glu Ala Val Arg Leu Phe Ile Glu Phe Leu Lys Ala-NH$_2$ |
| 62 | His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro-NH$_2$ |
| 63 | His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly Ala Pro Pro Pro-NH$_2$ |
| 64 | His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro-NH$_2$ |
| 65 | His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly Ala Pro Pro-NH$_2$ |
| 66 | His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro-NH$_2$ |
| 67 | His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly Ala Pro-NH$_2$ |
| 68 | His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala-NH$_2$ |
| 69 | His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly Ala-NH$_2$ |
| 70 | His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly-NH$_2$ |
| 71 | His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly-NH$_2$ |
| 72 | His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser-NH$_2$ |
| 73 | His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro Ser Ser-NH$_2$ |

TABLE 1-continued

Exendins, Exendin Analogs and Exendin Derivatives

| SEQ ID NO | Sequence |
|---|---|
| 74 | His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser-$NH_2$ |
| 75 | His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro Ser-$NH_2$ |
| 76 | His Gly Glu Gly Thr Phe Thr Ser Asp Leu Ser Lys Gln Met Glu Glu Glu Ala Val Arg Leu Phe Ile Glu Trp Leu Lys Asn Gly Gly Pro-$NH_2$ |
| 77 | His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro-$NH_2$ |
| 78 | His Gly Glu Gly Thr Phe Thr Ser Asp Leu Ser Lys Gln Leu Glu Glu Glu Ala Val Arg Leu Phe Ile Glu Phe Leu Lys Asn Gly Gly-$NH_2$ |
| 79 | His Gly Glu Gly Thr Phe Thr Ser Asp Leu Ser Lys Gln Met Glu Glu Glu Ala Val Arg Leu Phe Ile Glu Trp Leu Lys Asn Gly-$NH_2$ |
| 80 | His Gly Glu Gly Thr Phe Thr Ser Asp Leu Ser Lys Gln Leu Glu Glu Glu Ala Val Arg Leu Phe Ile Glu Phe Leu Lys Asn Gly-$NH_2$ |
| 81 | His Gly Glu Gly Thr Phe Thr Ser Asp Leu Ser Lys Gln Met Glu Glu Glu Ala Val Arg Leu Phe Ile Glu Trp Leu Lys Asn Gly Gly thioPro Ser Ser Gly Ala thioPro thioPro thioPro-$NH_2$ |
| 82 | His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala thioPro thioPro thioPro-$NH_2$ |
| 83 | His Gly Glu Gly Thr Phe Thr Ser Asp Leu Ser Lys Gln Met Glu Glu Glu Ala Val Arg Leu Phe Ile Glu Trp Leu Lys Asn Gly Gly NMeAla Ser Ser Gly Ala Pro Pro-$NH_2$ |
| 84 | His Gly Glu Gly Thr Phe Thr Ser Asp Leu Ser Lys Gln Met Glu Glu Glu Ala Val Arg Leu Phe Ile Glu Trp Leu Lys Asn Gly Gly NMeAla Ser Ser Gly Ala NMeAla NmeAla-$NH_2$ |
| 85 | His Gly Glu Gly Thr Phe Thr Ser Asp Leu Ser Lys Gln Met Glu Glu Glu Ala Val Arg Leu Phe Ile Glu Trp Leu Lys Asn Gly Gly homoPro Ser Ser Gly Ala homoPro homoPro-$NH_2$ |
| 86 | His Gly Glu Gly Thr Phe Thr Ser Asp Leu Ser Lys Gln Met Glu Glu Glu Ala Val Arg Leu Phe Ile Glu Trp Leu Lys Asn Gly Gly homoPro Ser Ser Gly Ala homoPro-$NH_2$ |
| 87 | Arg Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala-$NH_2$ |
| 88 | His Gly Asp Gly Thr Phe Thr Ser Asp Leu Ser Lys Gln Met Glu Glu Glu Ala Val Arg Leu Phe Ile Glu Trp Leu Lys Asn Gly Gly-$NH_2$ |
| 89 | His Gly Glu Gly Thr NaphthylAla Thr Ser Asp Leu Ser Lys Gln Leu Glu Glu Glu Ala Val Arg Leu Phe Ile Glu Phe Leu Lys Asn-$NH_2$ |
| 90 | His Gly Glu Gly Thr Phe Ser Ser Asp Leu Ser Lys Gln Met Glu Glu Glu Ala Val Arg Leu Phe Ile Glu Trp Leu Lys Asn-$NH_2$ |
| 91 | His Gly Glu Gly Thr Phe Ser Thr Asp Leu Ser Lys Gln Met Glu Glu Glu Ala Val Arg Leu Phe Ile Glu Trp Leu Lys Asn-$NH_2$ |
| 92 | His Gly Glu Gly Thr Phe Thr Ser Glu Leu Ser Lys Gln Met Ala Glu Glu Ala Val Arg Leu Phe Ile Glu Trp Leu Lys Asn-$NH_2$ |
| 93 | His Gly Glu Gly Thr Phe Thr Ser Asp pentylGly Ser Lys Gln Leu Glu Glu Glu Ala Val Arg Leu Phe Ile Glu Phe Leu Lys Asn-$NH_2$ |
| 94 | His Gly Glu Gly Thr Phe Thr Ser Asp Leu Ser Lys Gln Leu Glu Glu Glu Ala Val Arg Leu NaphthylAla Ile Glu Phe Leu Lys Asn-$NH_2$ |
| 95 | His Gly Glu Gly Thr Phe Thr Ser Asp Leu Ser Lys Gln Met Glu Glu Glu Ala Val Arg Leu Phe tButylGly Glu Trp Leu Lys Asn-$NH_2$ |
| 96 | His Gly Glu Gly Thr Phe Thr Ser Asp Leu Ser Lys Gln Leu Glu Glu Glu Ala Val Arg Leu Phe Ile Asp Phe Leu Lys Asn-$NH_2$ |
| 97 | His Gly Glu Gly Thr Phe Thr Ser Asp Ala Ser Lys Gln Leu Glu Glu Glu Ala Val Arg Leu Phe Ile Glu Phe Leu Lys Asn Gly Gly Pro Ser Ser-$NH_2$ |
| 98 | His Gly Glu Gly Thr Phe Thr Ser Asp Ala Ser Lys Gln Met Glu Glu Glu Ala Val Arg Leu Phe Ile Glu Trp Leu Lys Asn Gly-$NH_2$ |
| 99 | His Gly Glu Gly Thr Phe Thr Ser Asp Ala Ser Lys Gln Met Glu Glu Glu Ala Val Arg Leu Phe Ile Glu Trp Leu Lys Asn Gly Gly homoPro Ser Ser Gly Ala homoPro homoPro-$NH_2$ |
| 100 | Ala Gly Glu Gly Thr Phe Thr Ser Asp Leu Ser Lys Gln Leu Glu Glu Glu Ala Val Arg Leu Phe Ile Glu Phe Leu Lys Asn-$NH_2$ |
| 101 | His Gly Ala Gly Thr Phe Thr Ser Asp Leu Ser Lys Gln Leu Glu Glu Glu Ala Val Arg Leu Phe Ile Glu Phe Leu Lys Asn-$NH_2$ |
| 102 | His Gly Glu Ala Thr Phe Thr Ser Asp Leu Ser Lys Gln Leu Glu Glu Glu Ala Val Arg Leu Phe Ile Glu Phe Leu Lys Asn-$NH_2$ |
| 103 | His Gly Glu Gly Thr Phe Thr Ser Ala Leu Ser Lys Gln Leu Glu Glu Glu Ala Val Arg Leu Phe Ile Glu Phe Leu Lys Asn-$NH_2$ |
| 104 | Ala Gly Glu Gly Thr Phe Thr Ser Asp Leu Ser Lys Gln Met Glu Glu Glu Ala Val Arg Leu Phe Ile Glu Trp Leu Lys Asn-$NH_2$ |
| 105 | His Gly Ala Gly Thr Phe Thr Ser Asp Leu Ser Lys Gln Met Glu Glu Glu Ala Val Arg Leu Phe Ile Glu Trp Leu Lys Asn-$NH_2$ |
| 106 | His Gly Glu Ala Thr Phe Thr Ser Asp Leu Ser Lys Gln Met Glu Glu Glu Ala Val Arg Leu Phe Ile Glu Trp Leu Lys Asn-$NH_2$ |
| 107 | His Gly Glu Gly Thr Phe Thr Ser Ala Leu Ser Lys Gln Met Glu Glu Glu Ala Val Arg Leu Phe Ile Glu Trp Leu Lys Asn-$NH_2$ |
| 108 | His Gly Glu Gly Thr Phe Thr Ser Asp Ala Ser Lys Gln Met Glu Glu Glu Ala Val Arg Leu Phe Ile Glu Trp Leu Lys Asn-$NH_2$ |
| 109 | Ala Ala Glu Gly Thr Phe Thr Ser Asp Leu Ser Lys Gln Met Glu Glu Glu Ala Val Arg Leu Phe Ile Glu Trp Leu Lys Asn-$NH_2$ |
| 110 | Ala Ala Glu Gly Thr Phe Thr Ser Asp Leu Ser Lys Gln Leu Glu Glu Glu Ala Val Arg Leu Phe Ile Glu Phe Leu Lys Asn-$NH_2$ |

TABLE 1-continued

Exendins, Exendin Analogs and Exendin Derivatives

| SEQ ID NO | Sequence |
|---|---|
| 111 | Ala Gly Asp Gly Thr Phe Thr Ser Asp Leu Ser Lys Gln Met Glu Glu Glu Ala Val Arg Leu Phe Ile Glu Trp Leu Lys Asn-NH$_2$ |
| 112 | Ala Gly Asp Gly Thr Phe Thr Ser Asp Leu Ser Lys Gln Leu Glu Glu Glu Ala Val Arg Leu Phe Ile Glu Phe Leu Lys Asn-NH$_2$ |
| 113 | Ala Gly Asp Gly Ala Phe Thr Ser Asp Leu Ser Lys Gln Met Glu Glu Glu Ala Val Arg Leu Phe Ile Glu Trp Leu Lys Asn-NH$_2$ |
| 114 | Ala Gly Asp Gly Ala Phe Thr Ser Asp Leu Ser Lys Gln Leu Glu Glu Glu Ala Val Arg Leu Phe Ile Glu Phe Leu Lys Asn-NH$_2$ |
| 115 | Ala Gly Asp Gly Thr NaphthylAla Thr Ser Asp Leu Ser Lys Gln Met Glu Glu Glu Ala Val Arg Leu Phe Ile Glu Trp Leu Lys Asn-NH$_2$ |
| 116 | Ala Gly Asp Gly Thr NaphthylAla Thr Ser Asp Leu Ser Lys Gln Leu Glu Glu Glu Ala Val Arg Leu Phe Ile Glu Phe Leu Lys Asn-NH$_2$ |
| 117 | Ala Gly Asp Gly Thr Phe Ser Ser Asp Leu Ser Lys Gln Met Glu Glu Glu Ala Val Arg Leu Phe Ile Glu Trp Leu Lys Asn-NH$_2$ |
| 118 | Ala Gly Asp Gly Thr Phe Ser Ser Asp Leu Ser Lys Gln Leu Glu Glu Glu Ala Val Arg Leu Phe Ile Glu Phe Leu Lys Asn-NH$_2$ |
| 119 | Ala Gly Asp Gly Thr Phe Thr Ala Asp Leu Ser Lys Gln Met Glu Glu Glu Ala Val Arg Leu Phe Ile Glu Trp Leu Lys Asn-NH$_2$ |
| 120 | Ala Gly Asp Gly Thr Phe Thr Ala Asp Leu Ser Lys Gln Leu Glu Glu Glu Ala Val Arg Leu Phe Ile Glu Phe Leu Lys Asn-NH$_2$ |
| 121 | Ala Gly Asp Gly Thr Phe Thr Ser Ala Leu Ser Lys Gln Met Glu Glu Glu Ala Val Arg Leu Phe Ile Glu Trp Leu Lys Asn-NH$_2$ |
| 122 | Ala Gly Asp Gly Thr Phe Thr Ser Ala Leu Ser Lys Gln Leu Glu Glu Glu Ala Val Arg Leu Phe Ile Glu Phe Leu Lys Asn-NH$_2$ |
| 123 | Ala Gly Asp Gly Thr Phe Thr Ser Glu Leu Ser Lys Gln Met Glu Glu Glu Ala Val Arg Leu Phe Ile Glu Trp Leu Lys Asn-NH$_2$ |
| 124 | Ala Gly Asp Gly Thr Phe Thr Ser Glu Leu Ser Lys Gln Leu Glu Glu Glu Ala Val Arg Leu Phe Ile Glu Phe Leu Lys Asn-NH$_2$ |
| 125 | Ala Gly Asp Gly Thr Phe Thr Ser Asp Ala Ser Lys Gln Met Glu Glu Glu Ala Val Arg Leu Phe Ile Glu Trp Leu Lys Asn-NH$_2$ |
| 126 | Ala Gly Asp Gly Thr Phe Thr Ser Asp Ala Ser Lys Gln Leu Glu Glu Glu Ala Val Arg Leu Phe Ile Glu Phe Leu Lys Asn-NH$_2$ |
| 127 | Ala Gly Asp Gly Thr Phe Thr Ser Asp pentylGly Ser Lys Gln Met Glu Glu Glu Ala Val Arg Leu Phe Ile Glu Trp Leu Lys Asn-NH$_2$ |
| 128 | Ala Gly Asp Gly Thr Phe Thr Ser Asp pentylGly Ser Lys Gln Leu Glu Glu Glu Ala Val Arg Leu Phe Ile Glu Phe Leu Lys Asn-NH$_2$ |
| 129 | Ala Gly Asp Gly Thr Phe Thr Ser Asp Leu Ala Lys Gln Met Glu Glu Glu Ala Val Arg Leu Phe Ile Glu Trp Leu Lys Asn-NH$_2$ |
| 130 | Ala Gly Asp Gly Thr Phe Thr Ser Asp Leu Ala Lys Gln Leu Glu Glu Glu Ala Val Arg Leu Phe Ile Glu Phe Leu Lys Asn-NH$_2$ |
| 131 | Ala Gly Asp Gly Thr Phe Thr Ser Asp Leu Ser Ala Gln Met Glu Glu Glu Ala Val Arg Leu Phe Ile Glu Trp Leu Lys Asn-NH$_2$ |
| 132 | Ala Gly Asp Gly Thr Phe Thr Ser Asp Leu Ser Ala Gln Leu Glu Glu Glu Ala Val Arg Leu Phe Ile Glu Phe Leu Lys Asn-NH$_2$ |
| 133 | Ala Gly Asp Gly Thr Phe Thr Ser Asp Leu Ser Lys Ala Met Glu Glu Glu Ala Val Arg Leu Phe Ile Glu Trp Leu Lys Asn-NH$_2$ |
| 134 | Ala Gly Asp Gly Thr Phe Thr Ser Asp Leu Ser Lys Ala Leu Glu Glu Glu Ala Val Arg Leu Phe Ile Glu Phe Leu Lys Asn-NH$_2$ |
| 135 | Ala Gly Asp Gly Thr Phe Thr Ser Asp Leu Ser Lys Gln Ala Glu Glu Glu Ala Val Arg Leu Phe Ile Glu Trp Leu Lys Asn-NH$_2$ |
| 136 | Ala Gly Asp Gly Thr Phe Thr Ser Asp Leu Ser Lys Gln Ala Glu Glu Glu Ala Val Arg Leu Phe Ile Glu Phe Leu Lys Asn-NH$_2$ |
| 137 | Ala Gly Asp Gly Thr Phe Thr Ser Asp Leu Ser Lys Gln pentylGly Glu Glu Glu Ala Val Arg Leu Phe Ile Glu Trp Leu Lys Asn-NH$_2$ |
| 138 | Ala Gly Asp Gly Thr Phe Thr Ser Asp Leu Ser Lys Gln pentylGly Glu Glu Glu Ala Val Arg Leu Phe Ile Glu Phe Leu Lys Asn-NH$_2$ |
| 139 | Ala Gly Asp Gly Thr Phe Thr Ser Asp Leu Ser Lys Gln Met Ala Glu Glu Ala Val Arg Leu Phe Ile Glu Trp Leu Lys Asn-NH$_2$ |
| 140 | Ala Gly Asp Gly Thr Phe Thr Ser Asp Leu Ser Lys Gln Leu Ala Glu Glu Ala Val Arg Leu Phe Ile Glu Phe Leu Lys Asn-NH$_2$ |
| 141 | Ala Gly Asp Gly Thr Phe Thr Ser Asp Leu Ser Lys Gln Met Glu Ala Glu Ala Val Arg Leu Phe Ile Glu Trp Leu Lys Asn-NH$_2$ |
| 142 | Ala Gly Asp Gly Thr Phe Thr Ser Asp Leu Ser Lys Gln Leu Glu Ala Glu Ala Val Arg Leu Phe Ile Glu Phe Leu Lys Asn-NH$_2$ |
| 143 | Ala Gly Asp Gly Thr Phe Thr Ser Asp Leu Ser Lys Gln Met Glu Glu Ala Ala Val Arg Leu Phe Ile Glu Trp Leu Lys Asn-NH$_2$ |
| 144 | Ala Gly Asp Gly Thr Phe Thr Ser Asp Leu Ser Lys Gln Leu Glu Glu Ala Ala Val Arg Leu Phe Ile Glu Phe Leu Lys Asn-NH$_2$ |
| 145 | Ala Gly Asp Gly Thr Phe Thr Ser Asp Leu Ser Lys Gln Met Glu Glu Glu Ala Ala Arg Leu Phe Ile Glu Trp Leu Lys Asn-NH$_2$ |
| 146 | Ala Gly Asp Gly Thr Phe Thr Ser Asp Leu Ser Lys Gln Leu Glu Glu Glu Ala Ala Arg Leu Phe Ile Glu Phe Leu Lys Asn-NH$_2$ |
| 147 | Ala Gly Asp Gly Thr Phe Thr Ser Asp Leu Ser Lys Gln Met Glu Glu Glu Ala Val Ala Leu Phe Ile Glu Trp Leu Lys Asn-NH$_2$ |

TABLE 1-continued

Exendins, Exendin Analogs and Exendin Derivatives

| SEQ ID NO | Sequence |
|---|---|
| 148 | Ala Gly Asp Gly Thr Phe Thr Ser Asp Leu Ser Lys Gln Leu Glu Glu Glu Ala Val Ala Leu Phe Ile Glu Phe Leu Lys Asn-$NH_2$ |
| 149 | Ala Gly Asp Gly Thr Phe Thr Ser Asp Leu Ser Lys Gln Met Glu Glu Glu Ala Val Arg Ala Phe Ile Glu Trp Leu Lys Asn-$NH_2$ |
| 150 | Ala Gly Asp Gly Thr Phe Thr Ser Asp Leu Ser Lys Gln Leu Glu Glu Glu Ala Val Arg Ala Phe Ile Glu Phe Leu Lys Asn-$NH_2$ |
| 151 | Ala Gly Asp Gly Thr Phe Thr Ser Asp Leu Ser Lys Gln Met Glu Glu Glu Ala Val Arg Leu NaphthylAla Ile Glu Trp Leu Lys Asn-$NH_2$ |
| 152 | Ala Gly Asp Gly Thr Phe Thr Ser Asp Leu Ser Lys Gln Leu Glu Glu Glu Ala Val Arg Leu NaphthylAla Ile Glu Phe Leu Lys Asn-$NH_2$ |
| 153 | Ala Gly Asp Gly Thr Phe Thr Ser Asp Leu Ser Lys Gln Met Glu Glu Glu Ala Val Arg Leu Phe Val Glu Trp Leu Lys Asn-$NH_2$ |
| 154 | Ala Gly Asp Gly Thr Phe Thr Ser Asp Leu Ser Lys Gln Leu Glu Glu Glu Ala Val Arg Leu Phe Val Glu Phe Leu Lys Asn-$NH_2$ |
| 155 | Ala Gly Asp Gly Thr Phe Thr Ser Asp Leu Ser Lys Gln Met Glu Glu Glu Ala Val Arg Leu Phe tButylGly Glu Trp Leu Lys Asn-$NH_2$ |
| 156 | Ala Gly Asp Gly Thr Phe Thr Ser Asp Leu Ser Lys Gln Leu Glu Glu Glu Ala Val Arg Leu Phe tButylGly Glu Phe Leu Lys Asn-$NH_2$ |
| 157 | Ala Gly Asp Gly Thr Phe Thr Ser Asp Leu Ser Lys Gln Met Glu Glu Glu Ala Val Arg Leu Phe Ile Asp Trp Leu Lys Asn-$NH_2$ |
| 158 | Ala Gly Asp Gly Thr Phe Thr Ser Asp Leu Ser Lys Gln Leu Glu Glu Glu Ala Val Arg Leu Phe Ile Asp Phe Leu Lys Asn-$NH_2$ |
| 159 | Ala Gly Asp Gly Thr Phe Thr Ser Asp Leu Ser Lys Gln Met Glu Glu Glu Ala Val Arg Leu Phe Ile Glu Ala Leu Lys Asn-$NH_2$ |
| 160 | Ala Gly Asp Gly Thr Phe Thr Ser Asp Leu Ser Lys Gln Leu Glu Glu Glu Ala Val Arg Leu Phe Ile Glu Ala Leu Lys Asn-$NH_2$ |
| 161 | Ala Gly Asp Gly Thr Phe Thr Ser Asp Leu Ser Lys Gln Met Glu Glu Glu Ala Val Arg Leu Phe Ile Glu Trp Ala Lys Asn-$NH_2$ |
| 162 | Ala Gly Asp Gly Thr Phe Thr Ser Asp Leu Ser Lys Gln Leu Glu Glu Glu Ala Val Arg Leu Phe Ile Glu Phe Ala Lys Asn-$NH_2$ |
| 163 | Ala Gly Asp Gly Thr Phe Thr Ser Asp Leu Ser Lys Gln Met Glu Glu Glu Ala Val Arg Leu Phe Ile Glu Trp Leu Ala Asn-$NH_2$ |
| 164 | Ala Gly Asp Gly Thr Phe Thr Ser Asp Leu Ser Lys Gln Leu Glu Glu Glu Ala Val Arg Leu Phe Ile Glu Phe Leu Ala Asn-$NH_2$ |
| 165 | Ala Gly Asp Gly Thr Phe Thr Ser Asp Leu Ser Lys Gln Met Glu Glu Glu Ala Val Arg Leu Phe Ile Glu Trp Leu Lys Ala-$NH_2$ |
| 166 | Ala Gly Asp Gly Thr Phe Thr Ser Asp Leu Ser Lys Gln Leu Glu Glu Glu Ala Val Arg Leu Phe Ile Glu Phe Leu Lys Ala-$NH_2$ |
| 167 | Ala Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro-$NH_2$ |
| 168 | His Gly Ala Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly Ala Pro Pro Pro-$NH_2$ |
| 169 | His Gly Glu Ala Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro-$NH_2$ |
| 170 | His Gly Glu Gly Thr Phe Thr Ser Ala Leu Ser Lys Gln Met Glu Glu Glu Ala Val Arg Leu Phe Ile Glu Trp Leu Lys Asn Gly Gly Pro Ser Ser Gly Ala Pro-$NH_2$ |
| 171 | Ala Gly Glu Gly Thr Phe Thr Ser Asp Ala Ser Lys Gln Leu Glu Glu Glu Ala Val Arg Leu Phe Ile Glu Phe Leu Lys Asn Gly Gly Pro Ser Ser Gly Ala Pro-$NH_2$ |
| 172 | Ala Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala-$NH_2$ |
| 173 | His Gly Ala Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly Ala-$NH_2$ |
| 174 | His Gly Glu Ala Thr Phe Thr Ser Asp Leu Ser Lys Gln Met Glu Glu Glu Ala Val Arg Leu Phe Ile Glu Trp Leu Lys Asn Gly Gly Pro Ser Ser Gly-$NH_2$ |
| 175 | His Gly Glu Gly Thr Phe Thr Ser Ala Leu Ser Lys Gln Met Glu Glu Glu Ala Val Arg Leu Phe Ile Glu Trp Leu Lys Asn Gly Gly Pro Ser Ser-$NH_2$ |
| 176 | Ala Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser-$NH_2$ |
| 177 | His Gly Ala Gly Thr Phe Thr Ser Asp Leu Ser Lys Gln Leu Glu Glu Glu Ala Val Arg Leu Phe Ile Glu Phe Leu Lys Asn Gly Gly Pro Ser-$NH_2$ |
| 178 | His Gly Glu Ala Thr Phe Thr Ser Asp Leu Ser Lys Gln Met Glu Glu Glu Ala Val Arg Leu Phe Ile Glu Trp Leu Lys Asn Gly Gly Pro-$NH_2$ |
| 179 | His Gly Glu Gly Thr Phe Thr Ser Ala Leu Ser Lys Gln Leu Glu Glu Glu Ala Val Arg Leu Phe Ile Glu Phe Leu Lys Asn Gly Gly-$NH_2$ |
| 180 | Ala Gly Glu Gly Thr Phe Thr Ser Asp Leu Ser Lys Gln Leu Glu Glu Glu Ala Val Arg Leu Phe Ile Glu Phe Leu Lys Asn Gly Gly-$NH_2$ |
| 181 | His Gly Ala Gly Thr Phe Thr Ser Asp Leu Ser Lys Gln Met Glu Glu Glu Ala Val Arg Leu Phe Ile Glu Trp Leu Lys Asn Gly Gly thioPro Ser Ser Gly Ala thioPro thioPro thioPro-$NH_2$ |
| 182 | His Gly Glu Ala Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala thioPro thioPro thioPro-$NH_2$ |
| 183 | His Gly Glu Gly Thr Phe Thr Ser Ala Leu Ser Lys Gln Met Glu Glu Glu Ala Val Arg Leu Phe Ile Glu Trp Leu Lys Asn Gly Gly NMeAla Ser Ser Gly Ala NMeAla NMeAla-$NH_2$ |
| 184 | Ala Gly Glu Gly Thr Phe Thr Ser Asp Leu Ser Lys Gln Met Glu Glu Glu Ala Val Arg Leu Phe Ile Glu Trp Leu Lys Asn Gly Gly homoPro Ser Ser Gly Ala homoPro-$NH_2$ |

TABLE 1-continued

Exendins, Exendin Analogs and Exendin Derivatives

| SEQ ID NO | Sequence |
|---|---|
| 185 | His Gly Ala Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala-NH$_2$ |
| 186 | His Gly Asp Ala Thr Phe Thr Ser Asp Leu Ser Lys Gln Met Glu Glu Glu Ala Val Arg Leu Phe Ile Glu Trp Leu Lys Asn Gly Gly-NH$_2$ |
| 187 | Ala Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro Ser-NH$_2$ |
| 188 | Ala Gly Ala Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly Ala Pro Pro Pro Ser-NH$_2$ |

In one embodiment, the bioactive peptide or protein of the compositions described herein comprise PYY peptides, PYY peptide analogs and PYY derivatives, such as PYY$_{3-36}$. Additional PYY peptides that can be used in the compositions disclosed herein include any bioactive PYY peptide, PYY analog or PYY derivative known in the art such as those as described in International Patent Application Publication Nos. WO 02/47712 and WO 03/26591; and US Patent Application Publication No. 2002-141985, all of which are herein incorporated by reference in their entireties and in particular the PYY-related sequences disclosed therein. By "PYY" or "PYY peptide" is meant a Peptide YY polypeptide obtained or derived from any species. Thus, the term "PYY" includes the 36 amino acid full length human as well as species variations of PYY, including, but not limited to, murine, hamster, chicken, bovine, rat and dog PYY. Particular examples of PYY peptides, PYY analogs and PYY derivatives that can be used in the compositions disclosed herein, include, but are not limited to those described in Table 2. Also included are other Y receptor family peptide agonists, particularly Y2, Y5, and putative Y7 receptor agonists and derivatives thereof. In one embodiment, the bioactive peptide is PYY$_{3-36}$. PYY peptides are known to have activity in food intake, gastric emptying, pancreatic secretion and weight loss.

In additional embodiments, the bioactive peptide or protein of the compositions disclosed herein comprise GLP-1, GLP-1 analogs and GLP-1 derivatives such as GLP-1 (7-37), GLP-1(7-36)NH$_2$, Gly$^8$ GLP-1(7-37), Ser$^{34}$ GLP-1(7-37) Val$^8$ GLP-1(7-37) and Val$^8$ Glu$^{22}$ GLP-1(7-37). Any bioactive GLP-1, GLP-1 analog or GLP-1 derivative known in the art can be used in the present compositions, including, but not limited to those described in International Patent Application Publications Nos. WO 01/98331, WO 02/48192; US Patent Application Nos. 2003-220243 and 2004-053819; and U.S. Pat. Nos. 5,981,488, 5,574,008, 5,512,549, and 5,705,483, all of which are herein incorporated by reference in their entireties and in particular the GLP-1-related sequences described therein. Examples of GLP-1 peptides that are suitable for use in the compositions disclosed herein are those described in US Patent Application 2003-220243 by the following formulas:

Formula IV (SEQ ID No. 244)
His-Xaa$_8$-Glu-Gly-Xaa$_{11}$-Xaa$_{12}$-Thr-Ser-Asp-Xaa$_{16}$-Ser-Ser-Tyr-Leu-Glu-Xaa$_{22}$-Xaa$_{23}$-Xaa$_{24}$-Ala-Xaa$_{26}$-Xaa$_{27}$-Phe-Ile-Ala-Xaa$_{31}$-Leu-Xaa$_{33}$-Xaa$_{34}$-Xaa$_{35}$-Xaa$_{36}$-R
where:
Xaa$_8$ is Gly, Ala, Val, Leu, Ile, Ser, or Thr;
Xaa$_{11}$ is Asp, Glu, Arg, Thr, Ala, Lys, or His;

TABLE 2

PYY Peptides, Analogs and Derivatives

| SEQ ID NO | Sequence |
|---|---|
| 189 | Ala Pro Leu Glu Pro Val Tyr Pro Gly Asp Asn Ala Thr Pro Glu Gln Met Ala Gln Tyr Ala Ala Asp Leu Arg Arg Tyr Ile Asn Met Leu Thr Arg Pro Arg Tyr |
| 190 | Tyr Pro Ile Lys Pro Glu Ala Pro Gly Glu Asp Ala Ser Pro Glu Glu Leu Asn Arg Tyr Tyr Ala Ser Leu Arg His Tyr Leu Asn Leu Val Thr Arg Gln Arg Tyr |
| 191 | Ile Lys Pro Glu Ala Pro Gly Glu Asp Ala Ser Pro Glu Glu Leu Asn Arg Tyr Tyr Ala Ser Leu Arg His Tyr Leu Asn Leu Val Thr Arg Gln Arg Tyr |
| 192 | Tyr Pro Ser Lys Pro Asp Asn Pro Gly Glu Asp Ala Pro Ala Glu Asp Met Ala Arg Tyr Tyr Ser Ala Leu Arg His Tyr Ile Asn Leu Ile Thr Mg Gln Arg Tyr |
| 193 | Ser Lys Pro Asp Asn Pro Gly Glu Asp Ala Pro Ala Glu Asp Met Ala Arg Tyr Tyr Ser Ala Leu Arg His Tyr Ile Asn Leu Ile Thr Arg Gln Arg Tyr |
| 194 | Ala Ser Leu Arg His Tyr Leu Asn Leu Val Thr Arg Gln Arg Tyr |

Xaa$_{12}$ is His, Trp, Phe, or Tyr;
Xaa$_{16}$ is Leu, Ser, Thr, Trp, His, Phe, Asp, Val, Glu, or Ala;
Xaa$_{22}$ is Gly, Asp, Glu, Gln, Asn, Lys, Arg, Cys, or Cysteic Acid;
Xaa$_{23}$ is His, Asp, Lys, Glu, or Gln;
Xaa$_{24}$ is Glu, His, Ala, or Lys;
Xaa$_{26}$ is Asp, Lys, Glu, or His;
Xaa$_{27}$ is Ala, Glu, His, Phe, Tyr, Trp, Arg, or Lys;
Xaa$_{31}$ is Ala, Glu, Asp, Ser, or His;
Xaa$_{33}$ is Asp, Arg, Val, Lys, Ala, Gly, or Glu;
Xaa$_{34}$ is Glu, Lys, or Asp;
Xaa$_{35}$ is Thr, Ser, Lys, Arg, Trp, Tyr, Phe, Asp, Gly, Pro, His, or Glu;
Xaa$_{36}$ is Arg, Glu, or His; and
R is: Lys, Arg, Thr, Ser, Glu, Asp, Trp, Tyr, Phe, His, —NH$_2$, Gly, Gly-Pro, or Gly-Pro-NH$_2$, or is deleted.

Formula V (SEQ ID No. 245)
His-Xaa$_8$-Glu-Gly-Thr-Xaa$_{12}$-Thr-Ser-Asp-Xaa$_{16}$-Ser-Ser-Tyr-Leu-Glu-Xaa$_{22}$-Xaa$_{23}$-Ala-Ala-Xaa$_{26}$-Glu-Phe-Ile-Xaa$_{30}$-Trp-Leu-Val-Lys-Xaa$_{35}$-Arg-R
where:
Xaa$_8$ is Gly, Ala, Val, Leu, Ile, Ser, or Thr;
Xaa$_{12}$ is His, Trp, Phe, or Tyr;
Xaa$_{16}$ is Leu, Ser, Thr, Trp, His, Phe, Asp, Val, Glu, or Ala;
Xaa$_{22}$ is Gly, Asp, Glu, Gln, Asn, Lys, Arg, Cys, or Cysteic Acid (3-Sulfoalanine);
Xaa$_{23}$ is His, Asp, Lys, Glu, or Gln;
Xaa$_{26}$ is: Asp, Lys, Glu, or His;
Xaa$_{30}$ is Ala, Glu, Asp, Ser, or His;
Xaa$_{35}$ is Thr, Ser, Lys, Arg, Trp, Tyr, Phe, Asp, Gly, Pro, His, or Glu; and
R is: Lys, Arg, Thr, Ser, Glu, Asp, Trp, Tyr, Phe, His, —NH$_2$, Gly, Gly-Pro, or Gly-Pro-NH$_2$, or is deleted.

Formula VI (SEQ ID No. 246)
His-Xaa$_8$-Glu-Gly-Thr-Phe-Thr-Ser-Asp-Val-Ser-Ser-Tyr-Leu-Glu-Xaa$_{22}$-Xaa$_{23}$-Ala-Ala-Lys-Xaa$_{27}$-Phe-Ile-Xaa$_{30}$-Trp-Leu-Val-Lys-Gly-Arg-R
where:
Xaa$_8$ is Gly, Ala, Val, Leu, Ile, Ser, or Thr;
Xaa$_{22}$ is Gly, Asp, Glu, Gln, Asn, Lys, Arg, Cys, or Cysteic Acid (3-Sulfoalanine);
Xaa$_{23}$ is His, Asp, Lys, Glu, or Gln;
Xaa$_{27}$ is Ala, Glu, His, Phe, Tyr, Trp, Arg, or Lys
Xaa$_{30}$ is Ala, Glu, Asp, Ser, or His; and
R is: Lys, Arg, Thr, Ser, Glu, Asp, Trp, Tyr, Phe, His, —NH$_2$, Gly, Gly-Pro, or Gly-Pro-NH$_2$, or is deleted.

Formula VII (SEQ ID No. 247)
Xaa$_7$-Xaa$_8$-Glu-Gly-Thr-Phe-Thr-Ser-Asp-Val-Ser-Ser-Tyr-Leu-Glu-Xaa$_{22}$-Gln-Ala-Ala-Lys-Glu-Phe-Ile-Ala-Trp-Leu-Val-Lys-Gly-Arg-R
where:
Xaa$_7$ is L-histidine, D-histidine, desamino-histidine, 2amino-histidine, β-hydroxy-histidine, homohistidine, α-fluoromethyl-histidine or α-methyl-histidine;
Xaa$_8$ is glycine, alanine, valine, leucine, isoleucine, serine or threonine;
Xaa$_{22}$ is aspartic acid, glutamic acid, glutamine, asparagine, lysine, arginine, cysteine, or cysteic acid; and
R is —NH$_2$ or Gly(OH).

Particular, but non-limiting examples of GLP1 peptides that can be use in the present compositions can be found in Table 3

TABLE 3

GLP-1 Peptides, Analogs and Derivatives

| SEQ ID NO | Sequence |
|---|---|
| 195 | His Val Glu Gly Thr Phe Thr Ser Asp Val Ser Ser Tyr Leu Glu Glu Gln Ala Ala Lys Glu Phe Ile Ala Trp Leu Val Lys Gly Arg Gly |
| 196 | His Val Glu Gly Thr Phe Thr Ser Asp Val Ser Ser Tyr Leu Glu Asp Gln Ala Ala Lys Glu Phe Ile Ala Trp Leu Val Lys Gly Arg Gly |
| 197 | His Val Glu Gly Thr Phe Thr Ser Asp Val Ser Ser Tyr Leu Glu Arg Gln Ala Ala Lys Glu Phe Ile Ala Trp Leu Val Lys Gly Arg Gly |
| 198 | His Val Glu Gly Thr Phe Thr Ser Asp Val Ser Ser Tyr Leu Glu Lys Gln Ala Ala Lys Glu Phe Ile Ala Trp Leu Val Lys Gly Arg Gly |
| 199 | His Gly Glu Gly Thr Phe Thr Ser Asp Val Ser Ser Tyr Leu Glu Glu Gln Ala Ala Lys Glu Phe Ile Ala Trp Leu Val Lys Gly Arg Gly |
| 200 | His Gly Glu Gly Thr Phe Thr Ser Asp Val Ser Ser Tyr Leu Glu Asp Gln Ala Ala Lys Glu Phe Ile Ala Trp Leu Val Lys Gly Arg Gly |
| 201 | His Gly Glu Gly Thr Phe Thr Ser Asp Val Ser Ser Tyr Leu Glu Arg Gln Ala Ala Lys Glu Phe Ile Ala Trp Leu Val Lys Gly Arg Gly |
| 202 | His Gly Glu Gly Thr Phe Thr Ser Asp Val Ser Ser Tyr Leu Glu Lys Gln Ala Ala Lys Glu Phe Ile Ala Trp Leu Val Lys Gly Arg Gly |
| 203 | His Val Glu Gly Thr Phe Thr Ser Asp Val Ser Ser Tyr Leu Glu Gly Gln Ala Ala Lys Glu Phe Ile Glu Trp Leu Val Lys Gly Arg Gly |
| 204 | His Gly Glu Gly Thr Phe Thr Ser Asp Val Ser Ser Tyr Leu Glu Gly Gln Ala Ala Lys Glu Phe Ile Glu Trp Leu Val Lys Gly Arg Gly |
| 205 | His Val Glu Gly Thr Phe Thr Ser Asp Val Ser Ser Tyr Leu Glu Gly Gln Ala Ala Lys Glu Phe Ile Ala Trp Leu Val Lys Gly Arg His |

TABLE 3-continued

GLP-1 Peptides, Analogs and Derivatives

SEQ
ID
NO Sequence

206 His Gly Glu Gly Thr Phe Thr Ser Asp Val Ser Ser Tyr Leu Glu Gly Gln Ala Ala Lys Glu Phe Ile Ala Trp Leu Val Lys Gly Arg His

207 His Val Glu Gly Thr Phe Thr Ser Asp Val Ser Ser Tyr Leu Glu Glu Gln Ala Ala Lys Ala Phe Ile Ala Trp Leu Val Lys Gly Arg His

208 His Val Glu Gly Thr Phe Thr Ser Asp Val Ser Ser Tyr Leu Glu Lys Glu Ala Ala Lys Glu Phe Ile Ala Trp Leu Val Lys Gly Arg His

209 His Ala Glu Gly Thr Phe Thr Ser Asp Val Ser Ser Tyr Leu Glu Gly Gln Ala Ala Lys Glu Phe Ile Ala Trp Leu Val Lys Gly Arg Gly

210 His Ala Glu Gly Thr Phe Thr Ser Asp Val Ser Ser Tyr Leu Glu Glu Gln Ala Ala Lys Glu Phe Ile Ala Trp Leu Val Lys Gly Arg Gly

211 His Ala Glu Gly Thr Phe Thr Ser Asp Val Ser Ser Tyr Leu Glu Asp Gln Ala Ala Lys Glu Phe Ile Ala Trp Leu Val Lys Gly Arg Gly

212 His Ala Glu Gly Thr Phe Thr Ser Asp Val Ser Ser Tyr Leu Glu Arg Gln Ala Ala Lys Glu Phe Ile Ala Trp Leu Val Lys Gly Arg Gly

213 His Ala Glu Gly Thr Phe Thr Ser Asp Val Ser Ser Tyr Leu Glu Lys Gln Ala Ala Lys Glu Phe Ile Ala Trp Leu Val Lys Gly Arg Gly

214 His Ala Glu Gly Thr Phe Thr Ser Asp Val Ser Ser Tyr Leu Glu 3-sulfoAla Gln Ala Ala Lys Glu Phe Ile Ala Trp Leu Val Lys Gly Arg Gly 215 His Val Glu Gly Thr Phe Thr Ser Asp Val Ser Ser Tyr Leu Glu 3-sulfoAla Gln Ala Ala Lys Glu Phe Ile Ala Trp Leu Val Lys Gly Arg Gly 216 His Gly Glu Gly Thr Phe Thr Ser Asp Val Ser Ser Tyr Leu Glu 3-sulfoAla Gln Ala Ala Lys Glu Phe Ile Ala Trp Leu Val Lys Gly Arg Gly 217 His Ala Glu Gly Thr Phe Thr Ser Asp Val Ser Ser Tyr Leu Glu Glu Gln Ala Ala Lys Glu Phe Ile Ala Trp Leu Val Lys Gly Arg 218 His Ala Glu Gly Thr Phe Thr Ser Asp Val Ser Ser Tyr Leu Glu Asp Gln Ala Ala Lys Glu Phe Ile Ala Trp Leu Val Lys Gly Arg 219 His Ala Glu Gly Thr Phe Thr Ser Asp Val Ser Ser Tyr Leu Glu Arg Gln Ala Ala Lys Glu Phe Ile Ala Trp Leu Val Lys Gly Arg 220 His Ala Glu Gly Thr Phe Thr Ser Asp Val Ser Ser Tyr Leu Glu Lys Gln Ala Ala Lys Glu Phe Ile Ala Trp Leu Val Lys Gly Arg 221 His Ala Glu Gly Thr Phe Thr Ser Asp Val Ser Ser Tyr Leu Glu 3-sulfoAla Gln Ala Ala Lys Glu Phe Ile Ala Trp Leu Val Lys Gly Arg 222 His Val Glu Gly Thr Phe Thr Ser Asp Val Ser Ser Tyr Leu Glu Glu Gln Ala Ala Lys Glu Phe Ile Ala Trp Leu Val Lys Gly Arg 223 His Val Glu Gly Thr Phe Thr Ser Asp Val Ser Ser Tyr Leu Glu Asp Gln Ala Ala Lys Glu Phe Ile Ala Trp Leu Val Lys Gly Arg 224 His Val Glu Gly Thr Phe Thr Ser Asp Val Ser Ser Tyr Leu Glu Arg Gln Ala Ala Lys Glu Phe Ile Ala Trp Leu Val Lys Gly Arg 225 His Val Glu Gly Thr Phe Thr Ser Asp Val Ser Ser Tyr Leu Glu Lys Gln Ala Ala Lys Glu Phe Ile Ala Trp Leu Val Lys Gly Arg 226 His Val Glu Gly Thr Phe Thr Ser Asp Val Ser Ser Tyr Leu Glu 3-sulfoAla Gln Ala Ala Lys Glu Phe Ile Ala Trp Leu Val Lys Gly Arg 227 His Gly Glu Gly Thr Phe Thr Ser Asp Val Ser Ser Tyr Leu Glu Glu Gln Ala Ala Lys Glu Phe Ile Ala Trp Leu Val Lys Gly Arg 228 His Gly Glu Gly Thr Phe Thr Ser Asp Val Ser Ser Tyr Leu Glu Asp Gln Ala Ala Lys Glu Phe Ile Ala Trp Leu Val Lys Gly Arg 229 His Gly Glu Gly Thr Phe Thr Ser Asp Val Ser Ser Tyr Leu Glu Arg Gln Ala Ala Lys Glu Phe Ile Ala Trp Leu Val Lys Gly Arg

TABLE 3-continued

GLP-1 Peptides, Analogs and Derivatives

| SEQ ID NO | Sequence |
|---|---|
| 230 | His Gly Glu Gly Thr Phe Thr Ser Asp Val Ser Ser Tyr Leu Glu Lys Gln Ala Ala Lys Glu Phe Ile Ala Trp Leu Val Lys Gly Arg |
| 231 | His Gly Glu Gly Thr Phe Thr Ser Asp Val Ser Ser Tyr Leu Glu 3-sulfoAla Gln Ala Ala Lys Glu Phe Ile Ala Trp Leu Val Lys Gly Arg |
| 232 | His Val Glu Gly Thr Phe Thr Ser Asp Val Ser Ser Tyr Leu Glu Gly Lys Ala Ala Lys Glu Phe Ile Ala Trp Leu Val Lys Gly Arg Gly |
| 233 | His Val Glu Gly Thr Phe Thr Ser Asp Val Ser Ser Tyr Leu Glu Gly Gln Ala Ala Lys Ala Phe Ile Ala Trp Leu Val Lys Gly Arg Gly |
| 234 | His Val Glu Gly Thr Phe Thr Ser Asp Val Ser Ser Tyr Leu Glu Gly Gln Ala Ala Lys Glu Phe Ile Glu Trp Leu Val Lys Gly Arg Gly |
| 235 | His Gly Glu Gly Thr Phe Thr Ser Asp Val Ser Ser Tyr Leu Glu Gly Gln Ala Ala Lys Glu Phe Ile Glu Trp Leu Val Lys Gly Arg Gly |
| 236 | His Val Glu Gly Thr Phe Thr Ser Asp Val Ser Ser Tyr Leu Glu Gly Gln Ala Ala Lys Glu Phe Ile Ala Trp Leu Val Lys His Arg Gly |
| 237 | His Val Glu Gly Thr Phe Thr Ser Asp Val Ser Ser Tyr Leu Glu Gly Gln Ala Ala Lys Glu Phe Ile Ala Trp Leu Val Lys Gly Arg His |
| 238 | His Val Glu Gly Thr Phe Thr Ser Asp Val Ser Ser Tyr Leu Glu Glu Lys Ala Ala Lys Glu Phe Ile Ala Trp Leu Val Lys Gly Arg Gly |
| 239 | His Val Glu Gly Thr Phe Thr Ser Asp Val Ser Ser Tyr Leu Glu Glu Glu Ala Ala Lys Glu Phe Ile Ala Trp Leu Val Lys Gly Arg Gly |
| 240 | His Val Glu Gly Thr Phe Thr Ser Asp Val Ser Ser Tyr Leu Glu Glu Gln Ala Ala Lys Ala Phe Ile Ala Trp Leu Val Lys Gly Arg Gly |
| 241 | His Val Glu Gly Thr Phe Thr Ser Asp Val Ser Ser Tyr Leu Glu Gly Gln Ala Ala Lys Glu Phe Ile Ala Trp Leu Val Gly Lys Arg Gly |
| 242 | His Val Glu Gly Thr Phe Thr Ser Asp Val Ser Ser Tyr Leu Glu Gly Gln Ala Ala Lys Glu Phe Ile Ala Trp Leu Val Lys Gly Arg His |
| 243 | His Gly Glu Gly Thr Phe Thr Ser Asp Val Ser Ser Tyr Leu Glu Gly Gln Ala Ala Lys Glu Phe Ile Ala Trp Leu Val Lys Gly Arg His |

In further embodiments, the bioactive peptide or pritein of the compositions disclosed herein comprise amylin, amylin analogs and amylin deriviatives. Any amylin, amylin analogs or amylin deriviatives known in the art can be used in the present compositions, including, but not limited to those disclosed in U.S. Pat. Nos. 6,610,824, 5,686,411, 5,580,953, 5,367,052 and 5,124,314, all of which are incorporated herein by reference in their entireties and in particular the amylin-related sequences described therein. Examples of amylin peptides that may be used are described by the following formula:

Formula VIII (SEQ ID NO.248)
$A_1$-X-Asn-Thr-Ala-Thr-Y-Ala-Thr-Gln-Arg-Leu-$B_1$-Asn-Phe-Leu-$C_1$-$D_1$-$E_1$-$F_1$-$G_1$-Asn-$H_1$-Gly-$I_1$-$J_1$-Leu-$K_1$-$L_1$-Thr-$M_1$-Val-Gly-Ser-Asn-Thr-Tyr-Z, where:
$A_1$ is Lys, Ala, Ser or hydrogen,
$B_1$ is Ala, Set or Thr;
$C_1$ is Val, Leu or Ile;
$D_1$ is His or Arg;
$E_1$ is Ser or Thr;
$F_1$ is Ser, Thr, Gln or Asn;
$G_1$ is Asn, Gln or His;
$H_1$ is Phe, Leu or Tyr;
$I_1$ is Ala or Pro;
$J_1$ is Ile, Val, Ala or Leu;
$K_1$ is Ser, Pro, Leu, Ile or Thr;
$L_1$ is Ser, Pro or Thr;
$M_1$ is Asn, Asp, or Gln;

X and Y are independently selected amino acid residues having side chains which are chemically bonded to each other to form an intramolecular linkage; and Z is amino, alkylamino, dialkylamino, cycloalkylamino, arylamino, aralkylamino, alkyloxy, aryloxy or aralkyloxy. Particular, but non-limiting examples of amylin analogs and derivatives that can be used are presented in Table 4.

TABLE 4

| SEQ ID NO | Sequence |
|---|---|
| 249 | Lys Cys Asn Thr Ala Thr Cys Ala Thr Gln Arg Leu Ala Asn Phe Leu Val His Ser Ser Asn Asn Phe Gly Ala Ile Leu Ser Ser Thr Asn Val Gly Ser Asn Thr Tyr |
| 250 | Lys Cys Asn Thr Ala Thr Cys Ala Thr Gln Arg Leu Ala Asn Phe Leu Ile Arg Ser Ser Asn Asn Leu Gly Ala Ile Leu Ser Pro Thr Asn Val Gly Ser Asn Thr Tyr |
| 251 | Lys Cys Asn Thr Ala Thr Cys Ala Thr Gln Arg Leu Ala Asn Phe Leu Val Arg Thr Ser Asn Asn Leu Gly Ala Ile Leu Ser Pro Thr Asn Val Gly Ser Asn Thr Tyr |
| 252 | Lys Cys Asn Thr Ala Thr Cys Ala Thr Gln Arg Leu Ala Asn Phe Leu Val Arg Ser Ser Asn Asn Leu Gly Pro Val Leu Pro Pro Thr Asn Val Gly Ser Asn Thr Tyr |
| 253 | Lys Cys Asn Thr Ala Thr Cys Ala Thr Gln Arg Leu Ala Asn Phe Leu Val His Ser Asn Asn Asn Leu Gly Pro Val Leu Ser Pro Thr Asn Val Gly Ser Asn Thr Tyr |
| 254 | Lys Cys Asn Thr Ala Thr Cys Ala Thr Gln Arg Leu Thr Asn Phe Leu Val Arg Ser Ser His Asn Leu Gly Ala Ala Leu Leu Pro Thr Asp Val Gly Ser Asn Thr Tyr |
| 255 | Cys Asn Thr Ala Thr Cys Ala Thr Gln Arg Leu Ala Asn Phe Leu Val His Ser Ser Asn Asn Phe Gly Ala Ile Leu Ser Ser Thr Asn Val Gly Ser Asn Thr Tyr |
| 256 | Lys Cys Asn Thr Ala Thr Cys Ala Thr Gln Arg Leu Ala Asn Phe Leu Val His Ser Ser Asn Asn Phe Gly Ala Ile Leu Pro Ser Thr Asn Val Gly Ser Asn Thr Tyr |
| 257 | Lys Cys Asn Thr Ala Thr Cys Ala Thr Gln Arg Leu Ala Asn Phe Leu Val His Ser Ser Asn Asn Phe Gly Pro Ile Leu Pro Pro Thr Asn Val Gly Ser Asn Thr Tyr |
| 258 | Lys Cys Asn Thr Ala Thr Cys Ala Thr Gln Arg Leu Ala Asn Phe Leu Val Arg Ser Ser Asn Asn Phe Gly Pro Ile Leu Pro Ser Thr Asn Val Gly Ser Asn Thr Tyr |
| 259 | Cys Asn Thr Ala Thr Cys Ala Thr Gln Arg Leu Ala Asn Phe Leu Val His Arg Ser Asn Asn Phe Gly Pro Ile Leu Pro Ser Thr Asn Val Gly Ser Asn Thr Tyr |
| 260 | Lys Cys Asn Thr Ala Thr Cys Ala Thr Gln Arg Leu Ala Asn Phe Leu Val His Ser Ser Asn Asn Phe Gly Pro Val Leu Pro Pro Thr Asn Val Gly Ser Asn Thr Tyr |
| 261 | Lys Cys Asn Thr Ala Thr Cys Ala Thr Gln Arg Leu Ala Asn Phe Leu Val Arg Ser Ser Asn Asn Phe Gly Pro Ile Leu Pro Pro Thr Asn Val Gly Ser Asn Thr Tyr |
| 262 | Cys Asn Thr Ala Thr Cys Ala Thr Gln Arg Leu Ala Asn Phe Leu Val Arg Ser Ser Asn Asn Phe Gly Pro Ile Leu Pro Pro Ser Asn Val Gly Ser Asn Thr Tyr |
| 263 | Cys Asn Thr Ala Thr Cys Ala Thr Gln Arg Leu Ala Asn Phe Leu Val His Ser Ser Asn Asn Phe Gly Pro Ile Leu Pro Pro Ser Asn Val Gly Ser Asn Thr Tyr |
| 264 | Lys Cys Asn Thr Ala Thr Cys Ala Thr Gln Arg Leu Ala Asn Phe Leu Val His Ser Ser Asn Asn Leu Gly Pro Val Leu Pro Pro Thr Asn Val Gly Ser Asn Thr Tyr |
| 265 | Lys Cys Asn Thr Ala Thr Cys Ala Thr Gln Arg Leu Ala Asn Phe Leu Val His Ser Ser Asn Asn Leu Gly Pro Val Leu Pro Ser Thr Asn Val Gly Ser Asn Thr Tyr |
| 266 | Cys Asn Thr Ala Thr Cys Ala Thr Gln Arg Leu Ala Asn Phe Leu Val His Ser Ser Asn Asn Leu Gly Pro Val Leu Pro Ser Thr Asn Val Gly Ser Asn Thr Tyr |
| 267 | Lys Cys Asn Thr Ala Thr Cys Ala Thr Gln Arg Leu Ala Asn Phe Leu Val Arg Ser Ser Asn Asn Leu Gly Pro Val Leu Pro Ser Thr Asn Val Gly Ser Asn Thr Tyr |
| 268 | Lys Cys Asn Thr Ala Thr Cys Ala Thr Gln Arg Leu Ala Asn Phe Leu Val Arg Ser Ser Asn Asn Leu Gly Pro Ile Leu Pro Pro Thr Asn Val Gly Ser Asn Thr Tyr |
| 269 | Lys Cys Asn Thr Ala Thr Cys Ala Thr Gln Arg Leu Ala Asn Phe Leu Val Arg Ser Ser Asn Asn Leu Gly Pro Ile Leu Pro Ser Thr Asn Val Gly Ser Asn Thr Tyr |
| 270 | Lys Cys Asn Thr Ala Thr Cys Ala Thr Gln Arg Leu Ala Asn Phe Leu Ile His Ser Ser Asn Asn Leu Gly Pro Ile Leu Pro Pro Thr Asn Val Gly Ser Asn Thr Tyr |
| 271 | Lys Cys Asn Thr Ala Thr Cys Ala Thr Gln Arg Leu Ala Asn Phe Leu Val Ile Ser Ser Asn Asn Phe Gly Pro Ile Leu Pro Pro Thr Asn Val Gly Ser Asn Thr Tyr |
| 272 | Cys Asn Thr Ala Thr Cys Ala Thr Gln Arg Leu Ala Asn Phe Leu Ile His Ser Ser Asn Asn Leu Gly Pro Ile Leu Pro Pro Thr Asn Val Gly Ser AsnThr Tyr |
| 273 | Lys Cys Asn Thr Ala Thr Cys Ala Thr Gln Arg Leu Ala Asn Phe Leu Ile Arg Ser Ser Asn Asn Leu Gly Ala Ile Leu Ser Ser Thr Asn Val Gly Ser Asn Thr Tyr |

TABLE 4-continued

| SEQ ID NO | Sequence |
|---|---|
| 274 | Lys Cys Asn Thr Ala Thr Cys Ala Thr Gln Arg Leu Ala Asn Phe Leu Ile Arg Ser Ser Asn Asn Leu Gly Ala Val Leu Ser Pro Thr Asn Val Gly Ser Asn Thr Tyr |
| 275 | Lys Cys Asn Thr Ala Thr Cys Ala Thr Gln Arg Leu Ala Asn Phe Leu Ile Arg Ser Ser Asn Asn Leu Gly Pro Val Leu Pro Pro Thr Asn Val Gly Ser Asn Thr Tyr |
| 276 | Lys Cys Asn Thr Ala Thr Cys Ala Thr Gln Arg Leu Thr Asn Phe Leu Val His Ser Ser His Asn Leu Gly Ala Ala Leu Leu Pro Thr Asp Val Gly Ser Asn Thr Tyr |
| 277 | Lys Cys Asn Thr Ala Thr Cys Ala Thr Gln Arg Leu Thr Asn Phe Leu Val His Ser Ser His Asn Leu Gly Ala Ala Leu Ser Pro Thr Asp Val Gly Ser Asn Thr Tyr |
| 278 | Cys Asn Thr Ala Thr Cys Ala Thr Gln Arg Leu Thr Asn Phe Leu Val His Ser Ser His Asn Leu Gly Ala Val Leu Pro Ser Thr Asp Val Gly Ser Asn Thr Tyr |
| 279 | Lys Cys Asn Thr Ala Thr Cys Ala Thr Gln Arg Leu Thr Asn Phe Leu Val Arg Ser Ser His Asn Leu Gly Ala Ala Leu Ser Pro Thr Asp Val Gly Ser Asn Thr Tyr |
| 280 | Lys Cys Asn Thr Ala Thr Cys Ala Thr Gln Arg Leu Thr Asn Phe Leu Val Arg Ser Ser His Asn Leu Gly Ala Ile Leu Pro Pro Thr Asp Val Gly Ser Asn Thr Tyr |
| 281 | Lys Cys Asn Thr Ala Thr Cys Ala Thr Gln Arg Leu Thr Asn Phe Leu Val Arg Ser Ser His Asn Leu Gly Pro Ala Leu Pro Pro Thr Asp Val Gly Ser Asn Thr Tyr |
| 282 | Lys Asp Asn Thr Ala Thr Lys Ala Thr Gln Arg Leu Ala Asn Phe Leu Val His Ser Ser Asn Asn Phe Gly Ala Ile Leu Ser Ser Thr Asn Val Gly Ser Asn Thr Tyr |
| 283 | Ala Cys Asn Thr Ala Thr Cys Ala Thr Gln Arg Leu Ala Asn Phe Leu Val His Ser Ser Asn Asn Phe Gly Ala Ile Leu Ser Ser Thr Asn Val Gly Ser Asn Thr Tyr |
| 284 | Ser Cys Asn Thr Ala Thr Cys Ala Thr Gln Arg Leu Ala Asn Phe Leu Val His Ser Ser Asn Asn Phe Gly Ala Ile Leu Ser Ser Thr Asn Val Gly Ser Asn Thr Tyr |
| 285 | Lys Cys Asn Thr Ala Thr Cys Ala Thr Gln Arg Leu Ala Asn Phe Leu Val His Ser Ser Asn Asn Phe Gly Ala Ile Leu Ser Pro Thr Asn Val Gly Ser Asn Thr Tyr |
| 286 | Lys Cys Asn Thr Ala Thr Cys Ala Thr Gln Arg Leu Ala Asn Phe Leu Val His Ser Ser Asn Asn Phe Gly Pro Ile Leu Pro Ser Thr Asn Val Gly Ser Asn Thr Tyr |
| 287 | Cys Asn Thr Ala Thr Cys Ala Thr Gln Arg Leu Ala Asn Phe Leu Val His Ser Ser Asn Asn Phe Gly Pro Ile Leu Pro Ser Thr Asn Val Gly Ser Asn Thr Tyr |
| 288 | Cys Asn Thr Ala Thr Cys Ala Thr Gln Arg Leu Ala Asn Phe Leu Val His Ser Ser Asn Asn Phe Gly Pro Val Leu Pro Pro Ser Asn Val Gly Ser Asn Thr Tyr |
| 289 | Lys Cys Asn Thr Ala Thr Cys Ala Thr Gln Arg Leu Ala Asn Phe Leu Val His Ser Ser Asn Asn Phe Gly Ala Ile Leu Ser Ser Thr Asn Val Gly Ser Asn Thr Tyr |
| 290 | Lys Cys Asn Thr Ala Thr Cys Ala Thr Gln Arg Leu Ala Asn Phe Leu Val His Ser Ser Asn Asn Phe Gly Pro Ile Leu Pro Pro Thr Asn Val Gly Ser Asn Thr Tyr |
| 291 | Lys Cys Asn Thr Ala Thr Cys Val Leu Gly Arg Leu Ser Gln Glu Leu His Arg Leu Gln Thr Tyr Pro Arg Thr Asn Thr Gly Ser Asn Thr Tyr NH$_2$ |
| 292 | Cys Ser Asn Leu Ser Thr Cys Val Leu Gly Arg Leu Ser Gln Glu Leu His Arg Leu Gln Thr Tyr Pro Arg Thr Asn Thr Gly Ser Asn Thr Tyr NH$_2$ |

Included in the compositions and methods disclosed herein are analogs and derivatives of bioactive peptides or proteins that have undergone one or more amino acid substitutions, additions or deletions. In one embodiment, the analog or derivative has undergone not more than 10 amino acid substitutions, deletions and/or additions. In another embodiment, the analog or derivative has undergone not more than 5 amino acid substitutions, deletions and/or additions.

Substitutions of amino acids within a peptide or protein while retaining at least one of the biological activities associated with the parent peptide or protein is known within the art of protein chemistry. It is recognized in the art that modifications in the amino acid sequence of a peptide, polypeptide, or protein can result in equivalent, or possibly improved, second generation peptides, etc., that display equivalent or superior functional characteristics when compared to the original amino acid sequence. Alterations can include amino acid insertions, deletions, substitutions, truncations, fusions, shuffling of subunit sequences, and the like.

One factor that can be considered in making such changes is the hydropathic index of amino acids. The importance of the hydropathic amino acid index in conferring interactive biological function on a protein has been discussed by Kyte and Doolittle (*J. Mol. Biol.*, 157: 105-132, 1982). It is accepted that the relative hydropathic character of amino acids contributes to the secondary structure of the resultant protein.

Based on its hydrophobicity and charge characteristics, each amino acid has been assigned a hydropathic index as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate/glutamine/aspartate/asparagine (−3.5); lysine (−3.9); and arginine (−4.5).

As is known in the art, certain amino acids in a peptide or protein can be substituted for other amino acids having a similar hydropathic index or score and produce a resultant peptide or protein having similar biological activity, i.e., which still retains biological functionality. In making such changes, it is preferable that amino acids having hydropathic indices within ±2 are substituted for one another. More preferred substitutions are those wherein the amino acids have hydropathic indices within ±1. Most preferred substitutions are those wherein the amino acids have hydropathic indices within ±0.5.

Like amino acids can also be substituted on the basis of hydrophilicity. U.S. Pat. No. 4,554,101 discloses that the greatest local average hydrophilicity of a protein, as governed by the hydrophilicity of its adjacent amino acids, correlates with a biological property of the protein. The following hydrophilicity values have been assigned to amino acids: arginine/lysine (+3.0); aspartate/glutamate (+3.0±1); serine (+0.3); asparagine/glutamine (+0.2); glycine (0); threonine (−0.4); proline (−0.5±1); alanine/histidine (−0.5); cysteine (−1.0); methionine (−1.3); valine (−1.5); leucine/isoleucine (−1.8); tyrosine (−2.3); phenylalanine (−2.5); and tryptophan (−3.4). Thus, one amino acid in a peptide, polypeptide, or protein can be substituted by another amino acid having a similar hydrophilicity score and still produce a resultant protein having similar biological activity, i.e., still retaining correct biological function. In making such changes, amino acids having hydrophilicity values within ±2 are preferably substituted for one another, those within ±1 are more preferred, and those within ±0.5 are most preferred.

As outlined above, amino acid substitutions in the bioactive peptides and proteins for use in the compositions and methods disclosed herein can be based on the relative similarity of the amino acid side-chain substituents, for example, their hydrophobicity, hydrophilicity, charge, size, etc. Exemplary substitutions that take various of the foregoing characteristics into consideration in order to produce conservative amino acid changes resulting in silent changes can be selected from other members of the class to which the naturally occurring amino acid belongs. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine, and glutamine; and (4) neutral non-polar amino acids such as alanine, leucine, isoleucine, valine, proline, phenylalanine, tryptophan, and methionine. It should be noted that changes which are not expected to be advantageous can also be useful if these result in the production of functional sequences.

Also included within the scope of the bioactive peptides and proteins that can be used in the present compositions are conjugates of the above referenced proteins, peptides and peptide analogs, e.g., chemically modified with or linked to at least one molecular weight enhancing compound known in the art such as polyethylene glycol, and chemically modified equivalents of such proteins, peptides, analogs, or conjugates. The polyethylene glycol polymers may have molecular weights between about 500 Da and 20,000 Da. Preferred conjugates include those described in International Patent Publication No. WO 00/66629, which is herein incorporated by reference in its entirety. In one embodiment, the bioactive peptides and proteins of the invention have a molecular weight up to about 100,000 Da, in another embodiment up to about 25,000 Da, while in still another embodiment up to about 5,000 Da.

As used herein, the terms "protein" or "peptide" include any molecule that comprises five or more amino acids. It is well known in the art that proteins may undergo modification, including post-translational modifications, such as, but not limited to, disulfide bond formation, glycosylation, phosphorylation, or oligomerization. Thus, as used herein, the term "protein" or "peptide" includes any protein or peptide that is modified by any biological or non-biological process.

The term "amino acid" is used in its broadest sense, and includes naturally occurring amino acids as well as non-naturally occurring amino acids, including amino acid analogs and derivatives. The latter includes molecules containing an amino acid moiety. One skilled in the art will recognize, in view of this broad definition, that reference herein to an amino acid includes, for example, naturally occurring proteogenic L-amino acids; D-amino acids; chemically modified amino acids such as amino acid analogs and derivatives; naturally occurring non-proteogenic amino acids such as norleucine, β-alanine, ornithine, norvaline, homocysteine, homoserine etc.; and chemically synthesized compounds having properties known in the art to be characteristic of amino acids. As used herein, the term "proteogenic" indicates that the amino acid can be incorporated into a peptide, polypeptide, or protein in a cell through a metabolic pathway.

The term "polyamino acid" refers to any homopolymer or mixture of homopolymers of a particular amino acid.

As used herein in reference to a peptide or protein, the term "derivative" means a protein or peptide that is obtained by modification of a parent protein or peptide, for example, by amino acid substitution, addition or deletion. In one embodiment, derivatives have at least 15% sequence identity to the parent molecule. In other embodiments, derivatives have at least 50%, at least 70%, at least 80%, at least 90% or at least 95% sequence identity with the parental protein or peptide.

As used herein "analog" refers to bioactive peptides or proteins that are structurally related to a parent peptide or protein by amino acid sequence but which differ from the parent in a characteristic of interest such as bioactivity, solubility, resistance to proteolysis, etc. In certain embodiments, analogs have activities between about 1% to about 10,000%, about 10% to about 1000%, and about 50% to about 500% of the bioactivity of the parental protein or peptide.

The term "bioactive" or "bioactivity" means the ability to affect any physical or biochemical properties of a biological organism, including but not limited to viruses, bacteria, fungi, plants, animals, and humans. In particular, as used herein, bioactive includes diagnosis, cure, mitigation, treatment, or prevention of disease in humans or other animals, or to otherwise enhance physical or mental well-being of humans or animals.

As used herein "subject" or "patient" refers to any animal including domestic animals such as domestic livestock and companion animals. The terms are also meant to include human beings.

The cationic polyamino acids of the invention include polymers of basic amino acids, such as histidine, arginine, and lysine, that are protonated in a neutral or acidic pH environment and are thus cationic. The molecular weight of such polymers, e.g., poly-L-histidine, poly-L-arginine, poly-L-lysine, or copolymers thereof, are generally between about 10 and about 200 kDa. In another embodiment, the polymers have an average molecular weight of between about 100 kDa and about 200 kDa. In still a further embodiment, the polymers have an average molecular weight between about 140 kDa and about 150 kDa, while in yet another embodiment the polymers have an average molecular weight of between about 140 kDa and about 200 kDa. In one particular embodiment the cationic polyamino acid of the composition is poly-L-arginine hydrochloride with an average molecular weight of about 141 kDa.

Buffers useful in connection with the compositions and methods disclosed herein can be any buffer that displays adequate buffering capacity (buffer value) at the pH ranges which render the bioactive peptides and proteins of the invention chemically stable for the duration of use, and which are physically compatible with the cationic polyamino acids of the invention at the concentrations and pHs of use, i.e., they do not cause precipitation of the cationic polyamino acid. Methods for calculating the buffering capacity (buffer value) of a buffer at a particular concentration and pH are well known in the art and can be determined by the skilled artisan without undue experimentation.

It has been found that traditional buffer components with multi-anionic charges such as citric acid generally are not physically compatible with the cationic polyamino acids of the invention, resulting in precipitation of the polyamino acid. However, buffer components containing neutral and mono-anionic net charges are compatible with, and can be used in combination with the cationic polyamino acids of the invention. Examples of suitable buffers include, but are not limited to acetic acid, $\epsilon$-aminocaproic acid, and glutamic acid.

The pharmaceutical compositions of the invention may further comprise any number of known pharmaceutically acceptable excipients such as, but not limited to, tonicifying agents, viscosity-increasing agents, bioadhesive agents, preservatives, diluents, carriers, and the like.

Examples of tonicifying agents that may be used, include, but are not limited to, sodium chloride, mannitol, sucrose, and glucose. However, any tonicifying agent known in the art to prevent mucosal irritation can be used.

Exemplary viscosity-increasing and bioadhesive agents that may be used in the compositions disclosed herein, include, but are not limited to, cellulose derivatives (e.g., hydroxypropyl cellulose, hydroxypropyl methylcellulose or methylcellulose of average molecular weight between 10 and 1,500 kDa), starch, gums, carbomers, and polycarbophil. However, any viscosity-increasing or bioadhesive agents known in the art to afford a higher viscosity or to increase the residence time of the pharmaceutical composition at the absorption site may be used.

With the availability of preservative-free spray systems to the pharmaceutical industry, the incorporation of preservative(s) becomes optional in the composition of this invention. Should a preservative system be required or desired, preservative(s) may be added such as phenylethyl alcohol, methylparaben, ethylparaben, propylparaben, butylparaben, chlorbutanol, benzoic acid, sorbic acid, phenol, m-cresol and alcohol.

The compositions of the present invention can further comprise aqueous carriers, non-aqueous carriers or suspension media. For instance, the pharmaceutical compositions of the invention may be formulated as an aqueous solution in purified water, or may be dispersed in non-aqueous media to thereby be compatible with aerosolization or delivery by instillation in non-aqueous suspension media. By way of example, such non-aqueous suspension media can include hydrofluoroalkanes, fluorocarbons, perfluorocarbons, fluorocarbon/hydrocarbon diblocks, hydrocarbons, alcohols, ethers, and combinations thereof. However, it is understood that any non-aqueous suspension media known in the art may be used in conjunction with the compositions and method disclosed herein.

As mentioned above, the pharmaceutical compositions of the invention may be formulated in a variety of dosage forms suitable for transmucosal delivery, as known in the art. For instance, the compositions may be formulated as an aqueous solution or suspension, a non-aqueous solution or suspension, a tablet, or a dry powder. In any event, the compositions of the invention will generally comprise a therapeutically or prophylactically effective amount of a bioactive peptide or protein and an absorption enhancing amount of a mixture comprising a cationic polyamino acid and a buffer that is compatible with the cationic polyamino acid.

One embodiment provides a pharmaceutical composition for nasal delivery in the form of an aqueous solution with enhanced transmucosal absorption, wherein the pharmaceutical composition includes a bioactive peptide or protein; an absorption enhancing cationic polyamino acid; a buffer that is compatible with said cationic polyamino acid; and a bioadhesive agent. Another embodiment of the invention provides a pharmaceutical composition for sublingual delivery in the form of a tablet.

In one embodiment, the weight ratio of bioactive peptide or protein to cationic polyamino acid in the final formulation ranges from 1:100 to 100:1, in another embodiment from 1:25 to 25:1, in yet another embodiment from 1:10 to 10:1, and in still yet another embodiment from 1:2 to 2:1.

The weight ratio of cationic polyamino acid to buffer can vary widely and may be determined by routine experimentation. The only limitation is that adequate buffer is included such that the cationic polyamino acid does not precipitate in the formulated dosage form or upon administration to the desired mucous membrane. In one embodiment the useful weight ratios of cationic polyamino acid to buffer range from 1:100 to 100:1, while in another embodiment the weight ratio of cationic polyamino acid to buffer ranges from 1:25 to 25:1. In other embodiments, the weight ratio of cationic polyamino acid to buffer ranges from 1:10 to 10:1, and from 1:2 to 2:1

When formulated as an aqueous solution, the instant pharmaceutical compositions may comprise: 0.01%-5.0% (w/v) of the bioactive peptide or protein; 0.01%-1.0% (w/v) of the cationic polyamino acid; 0.01%-10.0% (w/v) of the buffer; 0.001%-10.0% (w/v) of the optional tonicifying agent; 0.001%-10.0% (w/v) of the optional viscosity-increasing agent; 0.001%-10.0% (w/v) of the optional bioadhesive agent; 0.001%-10.0% (w/v) of the optional preservative; q.s. (quantum sufficiat) to 100.0% (w/v) of purified water;

The term "therapeutically or prophylactically effective amount" as used herein refers to an amount of a bioactive peptide or protein to treat, ameliorate, or prevent a disease or condition of interest, or to exhibit a detectable therapeutic or preventative effect. The effect can be detected by, for example, a reduction of plasma glucose or $HbA_{1c}$ levels, or reduction or maintenance of body weight. Therapeutic effects also include reduction in physical symptoms. The precise effective amount for a subject will depend upon the subject's size and health, the nature and extent of the condition, and the therapeutics or combination of therapeutics selected for administration. Generally, the effective amount for a given situation can be determined by routine experimentation and is within the judgement of the clinician.

The exact dosage will be determined by the practitioner, in light of factors related to the subject that requires treatment. Dosage and administration are adjusted to provide sufficient levels of the active moiety or to maintain the desired effect. Factors that may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the active ingredient in the particular formulation.

For any compound, the therapeutically effective dose can be estimated initially either in cell culture assays, e.g., of neoplastic cells, or in animal models, usually mice, rats, rabbits, dogs, or pigs. The animal model may also be used to determine the appropriate concentration range and route of administration. Such information can then be used to determine useful doses and routes for administration in humans. Further, therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration.

The term "absorption enhancing amount" as used herein refers to an amount of the absorption enhancing mixture such that the transmucosal absorption of the bioactive peptide or protein is enhanced by at least 2-fold, at least 5-fold, or at least 10-fold, as compared to transmucosal absorption of the bioactive peptide or protein in the absence or substantial absence of the absorption enhancing mixture. Generally, an effective absorption enhancing amount for a given situation can be determined by routine experimentation.

In one embodiment, the pharmaceutical composition is formulated as an aqueous solution and includes: exendin-4; poly-L-arginine of average molecular weight between 10 and 200 kDa; glutamate buffer at pH between 4.0 and 5.0; sodium chloride; and purified water. In another embodiment, the pharmaceutical composition includes: exendin-4; poly-L-arginine of average molecular weight between 10 and 200 kDa; glutamate buffer at pH between 4.0 and 5.0; sodium chloride; hydroxypropyl methylcellulose of average molecular weight between 10 kDa and 1,500 kDa; and purified water.

In a further embodiment, the pharmaceutical composition may include exendin-4 at a concentration between 0.01% and 5.0% (w/v); poly-L-arginine of average molecular weight between 10 kDa and 200 kDa at a concentration between 0.01% and 1.0% (w/v); glutamate buffer at pH between 4.0 and 5.0 at a concentration between 0.01% and 10.0% (w/v); sodium chloride at a concentration between 0.001% and 0.9% (w/v); and purified water to 100%.

In another embodiment, the pharmaceutical composition includes exendin-4 at a concentration between 0.01% and 5.0% (w/v); poly-L-arginine of average molecular weight between 10 kDa and 200 kDa at a concentration between 0.01% and 1.0% (w/v); glutamate buffer at pH between 4.0 and 5.0 at a concentration between 0.01% and 10.0% (w/v); sodium chloride at a concentration between 0.001% and 0.9% (w/v); hydroxypropyl methylcellulose of average molecular weight 10 kDa and 1,500 kDa at a concentration between 0.001% and 10.0% (w/v); and purified water to make 100%.

In yet another embodiment of the invention, the pharmaceutical composition includes exendin-4 at a concentration of 0.5% to 1.0% (w/v); poly-L-arginine hydrochloride of average molecular weight 141 kDa at a concentration of 0.5% (w/v); glutamate buffer at pH 4.5 at a concentration of 0.56% (w/v); sodium chloride at a concentration of 0.72% (w/v); and purified water to 100%.

In another embodiment, the pharmaceutical composition of the invention may include exendin-4 at a concentration of 0.5% to 1.0% (w/v); poly-L-arginine hydrochloride of average molecular weight of 141 kDa at a concentration of 0.5% (w/v); glutamate buffer at pH of 4.5 at a concentration of 0.56% (w/v); sodium chloride at a concentration of 0.72% (w/v); hydroxypropyl methylcellulose of average molecular weight ranging from about 4 to about 86 kDa at a concentration 0.5% (w/v); and purified water to 100%.

In one aspect of the invention, the compositions disclosed herein can be formulated for transmucosal delivery to or via the mucous membranes of a patient in need of treatment. Such formulations can be delivered to or via the mucous membranes for prophylactic or therapeutic purposes in any manner known in the art such as, but not limited to, drops, sprays, tablets, dry-powder inhalation, instillation, metered dose inhalation, nebulization, aerosolization, or instillation as suspension in compatible vehicles. More particularly, ocular, nasal, pulmonary, buccal, sublingual, rectal, or vaginal administration is contemplated as within the scope of the invention.

In one embodiment, the pharmaceutical composition may be administered as an aqueous solution in the form of drops or a spray. In another embodiment, the pharmaceutical composition disclosed herein may be administered as a dry powder formulation. In yet another embodiment, the pharmaceutical composition may be administered as a tablet formulation, wherein the tablet preferably comprises a bioadhesive agent.

The compositions disclosed herein may also be administered via aerosolization, such as with a dry powder inhaler (DPI), metered dose inhaler (MDI), liquid dose instillation (LDI), and nebulizers. DPIs, MDIs, LDIs, and nebulizers are all well known in the art and could easily be employed for administration of the pharmaceutical compositions of the invention without undue experimentation.

In another aspect, a method for enhancing the transmucosal absorption of a bioactive peptide or protein is provided, wherein the method involves administering the bioactive peptide or protein to a subject via a mucous membrane in conjunction with an absorption enhancing composition comprising a cationic polyamino acid and a buffer that is compatible with that cationic polyamino acid.

Generally stated, the transmucosal absorption of the bioactive peptide or protein is enhanced relative to the transmucosal absorption of the bioactive peptide or protein in the absence or substantial absence of the absorption enhancing composition comprising a cationic polyamino acid. In one embodiment, the transmucosal absorption of the bioactive peptide or protein is improved by at least 2-fold, in another embodiment at least 5-fold, and in still another embodiment by at least 10-fold over the transmucosal absorption of the bioactive peptide or protein when administered to a subject via transmucosal delivery in the absence or the substantial absence of the absorption enhancing composition.

In one embodiment, the bioactive peptide or protein is administered as an aqueous solution comprising the absorption enhancing composition. In another embodiment, the bioactive peptide or protein is administered as a dry powder formulation comprising the absorption enhancing composition. In yet another embodiment, the bioactive peptide or protein is administered as a tablet formulation comprising the absorption enhancing composition, wherein the absorption enhancing composition optionally further comprises a bioadhesive agent.

Another aspect relates to a method for improving the bioavailability of a bioactive peptide or protein administered to a subject via transmucosal delivery, wherein the method generally involves administering the bioactive peptide or protein to a subject via a mucous membrane in conjunction with an absorption enhancing composition comprising a cationic polyamino acid and a buffer that is compatible with that cationic polyamino acid. According to one embodiment of the method, the bioavailability of the bioactive peptide or protein is improved by at least 2-fold, in another embodiment of the invention at least 5-fold, and in yet another embodiment of the method by at least 10-fold over the bioavailability of the bioactive peptide or protein when administered to a subject via transmucosal delivery in the absence or substantial absence of the absorption enhancing composition.

The following examples are intended to provide illustrations of the application of the present invention. The following examples are not intended to completely define or otherwise limit the scope of the invention.

EXAMPLES

The peptide exendin-4 (AC2993) is useful as a model for peptides or proteins with iso-electric points that lend themselves (or can be buffered) to have either neutral or positive net charges within the pH range from about 4 to about 7 for optimum transmucosal delivery.

Example 1

An aqueous pharmaceutical composition was prepared as follows: 0.5% weight by volume of exendin-4; 0.5% weight by volume of poly-L-arginine hydrochloride of average molecular weight 141 kDa; 0.56% weight by volume of monosodium glutamate, monohydrate; 0.72% weight by volume of sodium chloride; hydrochloric acid q.s. to adjust the pH to approximately 4.5; q.s. to 100.0% weight by volume of water.

Example 2

An aqueous pharmaceutical composition was prepared as follows: 0.5% weight by volume of exendin-4; 0.25% weight by volume of poly-L-arginine hydrochloride of average molecular weight 141 kDa; 0.56% weight by volume of monosodium glutamate, monohydrate; 0.72% weight by volume of sodium chloride; hydrochloric acid q.s. to adjust the pH to approximately 4.5; q.s. to 100.0% weight by volume of water.

Example 3

An aqueous pharmaceutical composition was prepared as follows: 0.5% weight by volume of exendin-4; 0.5% weight by volume of poly-L-arginine hydrochloride of average molecular weight 141 kDa; 0.56% weight by volume of monosodium glutamate, monohydrate; 0.72% weight by volume of sodium chloride; 0.5% weight by volume of hydroxypropyl methylcellulose of average molecular weight approximately 86 kDa; hydrochloric acid q.s. to adjust the pH to approximately 4.5; q.s. to 100.0% weight by volume of water.

Example 4

Figure 2:
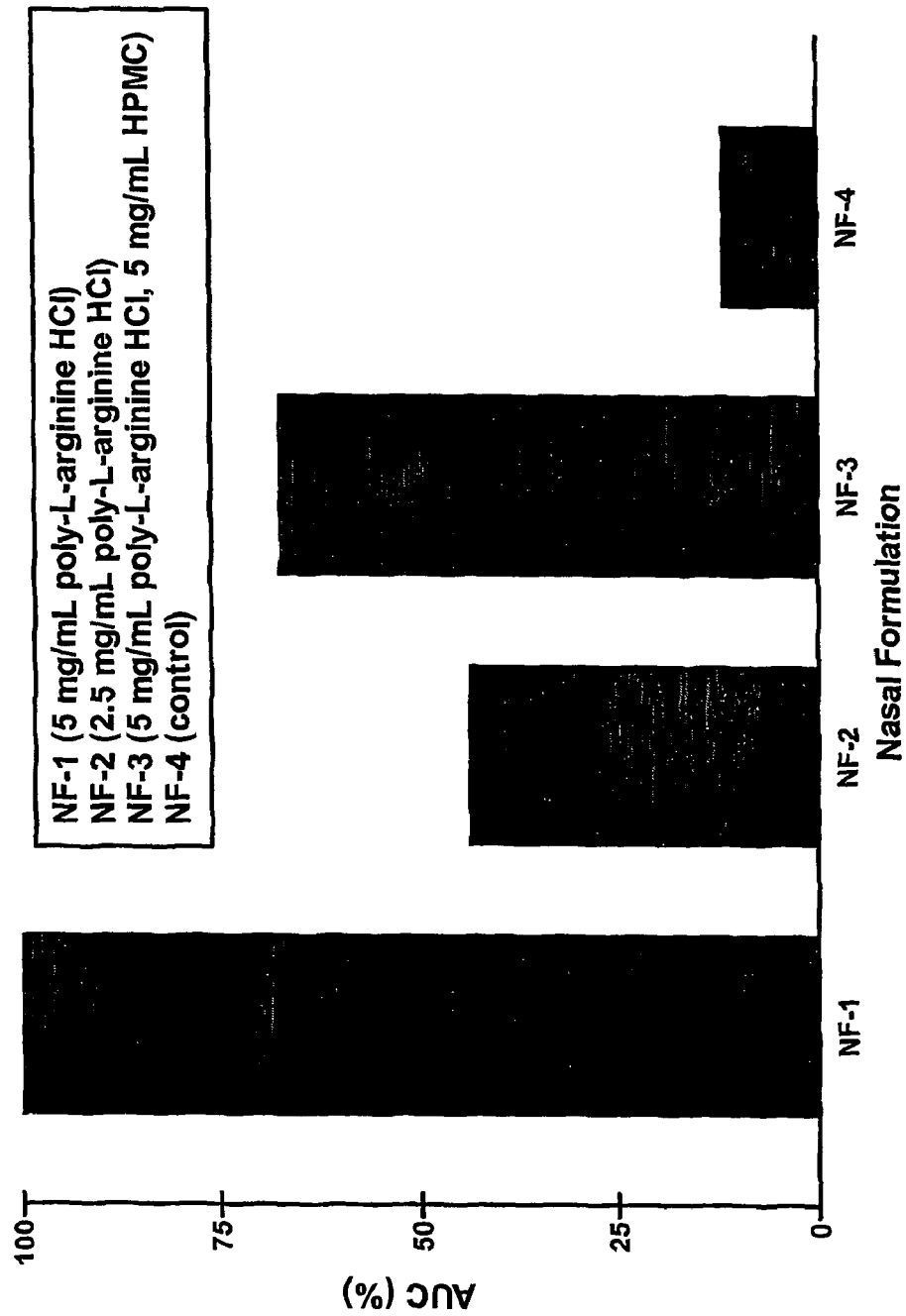
FIG. 2 depicts the area under the plasma curves (AUC) (0-8 hours) of exendin-4 nasal formulations relative to a formulation including 5 mg/mL poly-L-arginine (NF-1). NF-1, NF-2 and NF-3 are the compositions described in Examples 1, 2 and 3, respectively. NF-4 is a control formulation lacking poly-L-arginine.

To evaluate the efficacy of the transmucosal absorption enhancing ability of the cationic polyamino acids of the invention, the aqueous pharmaceutical compositions of Examples 1-3, and a control composition (prepared in the absence of the cationic polyamino acid) were prepared and nasally administered to Cynomolgus monkeys via a spray bottle. As depicted in FIGS. 1 and 2, the presence of a cationic polyamino acid (poly-L-arginine) showed a significant, concentration dependent effect on transmucosal absorption and bioavailability which was dependent on the concentration of the polyamino acid. More specifically, FIG. 1 depicts the bioavailability enhancement (normalized to a 1 µg/kg dose) of three exendin-4 aqueous solutions containing poly-L-arginine with or without hydroxypropyl methylcellulose as compared to a control exendin-4 solution without poly-L-arginine. FIG. 2 depicts the area under the plasma curves (AUC) up to 8 hours post-dosing of the exendin-4 solutions relative to the solution affording the highest bioavailability (NF-1). The data show that the AUC of the exendin-4 control solution without poly-L-arginine (NF-4) is approximately one-tenth of that of the solution containing 0.5% poly-L-arginine (NF-1). Thus, the bioavailability is unexpectedly enhanced 10-fold by the poly-L-arginine formulation.

CONCLUSION

In light of the detailed description of the invention and the examples presented above, it can be appreciated that the several aspects of the invention are achieved.

It is to be understood that the present invention has been described in detail by way of illustration and example in order to acquaint others skilled in the art with the invention, its principles, and its practical application. Particular formulations and processes of the present invention are not limited to the descriptions of the specific embodiments presented, but rather the descriptions and examples should be viewed in terms of the claims that follow and their equivalents. While some of the examples and descriptions above include some conclusions about the way the invention may function, the inventors do not intend to be bound by those conclusions and functions, but put them forth only as possible explanations.

It is to be further understood that the specific embodiments of the present invention as set forth are not intended as being exhaustive or limiting of the invention, and that many alternatives, modifications, and variations will be apparent to those of ordinary skill in the art in light of the foregoing examples and detailed description. Accordingly, this invention is intended to embrace all such alternatives, modifications, and variations that fall within the spirit and scope of the following claims.

What is claimed is:

1. A pharmaceutical composition for transmucosal administration comprising about 0.5% (w/v) of exendin-4; about 0.5% (w/v) of poly-arginine having an average molecular weight of about 141 kDa; and about 0.56% monosodium glutamate monohydrate (w/v), at a pH of about 4.5 and wherein the exendin-4 has the same net charge as the poly-arginine at the pH of the composition.

2. The composition of claim 1, wherein said poly-arginine is poly-L-arginine.

3. The composition of claim 1, wherein said composition further comprises a tonicifying agent, a viscosity-increasing agent, a bioadhesive agent, a preservative, or any combination thereof.

4. The composition of claim 1, further comprising about 0.72% sodium chloride (w/v).

5. A pharmaceutical composition for transmucosal administration comprising about 0.5% (w/v) of exendin-4; about 1.0% (w/v) of poly-arginine having an average molecular weight of about 141 kDa; and about 0.56% monosodium glutamate monohydrate (w/v), at a pH of about 4.5 and wherein the exendin-4 has the same net charge as the poly-arginine at the pH of the composition.

6. The composition of claim 5, wherein said poly-arginine is poly-L-arginine.

7. The composition of claim 5, wherein said composition further comprises a tonicifying agent, a viscosity-increasing agent, a bioadhesive agent, a preservative, or any combination thereof.

8. The composition of claim 5, further comprising about 0.72% sodium chloride (w/v).

* * * * *

SEQUENCE LISTING

<160> NUMBER OF SEQ ID NOS: 292

<210> SEQ ID NO 1
<211> LENGTH: 39
<212> TYPE: PRT
<213> ORGANISM: Heloderma horridum
<220> FEATURE:
<221> NAME/KEY: MOD_RES
<222> LOCATION: (39)..(39)
<223> OTHER INFORMATION: AMIDATION

<400> SEQUENCE: 1

His Ser Asp Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 39
<212> TYPE: PRT
<213> ORGANISM: Heloderma suspectum

<400> SEQUENCE: 2

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 3
<211> LENGTH: 39
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: (1)..(1)
<223> OTHER INFORMATION: His, Arg or Tyr
<220> FEATURE:
<221> NAME/KEY: VARIANT
<222> LOCATION: (2)..(2)
<223> OTHER INFORMATION: Ser, Gly, Ala or Thr
<220> FEATURE:
<221> NAME/KEY: VARIANT
<222> LOCATION: (3)..(3)
<223> OTHER INFORMATION: Asp or Glu
<220> FEATURE:
<221> NAME/KEY: VARIANT
<222> LOCATION: (6)..(6)
<223> OTHER INFORMATION: Phe, Thr or naphthylalanine
<220> FEATURE:
<221> NAME/KEY: VARIANT
<222> LOCATION: (7)..(7)
<223> OTHER INFORMATION: Thr or Ser
<220> FEATURE:
<221> NAME/KEY: VARIANT
<222> LOCATION: (8)..(8)
<223> OTHER INFORMATION: Ser or Thr
<220> FEATURE:
<221> NAME/KEY: VARIANT
<222> LOCATION: (9)..(9)
<223> OTHER INFORMATION: Asp or Glu
<220> FEATURE:
<221> NAME/KEY: VARIANT
<222> LOCATION: (10)..(10)

```
<223> OTHER INFORMATION: Leu, Ile, Val, pentylglycine or Met
<220> FEATURE:
<221> NAME/KEY: VARIANT
<222> LOCATION: (14)..(14)
<223> OTHER INFORMATION: Leu, Ile, pentylglycine, Val or Met
<220> FEATURE:
<221> NAME/KEY: VARIANT
<222> LOCATION: (22)..(22)
<223> OTHER INFORMATION: Phe, Tyr or napthtylalanine
<220> FEATURE:
<221> NAME/KEY: VARIANT
<222> LOCATION: (23)..(23)
<223> OTHER INFORMATION: Ile, Val, Leu, pentylglycine, t-butylglycine or
      Met
<220> FEATURE:
<221> NAME/KEY: VARIANT
<222> LOCATION: (24)..(24)
<223> OTHER INFORMATION: Glu or Asp
<220> FEATURE:
<221> NAME/KEY: VARIANT
<222> LOCATION: (25)..(25)
<223> OTHER INFORMATION: Trp, Phe, Tyr or naphthylalanine
<220> FEATURE:
<221> NAME/KEY: VARIANT
<222> LOCATION: (31)..(31)
<223> OTHER INFORMATION: Pro, homoproline, 3Hyp, 4Hyp, thioproline,
      N-alkylglycine, N-alkylpentylglycine, or N-alkylalanine
<220> FEATURE:
<221> NAME/KEY: VARIANT
<222> LOCATION: (36)..(38)
<223> OTHER INFORMATION: Pro, homoproline, 3Hyp, 4Hyp, thioproline,
      N-alkylglycine, N-alkylpentylglycine or N-alkylalanine
<220> FEATURE:
<221> NAME/KEY: VARIANT
<222> LOCATION: (39)..(39)
<223> OTHER INFORMATION: Optional amidation
<220> FEATURE:
<221> NAME/KEY: VARIANT
<222> LOCATION: (39)..(39)
<223> OTHER INFORMATION: Ser, Thr or Tyr

<400> SEQUENCE: 3

Xaa Xaa Xaa Gly Thr Xaa Xaa Xaa Xaa Xaa Ser Lys Gln Xaa Glu Glu
1               5                   10                  15

Glu Ala Val Arg Leu Xaa Xaa Xaa Xaa Leu Lys Asn Gly Gly Xaa Ser
            20                  25                  30

Ser Gly Ala Xaa Xaa Xaa Xaa
        35

<210> SEQ ID NO 4
<211> LENGTH: 38
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: (1)..(1)
<223> OTHER INFORMATION: His, Arg, or Tyr
<220> FEATURE:
<221> NAME/KEY: VARIANT
<222> LOCATION: (2)..(2)
<223> OTHER INFORMATION: Ser, Gly, Ala or Thr
<220> FEATURE:
<221> NAME/KEY: VARIANT
<222> LOCATION: (3)..(3)
<223> OTHER INFORMATION: Ala, Asp or Glu
<220> FEATURE:
<221> NAME/KEY: VARIANT
<222> LOCATION: (5)..(5)
<223> OTHER INFORMATION: Ala or Thr
<220> FEATURE:
<221> NAME/KEY: VARIANT
<222> LOCATION: (6)..(6)
<223> OTHER INFORMATION: Ala, Phe, Tyr or napthylalanine
<220> FEATURE:
```

-continued

```
<221> NAME/KEY: VARIANT
<222> LOCATION: (7)..(7)
<223> OTHER INFORMATION: Thr or Ser
<220> FEATURE:
<221> NAME/KEY: VARIANT
<222> LOCATION: (8)..(8)
<223> OTHER INFORMATION: Ala, Ser or Thr
<220> FEATURE:
<221> NAME/KEY: VARIANT
<222> LOCATION: (9)..(9)
<223> OTHER INFORMATION: Asp or Glu
<220> FEATURE:
<221> NAME/KEY: VARIANT
<222> LOCATION: (10)..(10)
<223> OTHER INFORMATION: Ala, Leu, Ile, Val, pentylglycine or Met
<220> FEATURE:
<221> NAME/KEY: VARIANT
<222> LOCATION: (11)..(11)
<223> OTHER INFORMATION: Ala or Ser
<220> FEATURE:
<221> NAME/KEY: VARIANT
<222> LOCATION: (12)..(12)
<223> OTHER INFORMATION: Ala or Lys
<220> FEATURE:
<221> NAME/KEY: VARIANT
<222> LOCATION: (13)..(13)
<223> OTHER INFORMATION: Ala or Gln
<220> FEATURE:
<221> NAME/KEY: VARIANT
<222> LOCATION: (14)..(14)
<223> OTHER INFORMATION: Ala, Leu, Ile, pentylglycine, Val or Met
<220> FEATURE:
<221> NAME/KEY: VARIANT
<222> LOCATION: (15)..(17)
<223> OTHER INFORMATION: Ala or Glu
<220> FEATURE:
<221> NAME/KEY: VARIANT
<222> LOCATION: (19)..(19)
<223> OTHER INFORMATION: Ala or Val
<220> FEATURE:
<221> NAME/KEY: VARIANT
<222> LOCATION: (20)..(20)
<223> OTHER INFORMATION: Ala or Arg
<220> FEATURE:
<221> NAME/KEY: VARIANT
<222> LOCATION: (21)..(21)
<223> OTHER INFORMATION: Ala or Leu
<220> FEATURE:
<221> NAME/KEY: VARIANT
<222> LOCATION: (22)..(22)
<223> OTHER INFORMATION: Ala, Phe, Tyr or naphthylalanine
<220> FEATURE:
<221> NAME/KEY: VARIANT
<222> LOCATION: (23)..(23)
<223> OTHER INFORMATION: Ile, Val, Leu, pentylglycine, t-butylglycine or
      Met
<220> FEATURE:
<221> NAME/KEY: VARIANT
<222> LOCATION: (24)..(24)
<223> OTHER INFORMATION: Ala, Glu or Asp
<220> FEATURE:
<221> NAME/KEY: VARIANT
<222> LOCATION: (25)..(25)
<223> OTHER INFORMATION: Ala, Trp, Phe, Tyr or naphthylalanine
<220> FEATURE:
<221> NAME/KEY: VARIANT
<222> LOCATION: (26)..(26)
<223> OTHER INFORMATION: Ala or Leu
<220> FEATURE:
<221> NAME/KEY: VARIANT
<222> LOCATION: (27)..(27)
<223> OTHER INFORMATION: Ala or Lys
<220> FEATURE:
<221> NAME/KEY: VARIANT
<222> LOCATION: (28)..(28)
<223> OTHER INFORMATION: Ala or Asn and optionally amidated if positions
      29-28 absent
<220> FEATURE:
<221> NAME/KEY: VARIANT
<222> LOCATION: (29)..(29)
```

```
<223> OTHER INFORMATION: Gly or absent and optionally amidated if
      positions 30-38 absent
<220> FEATURE:
<221> NAME/KEY: VARIANT
<222> LOCATION: (30)..(30)
<223> OTHER INFORMATION: Gly or absent and optionally amidated if
      positions 31-38 absent
<220> FEATURE:
<221> NAME/KEY: VARIANT
<222> LOCATION: (31)..(31)
<223> OTHER INFORMATION: Pro, homoproline, 3Hyp, 4Hyp, thioproline,
      N-alkylglycine, N-alkylpentylglycine N-alkylalanine or absent and
      optionally amidated if positions 32-38 absent
<220> FEATURE:
<221> NAME/KEY: VARIANT
<222> LOCATION: (32)..(32)
<223> OTHER INFORMATION: Ser or absent and optionally amdidated if
      positions 33-38 absent
<220> FEATURE:
<221> NAME/KEY: VARIANT
<222> LOCATION: (33)..(33)
<223> OTHER INFORMATION: Ser or absent and optionally amidated if
      positions 34-38 absent
<220> FEATURE:
<221> NAME/KEY: VARIANT
<222> LOCATION: (34)..(34)
<223> OTHER INFORMATION: Gly or absent and optionally amidated if
      positions 35-38 are absent
<220> FEATURE:
<221> NAME/KEY: VARIANT
<222> LOCATION: (35)..(35)
<223> OTHER INFORMATION: Ala or absent and optionally amidated if
      positions 36-38 absent
<220> FEATURE:
<221> NAME/KEY: VARIANT
<222> LOCATION: (36)..(36)
<223> OTHER INFORMATION: Pro, homoproline, 3Hyp, 4Hyp, thiporline,
      N-alkylglycine, N-alkylpentylglycine, N-alkylglycine or absent and
      optionally amidated if positions 37-38 absent
<220> FEATURE:
<221> NAME/KEY: VARIANT
<222> LOCATION: (37)..(37)
<223> OTHER INFORMATION: Pro, homoproline, 3Hyp, 4Hyp, thiporline,
      N-alkylglycine, N-alkylpentylglycine, N-alkylglycine or absent and
      optionally amidated if position 38 absent
<220> FEATURE:
<221> NAME/KEY: VARIANT
<222> LOCATION: (38)..(38)
<223> OTHER INFORMATION: Pro, homoproline, 3Hyp, 4Hyp, thiporline,
      N-alkylglycine, N-alkylpentylglycine, N-alkylglycine or absent and
      optionally amidated

<400> SEQUENCE: 4

Xaa Xaa Xaa Gly Xaa Xaa Xaa Xaa Xaa Xaa Xaa Xaa Xaa Xaa Xaa Xaa
1               5                   10                  15

Xaa Ala Xaa Xaa Xaa Xaa Xaa Xaa Xaa Xaa Xaa Gly Gly Xaa Ser
            20                  25                  30

Ser Gly Ala Xaa Xaa Xaa
        35

<210> SEQ ID NO 5
<211> LENGTH: 39
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: (1)..(1)
<223> OTHER INFORMATION: His, Arg, Tyr, Ala, norval, Val or norleu
<220> FEATURE:
<221> NAME/KEY: VARIANT
<222> LOCATION: (2)..(2)
<223> OTHER INFORMATION: Ser, Gly, Ala or Thr
<220> FEATURE:
<221> NAME/KEY: VARIANT
```

```
<222> LOCATION: (3)..(3)
<223> OTHER INFORMATION: Ala, Asp or Glu
<220> FEATURE:
<221> NAME/KEY: VARIANT
<222> LOCATION: (4)..(4)
<223> OTHER INFORMATION: Ala, norval, Val, norleu or Gly
<220> FEATURE:
<221> NAME/KEY: VARIANT
<222> LOCATION: (5)..(5)
<223> OTHER INFORMATION: Ala or Thr
<220> FEATURE:
<221> NAME/KEY: VARIANT
<222> LOCATION: (6)..(6)
<223> OTHER INFORMATION: Ala, Phe, Tyr or naphthylalanine
<220> FEATURE:
<221> NAME/KEY: VARIANT
<222> LOCATION: (7)..(7)
<223> OTHER INFORMATION: Thr or Ser
<220> FEATURE:
<221> NAME/KEY: VARIANT
<222> LOCATION: (8)..(8)
<223> OTHER INFORMATION: Ala, Ser or Thr
<220> FEATURE:
<221> NAME/KEY: VARIANT
<222> LOCATION: (9)..(9)
<223> OTHER INFORMATION: Ala, norval, Val, norleu, Asp or Glu
<220> FEATURE:
<221> NAME/KEY: VARIANT
<222> LOCATION: (10)..(10)
<223> OTHER INFORMATION: Ala, Leu, Ile, Val, pentylglycine or Met
<220> FEATURE:
<221> NAME/KEY: VARIANT
<222> LOCATION: (11)..(11)
<223> OTHER INFORMATION: Ala or Ser
<220> FEATURE:
<221> NAME/KEY: VARIANT
<222> LOCATION: (12)..(12)
<223> OTHER INFORMATION: Ala or Lys
<220> FEATURE:
<221> NAME/KEY: VARIANT
<222> LOCATION: (13)..(13)
<223> OTHER INFORMATION: Ala or Gln
<220> FEATURE:
<221> NAME/KEY: VARIANT
<222> LOCATION: (14)..(14)
<223> OTHER INFORMATION: Ala, Leu Ile, pentylglycine, Val or Met
<220> FEATURE:
<221> NAME/KEY: VARIANT
<222> LOCATION: (15)..(17)
<223> OTHER INFORMATION: Ala or Glu
<220> FEATURE:
<221> NAME/KEY: VARIANT
<222> LOCATION: (19)..(19)
<223> OTHER INFORMATION: Ala or Val
<220> FEATURE:
<221> NAME/KEY: VARIANT
<222> LOCATION: (20)..(20)
<223> OTHER INFORMATION: Ala or Arg
<220> FEATURE:
<221> NAME/KEY: VARIANT
<222> LOCATION: (21)..(21)
<223> OTHER INFORMATION: Ala or Leu
<220> FEATURE:
<221> NAME/KEY: VARIANT
<222> LOCATION: (22)..(22)
<223> OTHER INFORMATION: Phe, Tyr or naphthylalanine
<220> FEATURE:
<221> NAME/KEY: VARIANT
<222> LOCATION: (23)..(23)
<223> OTHER INFORMATION: Ile, Val, Leu, pentylglycine, t-butylglycine or
      Met
<220> FEATURE:
<221> NAME/KEY: VARIANT
<222> LOCATION: (24)..(24)
<223> OTHER INFORMATION: Ala, Glu or Asp
<220> FEATURE:
<221> NAME/KEY: VARIANT
<222> LOCATION: (25)..(25)
<223> OTHER INFORMATION: Ala, Trp, Phe, Tyr or naphthylalanine
<220> FEATURE:
```

```
<221> NAME/KEY: VARIANT
<222> LOCATION: (26)..(26)
<223> OTHER INFORMATION: Ala or Leu
<220> FEATURE:
<221> NAME/KEY: VARIANT
<222> LOCATION: (27)..(27)
<223> OTHER INFORMATION: Ala or Lys
<220> FEATURE:
<221> NAME/KEY: VARIANT
<222> LOCATION: (28)..(28)
<223> OTHER INFORMATION: Ala or Asn and is optionally amidated if
      positions 29-38 absent
<220> FEATURE:
<221> NAME/KEY: VARIANT
<222> LOCATION: (29)..(29)
<223> OTHER INFORMATION: Gly or absent and optionally amidated if
      positions 30-38 absent
<220> FEATURE:
<221> NAME/KEY: VARIANT
<222> LOCATION: (30)..(30)
<223> OTHER INFORMATION: Gly or absent and optionally amidated if
      positions 31-38 absent
<220> FEATURE:
<221> NAME/KEY: VARIANT
<222> LOCATION: (31)..(31)
<223> OTHER INFORMATION: Pro, homoproline, 3Hyp, 4Hyp, thioproline,
      N-alkylglycine, N-alkylpentylglycine, N-alkylalanine or absent and
      optionally amidated if positions 32-38 absent
<220> FEATURE:
<221> NAME/KEY: VARIANT
<222> LOCATION: (32)..(32)
<223> OTHER INFORMATION: Ser or absent and optionally amidated if
      positions 33-38 absent
<220> FEATURE:
<221> NAME/KEY: VARIANT
<222> LOCATION: (33)..(33)
<223> OTHER INFORMATION: Ser or absent and optionally amidated if
      positions 34-38 absent
<220> FEATURE:
<221> NAME/KEY: VARIANT
<222> LOCATION: (34)..(34)
<223> OTHER INFORMATION: Gly or absent and optionally amidated if
      positions 35-38 absent
<220> FEATURE:
<221> NAME/KEY: VARIANT
<222> LOCATION: (35)..(35)
<223> OTHER INFORMATION: Ala or absent and optionally amidated if
      positions 36-38 absent
<220> FEATURE:
<221> NAME/KEY: VARIANT
<222> LOCATION: (36)..(36)
<223> OTHER INFORMATION: Pro, homoproline, 3Hyp, 4Hyp, thioproline,
      N-alkylglycine, N-alkylpentylglycine, N-alkylalanine or absent and
      optionally amidated if positions 37-38 absent
<220> FEATURE:
<221> NAME/KEY: VARIANT
<222> LOCATION: (37)..(37)
<223> OTHER INFORMATION: Pro, homoproline, 3Hyp, 4Hyp, thioproline,
      N-alkylglycine, N-alkylpentylglycine, N-alkylalanine or absent and
      optionally amidated if position 38 absent
<220> FEATURE:
<221> NAME/KEY: VARIANT
<222> LOCATION: (38)..(38)
<223> OTHER INFORMATION: Pro, homoproline, 3Hyp, 4Hyp, thioproline,
      N-alkylglycine, N-alkylpentylglycine, N-alkylalanine or absent and
      optionally amidated
<220> FEATURE:
<221> NAME/KEY: VARIANT
<222> LOCATION: (39)..(39)
<223> OTHER INFORMATION: Xaa can be any naturally occurring amino acid

<400> SEQUENCE: 5

Xaa Xaa Xaa Xaa Xaa Xaa Xaa Xaa Xaa Xaa Xaa Xaa Xaa Xaa Xaa Xaa
1               5                   10                  15

Xaa Ala Xaa Xaa Xaa Xaa Xaa Xaa Xaa Xaa Xaa Xaa Gly Gly Xaa Ser
            20                  25                  30

Ser Gly Ala Xaa Xaa Xaa Xaa
```

<210> SEQ ID NO 6
<211> LENGTH: 30
<212> TYPE: PRT
<213> ORGANISM: Artificial Sequence
<220> FEATURE:
<223> OTHER INFORMATION: Synthetic construct

<400> SEQUENCE: 6

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30

<210> SEQ ID NO 7
<211> LENGTH: 30
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (30)..(30)
<223> OTHER INFORMATION: AMIDATION

<400> SEQUENCE: 7

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30

<210> SEQ ID NO 8
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 8

His Gly Glu Gly Thr Phe Thr Ser Asp Leu Ser Lys Gln Leu Glu Glu
1               5                   10                  15

Glu Ala Val Arg Leu Ala Ile Glu Phe Leu Lys Asn
            20                  25

<210> SEQ ID NO 9
<211> LENGTH: 39
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (39)..(39)
<223> OTHER INFORMATION: AMIDATION

<400> SEQUENCE: 9

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Ser
            35

```
<210> SEQ ID NO 10
<211> LENGTH: 39
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (39)..(39)
<223> OTHER INFORMATION: AMIDATION

<400> SEQUENCE: 10

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 11
<211> LENGTH: 39
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (39)..(39)
<223> OTHER INFORMATION: AMIDATION

<400> SEQUENCE: 11

His Gly Glu Gly Thr Phe Thr Ser Asp Leu Ser Lys Gln Met Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro Ser
        35

<210> SEQ ID NO 12
<211> LENGTH: 39
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (39)..(39)
<223> OTHER INFORMATION: AMIDATION

<400> SEQUENCE: 12

Tyr Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 13
<211> LENGTH: 39
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (39)..(39)
```

```
<223> OTHER INFORMATION: AMIDATION

<400> SEQUENCE: 13

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Tyr
        35

<210> SEQ ID NO 14
<211> LENGTH: 39
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (39)..(39)
<223> OTHER INFORMATION: AMIDATION

<400> SEQUENCE: 14

His Gly Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 15
<211> LENGTH: 39
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (6)..(6)
<223> OTHER INFORMATION: naphthylalanine
<220> FEATURE:
<221> NAME/KEY: MOD_RES
<222> LOCATION: (39)..(39)
<223> OTHER INFORMATION: AMIDATION

<400> SEQUENCE: 15

His Gly Glu Gly Thr Ala Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 16
<211> LENGTH: 39
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (39)..(39)
<223> OTHER INFORMATION: AMIDATION

<400> SEQUENCE: 16

His Gly Glu Gly Thr Phe Ser Ser Asp Leu Ser Lys Gln Met Glu Glu
1               5                   10                  15
```

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 17
<211> LENGTH: 39
<212> TYPE: PRT
<213> ORGANISM: Artificial Sequence
<220> FEATURE:
<223> OTHER INFORMATION: Synthetic construct

<400> SEQUENCE: 17

His Gly Glu Gly Thr Phe Ser Thr Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 18
<211> LENGTH: 39
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (39)..(39)
<223> OTHER INFORMATION: AMIDATION

<400> SEQUENCE: 18

His Gly Glu Gly Thr Phe Thr Thr Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 19
<211> LENGTH: 39
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (39)..(39)
<223> OTHER INFORMATION: AMIDATION

<400> SEQUENCE: 19

His Gly Glu Gly Thr Phe Thr Ser Glu Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 20
<211> LENGTH: 39
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES

```
<222> LOCATION: (10)..(10)
<223> OTHER INFORMATION: pentylglycine
<220> FEATURE:
<221> NAME/KEY: MOD_RES
<222> LOCATION: (39)..(39)
<223> OTHER INFORMATION: AMIDATION

<400> SEQUENCE: 20

His Gly Glu Gly Thr Phe Thr Ser Asp Gly Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 21
<211> LENGTH: 39
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (10)..(10)
<223> OTHER INFORMATION: pentylglycine
<220> FEATURE:
<221> NAME/KEY: MOD_RES
<222> LOCATION: (39)..(39)
<223> OTHER INFORMATION: AMIDATION

<400> SEQUENCE: 21

His Gly Glu Gly Thr Phe Thr Ser Asp Gly Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro Ser
        35

<210> SEQ ID NO 22
<211> LENGTH: 39
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (14)..(14)
<223> OTHER INFORMATION: pentylglycine
<220> FEATURE:
<221> NAME/KEY: MOD_RES
<222> LOCATION: (39)..(39)
<223> OTHER INFORMATION: AMIDATION

<400> SEQUENCE: 22

His Gly Glu Gly Thr Phe Thr Ser Asp Leu Ser Lys Gln Gly Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 23
<211> LENGTH: 39
<212> TYPE: PRT
<213> ORGANISM: Artificial Sequence
<220> FEATURE:
<223> OTHER INFORMATION: Synthetic construct
<220> FEATURE:
```

```
<221> NAME/KEY: MOD_RES
<222> LOCATION: (14)..(14)
<223> OTHER INFORMATION: pentylglycine
<220> FEATURE:
<221> NAME/KEY: MOD_RES
<222> LOCATION: (39)..(39)
<223> OTHER INFORMATION: AMIDATION

<400> SEQUENCE: 23

His Gly Glu Gly Thr Phe Thr Ser Asp Leu Ser Lys Gln Gly Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro Ser
        35

<210> SEQ ID NO 24
<211> LENGTH: 39
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (22)..(22)
<223> OTHER INFORMATION: naphthylalanine
<220> FEATURE:
<221> NAME/KEY: MOD_RES
<222> LOCATION: (39)..(39)
<223> OTHER INFORMATION: AMIDATION

<400> SEQUENCE: 24

His Gly Glu Gly Thr Phe Thr Ser Asp Leu Ser Lys Gln Met Glu Glu
1               5                   10                  15

Glu Ala Val Arg Leu Ala Ile Glu Trp Leu Lys Asn Gly Gly Pro Ser
            20                  25                  30

Ser Gly Ala Pro Pro Pro Ser
        35

<210> SEQ ID NO 25
<211> LENGTH: 39
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (39)..(39)
<223> OTHER INFORMATION: AMIDATION

<400> SEQUENCE: 25

His Gly Glu Gly Thr Phe Thr Ser Asp Leu Ser Lys Gln Met Glu Glu
1               5                   10                  15

Glu Ala Val Arg Leu Phe Val Glu Trp Leu Lys Asn Gly Gly Pro Ser
            20                  25                  30

Ser Gly Ala Pro Pro Pro Ser
        35

<210> SEQ ID NO 26
<211> LENGTH: 39
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (39)..(39)
<223> OTHER INFORMATION: AMIDATION
```

```
<400> SEQUENCE: 26

His Gly Glu Gly Thr Phe Thr Ser Asp Leu Ser Lys Gln Leu Glu Glu
1               5                   10                  15

Glu Ala Val Arg Leu Phe Val Glu Phe Leu Lys Asn Gly Gly Pro Ser
            20                  25                  30

Ser Gly Ala Pro Pro Pro Ser
        35

<210> SEQ ID NO 27
<211> LENGTH: 39
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (23)..(23)
<223> OTHER INFORMATION: t-butylglycine
<220> FEATURE:
<221> NAME/KEY: MOD_RES
<222> LOCATION: (39)..(39)
<223> OTHER INFORMATION: AMIDATION

<400> SEQUENCE: 27

His Gly Glu Gly Thr Phe Thr Ser Asp Leu Ser Lys Gln Met Glu Glu
1               5                   10                  15

Glu Ala Val Arg Leu Phe Gly Glu Trp Leu Lys Asn Gly Gly Pro Ser
            20                  25                  30

Ser Gly Ala Pro Pro Pro Ser
        35

<210> SEQ ID NO 28
<211> LENGTH: 39
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (23)..(23)
<223> OTHER INFORMATION: t-butylglycine
<220> FEATURE:
<221> NAME/KEY: MOD_RES
<222> LOCATION: (39)..(39)
<223> OTHER INFORMATION: AMIDATION

<400> SEQUENCE: 28

His Gly Glu Gly Thr Phe Thr Ser Asp Leu Ser Lys Gln Leu Glu Glu
1               5                   10                  15

Glu Ala Val Arg Leu Phe Gly Glu Phe Leu Lys Asn Gly Gly Pro Ser
            20                  25                  30

Ser Gly Ala Pro Pro Pro Ser
        35

<210> SEQ ID NO 29
<211> LENGTH: 39
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (39)..(39)
<223> OTHER INFORMATION: AMIDATION

<400> SEQUENCE: 29
```

His Gly Glu Gly Thr Phe Thr Ser Asp Leu Ser Lys Gln Met Glu Glu
1               5                   10                  15

Glu Ala Val Arg Leu Phe Ile Asp Trp Leu Lys Asn Gly Gly Pro Ser
            20                  25                  30

Ser Gly Ala Pro Pro Ser
        35

<210> SEQ ID NO 30
<211> LENGTH: 39
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (39)..(39)
<223> OTHER INFORMATION: AMIDATION

<400> SEQUENCE: 30

His Ala Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Ser
        35

<210> SEQ ID NO 31
<211> LENGTH: 39
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (31)..(31)
<223> OTHER INFORMATION: thioproline
<220> FEATURE:
<221> NAME/KEY: MOD_RES
<222> LOCATION: (36)..(38)
<223> OTHER INFORMATION: thioproline
<220> FEATURE:
<221> NAME/KEY: MOD_RES
<222> LOCATION: (39)..(39)
<223> OTHER INFORMATION: AMIDATION

<400> SEQUENCE: 31

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 32
<211> LENGTH: 39
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (36)..(38)
<223> OTHER INFORMATION: thioproline
<220> FEATURE:
<221> NAME/KEY: MOD_RES
<222> LOCATION: (39)..(39)
<223> OTHER INFORMATION: AMIDATION

<400> SEQUENCE: 32

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 33
<211> LENGTH: 39
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (31)..(31)
<223> OTHER INFORMATION: homoproline
<220> FEATURE:
<221> NAME/KEY: MOD_RES
<222> LOCATION: (36)..(38)
<223> OTHER INFORMATION: homoproline
<220> FEATURE:
<221> NAME/KEY: MOD_RES
<222> LOCATION: (39)..(39)
<223> OTHER INFORMATION: AMIDATION

<400> SEQUENCE: 33

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 34
<211> LENGTH: 39
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (36)..(38)
<223> OTHER INFORMATION: homoproline
<220> FEATURE:
<221> NAME/KEY: MOD_RES
<222> LOCATION: (39)..(39)
<223> OTHER INFORMATION: AMIDATION

<400> SEQUENCE: 34

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 35
<211> LENGTH: 39
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (31)..(31)
<223> OTHER INFORMATION: thioproline
<220> FEATURE:

```
<221> NAME/KEY: MOD_RES
<222> LOCATION: (36)..(38)
<223> OTHER INFORMATION: thioproline
<220> FEATURE:
<221> NAME/KEY: MOD_RES
<222> LOCATION: (39)..(39)
<223> OTHER INFORMATION: AMIDATION

<400> SEQUENCE: 35

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro Ser
        35

<210> SEQ ID NO 36
<211> LENGTH: 39
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (31)..(31)
<223> OTHER INFORMATION: homoproline
<220> FEATURE:
<221> NAME/KEY: MOD_RES
<222> LOCATION: (36)..(38)
<223> OTHER INFORMATION: homoproline
<220> FEATURE:
<221> NAME/KEY: MOD_RES
<222> LOCATION: (39)..(39)
<223> OTHER INFORMATION: AMIDATION

<400> SEQUENCE: 36

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro Ser
        35

<210> SEQ ID NO 37
<211> LENGTH: 39
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (31)..(31)
<223> OTHER INFORMATION: N-methylalanine
<220> FEATURE:
<221> NAME/KEY: MOD_RES
<222> LOCATION: (36)..(38)
<223> OTHER INFORMATION: N-methylalanine
<220> FEATURE:
<221> NAME/KEY: MOD_RES
<222> LOCATION: (39)..(39)
<223> OTHER INFORMATION: AMIDATION

<400> SEQUENCE: 37

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Ala Ser
            20                  25                  30

Ser Gly Ala Ala Ala Ala Ser
        35
```

```
<210> SEQ ID NO 38
<211> LENGTH: 39
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (36)..(38)
<223> OTHER INFORMATION: N-methylalanine
<220> FEATURE:
<221> NAME/KEY: MOD_RES
<222> LOCATION: (39)..(39)
<223> OTHER INFORMATION: AMIDATION

<400> SEQUENCE: 38

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn Gly Gly Pro Ser
                20                  25                  30

Ser Gly Ala Ala Ala Ala Ser
            35

<210> SEQ ID NO 39
<211> LENGTH: 39
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (31)..(31)
<223> OTHER INFORMATION: N-methylalanine
<220> FEATURE:
<221> NAME/KEY: MOD_RES
<222> LOCATION: (36)..(38)
<223> OTHER INFORMATION: N-methylalanine
<220> FEATURE:
<221> NAME/KEY: MOD_RES
<222> LOCATION: (39)..(39)
<223> OTHER INFORMATION: AMIDATION

<400> SEQUENCE: 39

His Gly Glu Gly Thr Phe Thr Ser Asp Leu Ser Lys Gln Leu Glu Glu
  1               5                  10                  15

Glu Ala Val Arg Leu Phe Ile Glu Phe Leu Lys Asn Gly Gly Ala Ser
                20                  25                  30

Ser Gly Ala Ala Ala Ala Ser
            35

<210> SEQ ID NO 40
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 40

His Gly Glu Gly Thr Phe Thr Ser Asp Leu Ser Lys Gln Met Glu Glu
  1               5                  10                  15

Glu Ala Val Arg Leu Phe Ile Glu Trp Leu Lys Asn
                20                  25
```

```
<210> SEQ ID NO 41
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 41

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 42
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 42

His Ala Glu Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 43
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 43

His Gly Glu Gly Ala Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 44
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 44

His Gly Glu Gly Thr Ala Thr Ser Asp Leu Ser Lys Gln Leu Glu Glu
1               5                   10                  15

Glu Ala Val Arg Leu Phe Ile Glu Phe Leu Lys Asn
            20                  25
```

```
<210> SEQ ID NO 45
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 45

His Gly Glu Gly Thr Phe Thr Ala Asp Leu Ser Lys Gln Leu Glu Glu
1               5                   10                  15

Glu Ala Val Arg Leu Phe Ile Glu Phe Leu Lys Asn
            20                  25

<210> SEQ ID NO 46
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 46

His Gly Glu Gly Thr Phe Thr Ser Asp Ala Ser Lys Gln Leu Glu Glu
1               5                   10                  15

Glu Ala Val Arg Leu Phe Ile Glu Phe Leu Lys Asn
            20                  25

<210> SEQ ID NO 47
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 47

His Gly Glu Gly Thr Phe Thr Ser Asp Leu Ala Lys Gln Leu Glu Glu
1               5                   10                  15

Glu Ala Val Arg Leu Phe Ile Glu Phe Leu Lys Asn
            20                  25

<210> SEQ ID NO 48
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 48

His Gly Glu Gly Thr Phe Thr Ser Asp Leu Ser Ala Gln Leu Glu Glu
1               5                   10                  15

Glu Ala Val Arg Leu Phe Ile Glu Phe Leu Lys Asn
            20                  25
```

```
<210> SEQ ID NO 49
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 49

His Gly Glu Gly Thr Phe Thr Ser Asp Leu Ser Lys Ala Leu Glu Glu
1               5                   10                  15

Glu Ala Val Arg Leu Phe Ile Glu Phe Leu Lys Asn
            20                  25

<210> SEQ ID NO 50
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 50

His Gly Glu Gly Thr Phe Thr Ser Asp Leu Ser Lys Gln Ala Glu Glu
1               5                   10                  15

Glu Ala Val Arg Leu Phe Ile Glu Phe Leu Lys Asn
            20                  25

<210> SEQ ID NO 51
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 51

His Gly Glu Gly Thr Phe Thr Ser Asp Leu Ser Lys Gln Leu Ala Glu
1               5                   10                  15

Glu Ala Val Arg Leu Phe Ile Glu Phe Leu Lys Asn
            20                  25

<210> SEQ ID NO 52
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 52

His Gly Glu Gly Thr Phe Thr Ser Asp Leu Ser Lys Gln Leu Glu Ala
1               5                   10                  15

Glu Ala Val Arg Leu Phe Ile Glu Phe Leu Lys Asn
            20                  25
```

```
<210> SEQ ID NO 53
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 53

His Gly Glu Gly Thr Phe Thr Ser Asp Leu Ser Lys Gln Leu Glu Glu
 1               5                  10                  15

Ala Ala Val Arg Leu Phe Ile Glu Phe Leu Lys Asn
            20                  25

<210> SEQ ID NO 54
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 54

His Gly Glu Gly Thr Phe Thr Ser Asp Leu Ser Lys Gln Leu Glu Glu
 1               5                  10                  15

Glu Ala Ala Arg Leu Phe Ile Glu Phe Leu Lys Asn
            20                  25

<210> SEQ ID NO 55
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 55

His Gly Glu Gly Thr Phe Thr Ser Asp Leu Ser Lys Gln Leu Glu Glu
 1               5                  10                  15

Glu Ala Val Ala Leu Phe Ile Glu Phe Leu Lys Asn
            20                  25

<210> SEQ ID NO 56
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 56

His Gly Glu Gly Thr Phe Thr Ser Asp Leu Ser Lys Gln Leu Glu Glu
 1               5                  10                  15

Glu Ala Val Arg Ala Phe Ile Glu Phe Leu Lys Asn
            20                  25
```

```
<210> SEQ ID NO 57
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 57

His Gly Glu Gly Thr Phe Thr Ser Asp Leu Ser Lys Gln Leu Glu Glu
1               5                   10                  15

Glu Ala Val Arg Leu Phe Ile Ala Phe Leu Lys Asn
            20                  25

<210> SEQ ID NO 58
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 58

His Gly Glu Gly Thr Phe Thr Ser Asp Leu Ser Lys Gln Leu Glu Glu
1               5                   10                  15

Glu Ala Val Arg Leu Phe Ile Glu Ala Leu Lys Asn
            20                  25

<210> SEQ ID NO 59
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 59

His Gly Glu Gly Thr Phe Thr Ser Asp Leu Ser Lys Gln Leu Glu Glu
1               5                   10                  15

Glu Ala Val Arg Leu Phe Ile Glu Phe Ala Lys Asn
            20                  25

<210> SEQ ID NO 60
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 60

His Gly Glu Gly Thr Phe Thr Ser Asp Leu Ser Lys Gln Leu Glu Glu
1               5                   10                  15

Glu Ala Val Arg Leu Phe Ile Glu Phe Leu Ala Asn
            20                  25
```

```
<210> SEQ ID NO 61
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 61

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Ala
            20                  25

<210> SEQ ID NO 62
<211> LENGTH: 38
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (38)..(38)
<223> OTHER INFORMATION: AMIDATION

<400> SEQUENCE: 62

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro
        35

<210> SEQ ID NO 63
<211> LENGTH: 38
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (38)..(38)
<223> OTHER INFORMATION: AMIDATION

<400> SEQUENCE: 63

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro
        35

<210> SEQ ID NO 64
<211> LENGTH: 37
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (37)..(37)
<223> OTHER INFORMATION: AMIDATION

<400> SEQUENCE: 64

His Gly Glu Gly Thr Phe Thr Ser Asp Leu Ser Lys Gln Met Glu Glu
```

```
                1               5                  10                 15
Glu Ala Val Arg Leu Phe Ile Glu Trp Leu Lys Asn Gly Gly Pro Ser
                20                 25                 30

Ser Gly Ala Pro Pro
        35

<210> SEQ ID NO 65
<211> LENGTH: 37
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (37)..(37)
<223> OTHER INFORMATION: AMIDATION

<400> SEQUENCE: 65

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
                20                  25                  30

Ser Gly Ala Pro Pro
        35

<210> SEQ ID NO 66
<211> LENGTH: 36
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (36)..(36)
<223> OTHER INFORMATION: AMIDATION

<400> SEQUENCE: 66

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro
        35

<210> SEQ ID NO 67
<211> LENGTH: 36
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (36)..(36)
<223> OTHER INFORMATION: AMIDATION

<400> SEQUENCE: 67

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
                20                  25                  30

Ser Gly Ala Pro
        35

<210> SEQ ID NO 68
<211> LENGTH: 35
```

```
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (35)..(35)
<223> OTHER INFORMATION: AMIDATION

<400> SEQUENCE: 68

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala
        35

<210> SEQ ID NO 69
<211> LENGTH: 35
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (35)..(35)
<223> OTHER INFORMATION: AMIDATION

<400> SEQUENCE: 69

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala
        35

<210> SEQ ID NO 70
<211> LENGTH: 34
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (34)..(34)
<223> OTHER INFORMATION: AMIDATION

<400> SEQUENCE: 70

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly

<210> SEQ ID NO 71
<211> LENGTH: 34
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (34)..(34)
<223> OTHER INFORMATION: AMIDATION

<400> SEQUENCE: 71

His Gly Glu Gly Thr Phe Thr Ser Asp Leu Ser Lys Gln Leu Glu Glu
```

```
1               5                   10                  15
Glu Ala Val Arg Leu Phe Ile Glu Phe Leu Lys Asn Gly Gly Pro Ser
            20                  25                  30

Ser Gly

<210> SEQ ID NO 72
<211> LENGTH: 33
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (33)..(33)
<223> OTHER INFORMATION: AMIDATION

<400> SEQUENCE: 72

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser

<210> SEQ ID NO 73
<211> LENGTH: 33
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (33)..(33)
<223> OTHER INFORMATION: AMIDATION

<400> SEQUENCE: 73

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser

<210> SEQ ID NO 74
<211> LENGTH: 32
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (32)..(32)
<223> OTHER INFORMATION: AMIDATION

<400> SEQUENCE: 74

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

<210> SEQ ID NO 75
<211> LENGTH: 32
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
```

```
<222> LOCATION: (32)..(32)
<223> OTHER INFORMATION: AMIDATION

<400> SEQUENCE: 75

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

<210> SEQ ID NO 76
<211> LENGTH: 31
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (31)..(31)
<223> OTHER INFORMATION: AMIDATION

<400> SEQUENCE: 76

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro
            20                  25                  30

<210> SEQ ID NO 77
<211> LENGTH: 31
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (31)..(31)
<223> OTHER INFORMATION: AMIDATION

<400> SEQUENCE: 77

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro
            20                  25                  30

<210> SEQ ID NO 78
<211> LENGTH: 30
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (30)..(30)
<223> OTHER INFORMATION: AMIDATION

<400> SEQUENCE: 78

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly
            20                  25                  30

<210> SEQ ID NO 79
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
```

```
<222> LOCATION: (29)..(29)
<223> OTHER INFORMATION: AMIDATION

<400> SEQUENCE: 79

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly
            20                  25

<210> SEQ ID NO 80
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (29)..(29)
<223> OTHER INFORMATION: AMIDATION

<400> SEQUENCE: 80

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly
            20                  25

<210> SEQ ID NO 81
<211> LENGTH: 38
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (31)..(31)
<223> OTHER INFORMATION: thioproline
<220> FEATURE:
<221> NAME/KEY: MOD_RES
<222> LOCATION: (36)..(38)
<223> OTHER INFORMATION: thioproline
<220> FEATURE:
<221> NAME/KEY: MOD_RES
<222> LOCATION: (38)..(38)
<223> OTHER INFORMATION: AMIDATION

<400> SEQUENCE: 81

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro
        35

<210> SEQ ID NO 82
<211> LENGTH: 38
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (36)..(38)
<223> OTHER INFORMATION: thioproline
<220> FEATURE:
<221> NAME/KEY: MOD_RES
<222> LOCATION: (38)..(38)
<223> OTHER INFORMATION: AMIDATION

<400> SEQUENCE: 82
```

His Gly Glu Gly Thr Phe Thr Ser Asp Leu Ser Lys Gln Met Glu
1               5                   10                  15

Glu Ala Val Arg Leu Phe Ile Glu Trp Leu Lys Asn Gly Gly Pro Ser
            20                  25                  30

Ser Gly Ala Pro Pro Pro
        35

<210> SEQ ID NO 83
<211> LENGTH: 37
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (31)..(31)
<223> OTHER INFORMATION: N-methylalanine
<220> FEATURE:
<221> NAME/KEY: MOD_RES
<222> LOCATION: (37)..(37)
<223> OTHER INFORMATION: AMIDATION

<400> SEQUENCE: 83

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Ala Ser
            20                  25                  30

Ser Gly Ala Pro Pro
        35

<210> SEQ ID NO 84
<211> LENGTH: 37
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (31)..(31)
<223> OTHER INFORMATION: N-methylalanine
<220> FEATURE:
<221> NAME/KEY: MOD_RES
<222> LOCATION: (36)..(37)
<223> OTHER INFORMATION: N-methylalanine
<220> FEATURE:
<221> NAME/KEY: MOD_RES
<222> LOCATION: (37)..(37)
<223> OTHER INFORMATION: AMIDATION

<400> SEQUENCE: 84

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Ala Ser
            20                  25                  30

Ser Gly Ala Ala Ala
        35

<210> SEQ ID NO 85
<211> LENGTH: 37
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (31)..(31)
<223> OTHER INFORMATION: homoproline
<220> FEATURE:
<221> NAME/KEY: MOD_RES

```
<222> LOCATION: (36)..(37)
<223> OTHER INFORMATION: homoproline
<220> FEATURE:
<221> NAME/KEY: MOD_RES
<222> LOCATION: (37)..(37)
<223> OTHER INFORMATION: AMIDATION

<400> SEQUENCE: 85

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro
        35

<210> SEQ ID NO 86
<211> LENGTH: 36
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (31)..(31)
<223> OTHER INFORMATION: homoproline
<220> FEATURE:
<221> NAME/KEY: MOD_RES
<222> LOCATION: (36)..(36)
<223> OTHER INFORMATION: AMIDATION
<220> FEATURE:
<221> NAME/KEY: MOD_RES
<222> LOCATION: (36)..(36)
<223> OTHER INFORMATION: homoproline

<400> SEQUENCE: 86

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro
        35

<210> SEQ ID NO 87
<211> LENGTH: 35
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (35)..(35)
<223> OTHER INFORMATION: AMIDATION

<400> SEQUENCE: 87

Arg Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala
        35

<210> SEQ ID NO 88
<211> LENGTH: 30
<212> TYPE: PRT
<213> ORGANISM: Artificial Sequence
<220> FEATURE:
<223> OTHER INFORMATION: Synthetic construct
<220> FEATURE:
```

```
<221> NAME/KEY: MOD_RES
<222> LOCATION: (30)..(30)
<223> OTHER INFORMATION: AMIDATION

<400> SEQUENCE: 88

His Gly Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30

<210> SEQ ID NO 89
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (6)..(6)
<223> OTHER INFORMATION: naphthylalanine
<220> FEATURE:
<221> NAME/KEY: MOD_RES
<222> LOCATION: (28)..(28)
<223> OTHER INFORMATION: AMIDATION

<400> SEQUENCE: 89

His Gly Glu Gly Thr Ala Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 90
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 90

His Gly Glu Gly Thr Phe Ser Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 91
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 91

His Gly Glu Gly Thr Phe Ser Thr Asp Leu Ser Lys Gln Met Glu Glu
1               5                   10                  15

Glu Ala Val Arg Leu Phe Ile Glu Trp Leu Lys Asn
            20                  25

<210> SEQ ID NO 92
<211> LENGTH: 28
<212> TYPE: PRT
```

```
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 92

His Gly Glu Gly Thr Phe Thr Ser Glu Leu Ser Lys Gln Met Ala Glu
1               5                   10                  15

Glu Ala Val Arg Leu Phe Ile Glu Trp Leu Lys Asn
            20                  25

<210> SEQ ID NO 93
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (10)..(10)
<223> OTHER INFORMATION: pentylglycine
<220> FEATURE:
<221> NAME/KEY: MOD_RES
<222> LOCATION: (28)..(28)
<223> OTHER INFORMATION: AMIDATION

<400> SEQUENCE: 93

His Gly Glu Gly Thr Phe Thr Ser Asp Gly Ser Lys Gln Leu Glu Glu
1               5                   10                  15

Glu Ala Val Arg Leu Phe Ile Glu Phe Leu Lys Asn
            20                  25

<210> SEQ ID NO 94
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (22)..(22)
<223> OTHER INFORMATION: naphthylalanine
<220> FEATURE:
<221> NAME/KEY: MOD_RES
<222> LOCATION: (28)..(28)
<223> OTHER INFORMATION: AMIDATION

<400> SEQUENCE: 94

His Gly Glu Gly Thr Phe Thr Ser Asp Leu Ser Lys Gln Leu Glu Glu
1               5                   10                  15

Glu Ala Val Arg Leu Ala Ile Glu Phe Leu Lys Asn
            20                  25

<210> SEQ ID NO 95
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (23)..(23)
<223> OTHER INFORMATION: t-butylglycine
<220> FEATURE:
<221> NAME/KEY: MOD_RES
<222> LOCATION: (28)..(28)
<223> OTHER INFORMATION: AMIDATION
```

```
<400> SEQUENCE: 95

His Gly Glu Gly Thr Phe Thr Ser Asp Leu Ser Lys Gln Met Glu Glu
1               5                   10                  15

Glu Ala Val Arg Leu Phe Gly Glu Trp Leu Lys Asn
            20                  25

<210> SEQ ID NO 96
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 96

His Gly Glu Gly Thr Phe Thr Ser Asp Leu Ser Lys Gln Leu Glu Glu
1               5                   10                  15

Glu Ala Val Arg Leu Phe Ile Asp Phe Leu Lys Asn
            20                  25

<210> SEQ ID NO 97
<211> LENGTH: 33
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (33)..(33)
<223> OTHER INFORMATION: AMIDATION

<400> SEQUENCE: 97

His Gly Glu Gly Thr Phe Thr Ser Asp Ala Ser Lys Gln Leu Glu Glu
1               5                   10                  15

Glu Ala Val Arg Leu Phe Ile Glu Phe Leu Lys Asn Gly Gly Pro Ser
            20                  25                  30

Ser

<210> SEQ ID NO 98
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (29)..(29)
<223> OTHER INFORMATION: AMIDATION

<400> SEQUENCE: 98

His Gly Glu Gly Thr Phe Thr Ser Asp Ala Ser Lys Gln Met Glu Glu
1               5                   10                  15

Glu Ala Val Arg Leu Phe Ile Glu Trp Leu Lys Asn Gly
            20                  25

<210> SEQ ID NO 99
<211> LENGTH: 37
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (31)..(31)
```

```
<223> OTHER INFORMATION: homoproline
<220> FEATURE:
<221> NAME/KEY: MOD_RES
<222> LOCATION: (36)..(37)
<223> OTHER INFORMATION: homoproline
<220> FEATURE:
<221> NAME/KEY: MOD_RES
<222> LOCATION: (37)..(37)
<223> OTHER INFORMATION: AMIDATION

<400> SEQUENCE: 99

His Gly Glu Gly Thr Phe Thr Ser Asp Ala Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro
        35

<210> SEQ ID NO 100
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 100

Ala Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 101
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 101

His Gly Ala Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 102
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 102

His Gly Glu Ala Thr Phe Thr Ser Asp Leu Ser Lys Gln Leu Glu Glu
1               5                   10                  15

Glu Ala Val Arg Leu Phe Ile Glu Phe Leu Lys Asn
            20                  25
```

<210> SEQ ID NO 103
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 103

His Gly Glu Gly Thr Phe Thr Ser Ala Leu Ser Lys Gln Leu Glu Glu
1               5                   10                  15

Glu Ala Val Arg Leu Phe Ile Glu Phe Leu Lys Asn
            20                  25

<210> SEQ ID NO 104
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 104

Ala Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 105
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 105

His Gly Ala Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 106
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 106

His Gly Glu Ala Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 107
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 107

His Gly Glu Gly Thr Phe Thr Ser Ala Leu Ser Lys Gln Met Glu Glu
1               5                   10                  15

Glu Ala Val Arg Leu Phe Ile Glu Trp Leu Lys Asn
            20                  25

<210> SEQ ID NO 108
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 108

His Gly Glu Gly Thr Phe Thr Ser Asp Ala Ser Lys Gln Met Glu Glu
1               5                   10                  15

Glu Ala Val Arg Leu Phe Ile Glu Trp Leu Lys Asn
            20                  25

<210> SEQ ID NO 109
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 109

Ala Ala Glu Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 110
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 110

Ala Ala Glu Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25

```
<210> SEQ ID NO 111
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 111

Ala Gly Asp Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 112
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 112

Ala Gly Asp Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 113
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 113

Ala Gly Asp Gly Ala Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 114
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 114

Ala Gly Asp Gly Ala Phe Thr Ser Asp Leu Ser Lys Gln Leu Glu Glu
1               5                   10                  15

Glu Ala Val Arg Leu Phe Ile Glu Phe Leu Lys Asn
            20                  25
```

<210> SEQ ID NO 115
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (6)..(6)
<223> OTHER INFORMATION: naphthylalanine
<220> FEATURE:
<221> NAME/KEY: MOD_RES
<222> LOCATION: (28)..(28)
<223> OTHER INFORMATION: AMIDATION

<400> SEQUENCE: 115

Ala Gly Asp Gly Thr Ala Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 116
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (6)..(6)
<223> OTHER INFORMATION: naphthylalanine
<220> FEATURE:
<221> NAME/KEY: MOD_RES
<222> LOCATION: (28)..(28)
<223> OTHER INFORMATION: AMIDATION

<400> SEQUENCE: 116

Ala Gly Asp Gly Thr Ala Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 117
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 117

Ala Gly Asp Gly Thr Phe Ser Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 118
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

```
<400> SEQUENCE: 118

Ala Gly Asp Gly Thr Phe Ser Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 119
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 119

Ala Gly Asp Gly Thr Phe Thr Ala Asp Leu Ser Lys Gln Met Glu Glu
1               5                   10                  15

Glu Ala Val Arg Leu Phe Ile Glu Trp Leu Lys Asn
            20                  25

<210> SEQ ID NO 120
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 120

Ala Gly Asp Gly Thr Phe Thr Ala Asp Leu Ser Lys Gln Leu Glu Glu
1               5                   10                  15

Glu Ala Val Arg Leu Phe Ile Glu Phe Leu Lys Asn
            20                  25

<210> SEQ ID NO 121
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 121

Ala Gly Asp Gly Thr Phe Thr Ser Ala Leu Ser Lys Gln Met Glu Glu
1               5                   10                  15

Glu Ala Val Arg Leu Phe Ile Glu Trp Leu Lys Asn
            20                  25

<210> SEQ ID NO 122
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION
```

<400> SEQUENCE: 122

Ala Gly Asp Gly Thr Phe Thr Ser Ala Leu Ser Lys Gln Leu Glu Glu
1               5                   10                  15

Glu Ala Val Arg Leu Phe Ile Glu Phe Leu Lys Asn
            20                  25

<210> SEQ ID NO 123
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 123

Ala Gly Asp Gly Thr Phe Thr Ser Glu Leu Ser Lys Gln Met Glu Glu
1               5                   10                  15

Glu Ala Val Arg Leu Phe Ile Glu Trp Leu Lys Asn
            20                  25

<210> SEQ ID NO 124
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 124

Ala Gly Asp Gly Thr Phe Thr Ser Glu Leu Ser Lys Gln Leu Glu Glu
1               5                   10                  15

Glu Ala Val Arg Leu Phe Ile Glu Phe Leu Lys Asn
            20                  25

<210> SEQ ID NO 125
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 125

Ala Gly Asp Gly Thr Phe Thr Ser Asp Ala Ser Lys Gln Met Glu Glu
1               5                   10                  15

Glu Ala Val Arg Leu Phe Ile Glu Trp Leu Lys Asn
            20                  25

<210> SEQ ID NO 126
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

```
<400> SEQUENCE: 126

Ala Gly Asp Gly Thr Phe Thr Ser Asp Ala Ser Lys Gln Leu Glu Glu
1               5                   10                  15

Glu Ala Val Arg Leu Phe Ile Glu Phe Leu Lys Asn
            20                  25

<210> SEQ ID NO 127
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (10)..(10)
<223> OTHER INFORMATION: pentylglycine
<220> FEATURE:
<221> NAME/KEY: MOD_RES
<222> LOCATION: (28)..(28)
<223> OTHER INFORMATION: AMIDATION

<400> SEQUENCE: 127

Ala Gly Asp Gly Thr Phe Thr Ser Asp Gly Ser Lys Gln Met Glu Glu
1               5                   10                  15

Glu Ala Val Arg Leu Phe Ile Glu Trp Leu Lys Asn
            20                  25

<210> SEQ ID NO 128
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (10)..(10)
<223> OTHER INFORMATION: pentylglycine
<220> FEATURE:
<221> NAME/KEY: MOD_RES
<222> LOCATION: (28)..(28)
<223> OTHER INFORMATION: AMIDATION

<400> SEQUENCE: 128

Ala Gly Asp Gly Thr Phe Thr Ser Asp Gly Ser Lys Gln Leu Glu Glu
1               5                   10                  15

Glu Ala Val Arg Leu Phe Ile Glu Phe Leu Lys Asn
            20                  25

<210> SEQ ID NO 129
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 129

Ala Gly Asp Gly Thr Phe Thr Ser Asp Leu Ala Lys Gln Met Glu Glu
1               5                   10                  15

Glu Ala Val Arg Leu Phe Ile Glu Trp Leu Lys Asn
            20                  25

<210> SEQ ID NO 130
<211> LENGTH: 28
```

```
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 130

Ala Gly Asp Gly Thr Phe Thr Ser Asp Leu Ala Lys Gln Leu Glu Glu
1               5                   10                  15

Glu Ala Val Arg Leu Phe Ile Glu Phe Leu Lys Asn
            20                  25

<210> SEQ ID NO 131
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 131

Ala Gly Asp Gly Thr Phe Thr Ser Asp Leu Ser Ala Gln Met Glu Glu
1               5                   10                  15

Glu Ala Val Arg Leu Phe Ile Glu Trp Leu Lys Asn
            20                  25

<210> SEQ ID NO 132
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 132

Ala Gly Asp Gly Thr Phe Thr Ser Asp Leu Ser Ala Gln Leu Glu Glu
1               5                   10                  15

Glu Ala Val Arg Leu Phe Ile Glu Phe Leu Lys Asn
            20                  25

<210> SEQ ID NO 133
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 133

Ala Gly Asp Gly Thr Phe Thr Ser Asp Leu Ser Lys Ala Met Glu Glu
1               5                   10                  15

Glu Ala Val Arg Leu Phe Ile Glu Trp Leu Lys Asn
            20                  25

<210> SEQ ID NO 134
<211> LENGTH: 28
```

```
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 134

Ala Gly Asp Gly Thr Phe Thr Ser Asp Leu Ser Lys Ala Leu Glu Glu
1               5                   10                  15

Glu Ala Val Arg Leu Phe Ile Glu Phe Leu Lys Asn
            20                  25

<210> SEQ ID NO 135
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 135

Ala Gly Asp Gly Thr Phe Thr Ser Asp Leu Ser Lys Gln Ala Glu Glu
1               5                   10                  15

Glu Ala Val Arg Leu Phe Ile Glu Trp Leu Lys Asn
            20                  25

<210> SEQ ID NO 136
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 136

Ala Gly Asp Gly Thr Phe Thr Ser Asp Leu Ser Lys Gln Ala Glu Glu
1               5                   10                  15

Glu Ala Val Arg Leu Phe Ile Glu Phe Leu Lys Asn
            20                  25

<210> SEQ ID NO 137
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (14)..(14)
<223> OTHER INFORMATION: pentylglycine
<220> FEATURE:
<221> NAME/KEY: MOD_RES
<222> LOCATION: (28)..(28)
<223> OTHER INFORMATION: AMIDATION

<400> SEQUENCE: 137

Ala Gly Asp Gly Thr Phe Thr Ser Asp Leu Ser Lys Gln Gly Glu Glu
1               5                   10                  15

Glu Ala Val Arg Leu Phe Ile Glu Trp Leu Lys Asn
            20                  25
```

```
<210> SEQ ID NO 138
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (14)..(14)
<223> OTHER INFORMATION: pentylglycine
<220> FEATURE:
<221> NAME/KEY: MOD_RES
<222> LOCATION: (28)..(28)
<223> OTHER INFORMATION: AMIDATION

<400> SEQUENCE: 138

Ala Gly Asp Gly Thr Phe Thr Ser Asp Leu Ser Lys Gln Gly Glu Glu
1               5                   10                  15

Glu Ala Val Arg Leu Phe Ile Glu Phe Leu Lys Asn
            20                  25

<210> SEQ ID NO 139
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 139

Ala Gly Asp Gly Thr Phe Thr Ser Asp Leu Ser Lys Gln Met Ala Glu
1               5                   10                  15

Glu Ala Val Arg Leu Phe Ile Glu Trp Leu Lys Asn
            20                  25

<210> SEQ ID NO 140
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 140

Ala Gly Asp Gly Thr Phe Thr Ser Asp Leu Ser Lys Gln Leu Ala Glu
1               5                   10                  15

Glu Ala Val Arg Leu Phe Ile Glu Phe Leu Lys Asn
            20                  25

<210> SEQ ID NO 141
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 141

Ala Gly Asp Gly Thr Phe Thr Ser Asp Leu Ser Lys Gln Met Glu Ala
```

```
                1               5                  10                  15

Glu Ala Val Arg Leu Phe Ile Glu Trp Leu Lys Asn
            20                  25

<210> SEQ ID NO 142
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 142

Ala Gly Asp Gly Thr Phe Thr Ser Asp Leu Ser Lys Gln Leu Glu Ala
1               5                   10                  15

Glu Ala Val Arg Leu Phe Ile Glu Phe Leu Lys Asn
            20                  25

<210> SEQ ID NO 143
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 143

Ala Gly Asp Gly Thr Phe Thr Ser Asp Leu Ser Lys Gln Met Glu Glu
1               5                   10                  15

Ala Ala Val Arg Leu Phe Ile Glu Trp Leu Lys Asn
            20                  25

<210> SEQ ID NO 144
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 144

Ala Gly Asp Gly Thr Phe Thr Ser Asp Leu Ser Lys Gln Leu Glu Glu
1               5                   10                  15

Ala Ala Val Arg Leu Phe Ile Glu Phe Leu Lys Asn
            20                  25

<210> SEQ ID NO 145
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 145

Ala Gly Asp Gly Thr Phe Thr Ser Asp Leu Ser Lys Gln Met Glu Glu
```

```
                1               5                  10                 15
Glu Ala Ala Arg Leu Phe Ile Glu Trp Leu Lys Asn
            20                  25

<210> SEQ ID NO 146
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 146

Ala Gly Asp Gly Thr Phe Thr Ser Asp Leu Ser Lys Gln Leu Glu Glu
1               5                   10                  15

Glu Ala Ala Arg Leu Phe Ile Glu Phe Leu Lys Asn
            20                  25

<210> SEQ ID NO 147
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 147

Ala Gly Asp Gly Thr Phe Thr Ser Asp Leu Ser Lys Gln Met Glu Glu
1               5                   10                  15

Glu Ala Val Ala Leu Phe Ile Glu Trp Leu Lys Asn
            20                  25

<210> SEQ ID NO 148
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 148

Ala Gly Asp Gly Thr Phe Thr Ser Asp Leu Ser Lys Gln Leu Glu Glu
1               5                   10                  15

Glu Ala Val Ala Leu Phe Ile Glu Phe Leu Lys Asn
            20                  25

<210> SEQ ID NO 149
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 149

Ala Gly Asp Gly Thr Phe Thr Ser Asp Leu Ser Lys Gln Met Glu Glu
```

```
1               5                   10                  15

Glu Ala Val Arg Ala Phe Ile Glu Trp Leu Lys Asn
            20                  25

<210> SEQ ID NO 150
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 150

Ala Gly Asp Gly Thr Phe Thr Ser Asp Leu Ser Lys Gln Leu Glu Glu
1               5                   10                  15

Glu Ala Val Arg Ala Phe Ile Glu Phe Leu Lys Asn
            20                  25

<210> SEQ ID NO 151
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (22)..(22)
<223> OTHER INFORMATION: naphthylalanine
<220> FEATURE:
<221> NAME/KEY: MOD_RES
<222> LOCATION: (28)..(28)
<223> OTHER INFORMATION: AMIDATION

<400> SEQUENCE: 151

Ala Gly Asp Gly Thr Phe Thr Ser Asp Leu Ser Lys Gln Met Glu Glu
1               5                   10                  15

Glu Ala Val Arg Leu Ala Ile Glu Trp Leu Lys Asn
            20                  25

<210> SEQ ID NO 152
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (22)..(22)
<223> OTHER INFORMATION: naphthylalanine
<220> FEATURE:
<221> NAME/KEY: MOD_RES
<222> LOCATION: (28)..(28)
<223> OTHER INFORMATION: AMIDATION

<400> SEQUENCE: 152

Ala Gly Asp Gly Thr Phe Thr Ser Asp Leu Ser Lys Gln Leu Glu Glu
1               5                   10                  15

Glu Ala Val Arg Leu Ala Ile Glu Phe Leu Lys Asn
            20                  25

<210> SEQ ID NO 153
<211> LENGTH: 28
<212> TYPE: PRT
<213> ORGANISM: Artificial Sequence
<220> FEATURE:
<223> OTHER INFORMATION: Synthetic construct
```

```
<220> FEATURE:
<221> NAME/KEY: MOD_RES
<222> LOCATION: (28)..(28)
<223> OTHER INFORMATION: AMIDATION

<400> SEQUENCE: 153

Ala Gly Asp Gly Thr Phe Thr Ser Asp Leu Ser Lys Gln Met Glu Glu
1               5                   10                  15

Glu Ala Val Arg Leu Phe Val Glu Trp Leu Lys Asn
            20                  25

<210> SEQ ID NO 154
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 154

Ala Gly Asp Gly Thr Phe Thr Ser Asp Leu Ser Lys Gln Leu Glu Glu
1               5                   10                  15

Glu Ala Val Arg Leu Phe Val Glu Phe Leu Lys Asn
            20                  25

<210> SEQ ID NO 155
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (23)..(23)
<223> OTHER INFORMATION: t-butylglycine
<220> FEATURE:
<221> NAME/KEY: MOD_RES
<222> LOCATION: (28)..(28)
<223> OTHER INFORMATION: AMIDATION

<400> SEQUENCE: 155

Ala Gly Asp Gly Thr Phe Thr Ser Asp Leu Ser Lys Gln Met Glu Glu
1               5                   10                  15

Glu Ala Val Arg Leu Phe Gly Glu Trp Leu Lys Asn
            20                  25

<210> SEQ ID NO 156
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (23)..(23)
<223> OTHER INFORMATION: t-butylglycine
<220> FEATURE:
<221> NAME/KEY: MOD_RES
<222> LOCATION: (28)..(28)
<223> OTHER INFORMATION: AMIDATION

<400> SEQUENCE: 156

Ala Gly Asp Gly Thr Phe Thr Ser Asp Leu Ser Lys Gln Leu Glu Glu
1               5                   10                  15

Glu Ala Val Arg Leu Phe Gly Glu Phe Leu Lys Asn
            20                  25
```

```
<210> SEQ ID NO 157
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 157

Ala Gly Asp Gly Thr Phe Thr Ser Asp Leu Ser Lys Gln Met Glu Glu
1               5                   10                  15

Glu Ala Val Arg Leu Phe Ile Asp Trp Leu Lys Asn
            20                  25

<210> SEQ ID NO 158
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 158

Ala Gly Asp Gly Thr Phe Thr Ser Asp Leu Ser Lys Gln Leu Glu Glu
1               5                   10                  15

Glu Ala Val Arg Leu Phe Ile Asp Phe Leu Lys Asn
            20                  25

<210> SEQ ID NO 159
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 159

Ala Gly Asp Gly Thr Phe Thr Ser Asp Leu Ser Lys Gln Met Glu Glu
1               5                   10                  15

Glu Ala Val Arg Leu Phe Ile Glu Ala Leu Lys Asn
            20                  25

<210> SEQ ID NO 160
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 160

Ala Gly Asp Gly Thr Phe Thr Ser Asp Leu Ser Lys Gln Leu Glu Glu
1               5                   10                  15

Glu Ala Val Arg Leu Phe Ile Glu Ala Leu Lys Asn
            20                  25
```

```
<210> SEQ ID NO 161
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 161

Ala Gly Asp Gly Thr Phe Thr Ser Asp Leu Ser Lys Gln Met Glu Glu
1               5                   10                  15

Glu Ala Val Arg Leu Phe Ile Glu Trp Ala Lys Asn
            20                  25

<210> SEQ ID NO 162
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 162

Ala Gly Asp Gly Thr Phe Thr Ser Asp Leu Ser Lys Gln Leu Glu Glu
1               5                   10                  15

Glu Ala Val Arg Leu Phe Ile Glu Phe Ala Lys Asn
            20                  25

<210> SEQ ID NO 163
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 163

Ala Gly Asp Gly Thr Phe Thr Ser Asp Leu Ser Lys Gln Met Glu Glu
1               5                   10                  15

Glu Ala Val Arg Leu Phe Ile Glu Trp Leu Ala Asn
            20                  25

<210> SEQ ID NO 164
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 164

Ala Gly Asp Gly Thr Phe Thr Ser Asp Leu Ser Lys Gln Leu Glu Glu
1               5                   10                  15

Glu Ala Val Arg Leu Phe Ile Glu Phe Leu Ala Asn
            20                  25
```

```
<210> SEQ ID NO 165
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 165

Ala Gly Asp Gly Thr Phe Thr Ser Asp Leu Ser Lys Gln Met Glu Glu
1               5                   10                  15

Glu Ala Val Arg Leu Phe Ile Glu Trp Leu Lys Ala
            20                  25

<210> SEQ ID NO 166
<211> LENGTH: 28
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (28)..(28)
<223> OTHER INFORMATION: AMIDATION

<400> SEQUENCE: 166

Ala Gly Asp Gly Thr Phe Thr Ser Asp Leu Ser Lys Gln Leu Glu Glu
1               5                   10                  15

Glu Ala Val Arg Leu Phe Ile Glu Phe Leu Lys Ala
            20                  25

<210> SEQ ID NO 167
<211> LENGTH: 38
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (38)..(38)
<223> OTHER INFORMATION: AMIDATION

<400> SEQUENCE: 167

Ala Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro
        35

<210> SEQ ID NO 168
<211> LENGTH: 38
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (38)..(38)
<223> OTHER INFORMATION: AMIDATION

<400> SEQUENCE: 168

His Gly Ala Gly Thr Phe Thr Ser Asp Leu Ser Lys Gln Leu Glu Glu
1               5                   10                  15
```

```
Glu Ala Val Arg Leu Phe Ile Glu Phe Leu Lys Asn Gly Gly Pro Ser
            20                  25                  30

Ser Gly Ala Pro Pro Pro
        35
```

<210> SEQ ID NO 169
<211> LENGTH: 37
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (37)..(37)
<223> OTHER INFORMATION: AMIDATION

<400> SEQUENCE: 169

```
His Gly Glu Ala Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro
        35
```

<210> SEQ ID NO 170
<211> LENGTH: 36
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (36)..(36)
<223> OTHER INFORMATION: AMIDATION

<400> SEQUENCE: 170

```
His Gly Glu Gly Thr Phe Thr Ser Ala Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro
        35
```

<210> SEQ ID NO 171
<211> LENGTH: 36
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (36)..(36)
<223> OTHER INFORMATION: AMIDATION

<400> SEQUENCE: 171

```
Ala Gly Glu Gly Thr Phe Thr Ser Asp Ala Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro
        35
```

<210> SEQ ID NO 172
<211> LENGTH: 35
<212> TYPE: PRT

<213> ORGANISM: Artificial Sequence
<220> FEATURE:
<223> OTHER INFORMATION: Synthetic construct
<220> FEATURE:
<221> NAME/KEY: MOD_RES
<222> LOCATION: (35)..(35)
<223> OTHER INFORMATION: AMIDATION

<400> SEQUENCE: 172

Ala Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala
        35

<210> SEQ ID NO 173
<211> LENGTH: 35
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (35)..(35)
<223> OTHER INFORMATION: AMIDATION

<400> SEQUENCE: 173

His Gly Ala Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala
        35

<210> SEQ ID NO 174
<211> LENGTH: 34
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (34)..(34)
<223> OTHER INFORMATION: AMIDATION

<400> SEQUENCE: 174

His Gly Glu Ala Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly

<210> SEQ ID NO 175
<211> LENGTH: 33
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (33)..(33)
<223> OTHER INFORMATION: AMIDATION

<400> SEQUENCE: 175

His Gly Glu Gly Thr Phe Thr Ser Ala Leu Ser Lys Gln Met Glu Glu
1               5                   10                  15

-continued

Glu Ala Val Arg Leu Phe Ile Glu Trp Leu Lys Asn Gly Gly Pro Ser
            20                  25                  30

Ser

<210> SEQ ID NO 176
<211> LENGTH: 32
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (32)..(32)
<223> OTHER INFORMATION: AMIDATION

<400> SEQUENCE: 176

Ala Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

<210> SEQ ID NO 177
<211> LENGTH: 32
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (32)..(32)
<223> OTHER INFORMATION: AMIDATION

<400> SEQUENCE: 177

His Gly Ala Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

<210> SEQ ID NO 178
<211> LENGTH: 31
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (31)..(31)
<223> OTHER INFORMATION: AMIDATION

<400> SEQUENCE: 178

His Gly Glu Ala Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro
            20                  25                  30

<210> SEQ ID NO 179
<211> LENGTH: 30
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (30)..(30)
<223> OTHER INFORMATION: AMIDATION

<400> SEQUENCE: 179

His Gly Glu Gly Thr Phe Thr Ser Ala Leu Ser Lys Gln Leu Glu Glu
1               5                   10                  15

Glu Ala Val Arg Leu Phe Ile Glu Phe Leu Lys Asn Gly Gly
            20                  25                  30

<210> SEQ ID NO 180
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (29)..(29)
<223> OTHER INFORMATION: AMIDATION

<400> SEQUENCE: 180

Ala Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly
            20                  25

<210> SEQ ID NO 181
<211> LENGTH: 38
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (31)..(31)
<223> OTHER INFORMATION: thioproline
<220> FEATURE:
<221> NAME/KEY: MOD_RES
<222> LOCATION: (36)..(38)
<223> OTHER INFORMATION: thioproline
<220> FEATURE:
<221> NAME/KEY: MOD_RES
<222> LOCATION: (38)..(38)
<223> OTHER INFORMATION: AMIDATION

<400> SEQUENCE: 181

His Gly Ala Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro
        35

<210> SEQ ID NO 182
<211> LENGTH: 38
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (36)..(38)
<223> OTHER INFORMATION: thioproline
<220> FEATURE:
<221> NAME/KEY: MOD_RES
<222> LOCATION: (38)..(38)
<223> OTHER INFORMATION: AMIDATION

<400> SEQUENCE: 182

His Gly Glu Ala Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

```
Ser Gly Ala Pro Pro Pro
        35

<210> SEQ ID NO 183
<211> LENGTH: 37
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (31)..(31)
<223> OTHER INFORMATION: N-methylalanine
<220> FEATURE:
<221> NAME/KEY: MOD_RES
<222> LOCATION: (36)..(37)
<223> OTHER INFORMATION: N-methylalanine
<220> FEATURE:
<221> NAME/KEY: MOD_RES
<222> LOCATION: (37)..(37)
<223> OTHER INFORMATION: AMIDATION

<400> SEQUENCE: 183

His Gly Glu Gly Thr Phe Thr Ser Ala Leu Ser Lys Gln Met Glu Glu
1               5                   10                  15

Glu Ala Val Arg Leu Phe Ile Glu Trp Leu Lys Asn Gly Gly Ala Ser
            20                  25                  30

Ser Gly Ala Ala Ala
        35

<210> SEQ ID NO 184
<211> LENGTH: 36
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (31)..(31)
<223> OTHER INFORMATION: homoproline
<220> FEATURE:
<221> NAME/KEY: MOD_RES
<222> LOCATION: (36)..(36)
<223> OTHER INFORMATION: AMIDATION
<220> FEATURE:
<221> NAME/KEY: MOD_RES
<222> LOCATION: (36)..(36)
<223> OTHER INFORMATION: homoproline

<400> SEQUENCE: 184

Ala Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro
        35

<210> SEQ ID NO 185
<211> LENGTH: 35
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (35)..(35)
<223> OTHER INFORMATION: AMIDATION

<400> SEQUENCE: 185
```

His Gly Ala Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala
        35

<210> SEQ ID NO 186
<211> LENGTH: 30
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (30)..(30)
<223> OTHER INFORMATION: AMIDATION

<400> SEQUENCE: 186

His Gly Asp Ala Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30

<210> SEQ ID NO 187
<211> LENGTH: 39
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (39)..(39)
<223> OTHER INFORMATION: AMIDATION

<400> SEQUENCE: 187

Ala Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 188
<211> LENGTH: 39
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (39)..(39)
<223> OTHER INFORMATION: AMIDATION

<400> SEQUENCE: 188

Ala Gly Ala Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro Ser
        35

<210> SEQ ID NO 189
<211> LENGTH: 36
<212> TYPE: PRT
<213> ORGANISM: Artificial Sequence

```
<220> FEATURE:
<223> OTHER INFORMATION: Synthetic construct

<400> SEQUENCE: 189

Ala Pro Leu Glu Pro Val Tyr Pro Gly Asp Asn Ala Thr Pro Glu Gln
1               5                   10                  15

Met Ala Gln Tyr Ala Ala Asp Leu Arg Arg Tyr Ile Asn Met Leu Thr
                20                  25                  30

Arg Pro Arg Tyr
            35

<210> SEQ ID NO 190
<211> LENGTH: 36
<212> TYPE: PRT
<213> ORGANISM: Homo sapien

<400> SEQUENCE: 190

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
                20                  25                  30

Arg Gln Arg Tyr
            35

<210> SEQ ID NO 191
<211> LENGTH: 34
<212> TYPE: PRT
<213> ORGANISM: Artificial Sequence
<220> FEATURE:
<223> OTHER INFORMATION: Synthetic construct

<400> SEQUENCE: 191

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
                20                  25                  30

Arg Tyr

<210> SEQ ID NO 192
<211> LENGTH: 36
<212> TYPE: PRT
<213> ORGANISM: Artificial Sequence
<220> FEATURE:
<223> OTHER INFORMATION: Synthetic construct

<400> SEQUENCE: 192

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
                20                  25                  30

Arg Gln Arg Tyr
            35

<210> SEQ ID NO 193
<211> LENGTH: 34
<212> TYPE: PRT
<213> ORGANISM: Artificial Sequence
<220> FEATURE:
<223> OTHER INFORMATION: Synthetic construct

<400> SEQUENCE: 193

Ser Lys Pro Asp Asn Pro Gly Glu Asp Ala Pro Ala Glu Asp Met Ala
1               5                   10                  15
```

```
Arg Tyr Tyr Ser Ala Leu Arg His Tyr Ile Asn Leu Ile Thr Arg Gln
            20                  25                  30

Arg Tyr

<210> SEQ ID NO 194
<211> LENGTH: 15
<212> TYPE: PRT
<213> ORGANISM: Artificial Sequence
<220> FEATURE:
<223> OTHER INFORMATION: Synthetic construct

<400> SEQUENCE: 194

Ala Ser Leu Arg His Tyr Leu Asn Leu Val Thr Arg Gln Arg Tyr
1               5                   10                  15

<210> SEQ ID NO 195
<211> LENGTH: 31
<212> TYPE: PRT
<213> ORGANISM: Artificial Sequence
<220> FEATURE:
<223> OTHER INFORMATION: Synthetic construct

<400> SEQUENCE: 195

His Val Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly
            20                  25                  30

<210> SEQ ID NO 196
<211> LENGTH: 31
<212> TYPE: PRT
<213> ORGANISM: Artificial Sequence
<220> FEATURE:
<223> OTHER INFORMATION: Synthetic construct

<400> SEQUENCE: 196

His Val Glu Gly Thr Phe Thr Ser Asp Val Ser Ser Tyr Leu Glu Asp
1               5                   10                  15

Gln Ala Ala Lys Glu Phe Ile Ala Trp Leu Val Lys Gly Arg Gly
            20                  25                  30

<210> SEQ ID NO 197
<211> LENGTH: 31
<212> TYPE: PRT
<213> ORGANISM: Artificial Sequence
<220> FEATURE:
<223> OTHER INFORMATION: Synthetic construct

<400> SEQUENCE: 197

His Val Glu Gly Thr Phe Thr Ser Asp Val Ser Ser Tyr Leu Glu Arg
1               5                   10                  15

Gln Ala Ala Lys Glu Phe Ile Ala Trp Leu Val Lys Gly Arg Gly
            20                  25                  30

<210> SEQ ID NO 198
<211> LENGTH: 31
<212> TYPE: PRT
<213> ORGANISM: Artificial Sequence
<220> FEATURE:
<223> OTHER INFORMATION: Synthetic construct

<400> SEQUENCE: 198

His Val Glu Gly Thr Phe Thr Ser Asp Val Ser Ser Tyr Leu Glu Lys
1               5                   10                  15
```

```
Gln Ala Ala Lys Glu Phe Ile Ala Trp Leu Val Lys Gly Arg Gly
         20                  25                  30

<210> SEQ ID NO 199
<211> LENGTH: 31
<212> TYPE: PRT
<213> ORGANISM: Artificial Sequence
<220> FEATURE:
<223> OTHER INFORMATION: Synthetic construct

<400> SEQUENCE: 199

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly
         20                  25                  30

<210> SEQ ID NO 200
<211> LENGTH: 31
<212> TYPE: PRT
<213> ORGANISM: Artificial Sequence
<220> FEATURE:
<223> OTHER INFORMATION: Synthetic construct

<400> SEQUENCE: 200

His Gly Glu Gly Thr Phe Thr Ser Asp Val Ser Ser Tyr Leu Glu Asp
1               5                   10                  15

Gln Ala Ala Lys Glu Phe Ile Ala Trp Leu Val Lys Gly Arg Gly
         20                  25                  30

<210> SEQ ID NO 201
<211> LENGTH: 31
<212> TYPE: PRT
<213> ORGANISM: Artificial Sequence
<220> FEATURE:
<223> OTHER INFORMATION: Synthetic construct

<400> SEQUENCE: 201

His Gly Glu Gly Thr Phe Thr Ser Asp Val Ser Ser Tyr Leu Glu Arg
1               5                   10                  15

Gln Ala Ala Lys Glu Phe Ile Ala Trp Leu Val Lys Gly Arg Gly
         20                  25                  30

<210> SEQ ID NO 202
<211> LENGTH: 31
<212> TYPE: PRT
<213> ORGANISM: Artificial Sequence
<220> FEATURE:
<223> OTHER INFORMATION: Synthetic construct

<400> SEQUENCE: 202

His Gly Glu Gly Thr Phe Thr Ser Asp Val Ser Ser Tyr Leu Glu Lys
1               5                   10                  15

Gln Ala Ala Lys Glu Phe Ile Ala Trp Leu Val Lys Gly Arg Gly
         20                  25                  30

<210> SEQ ID NO 203
<211> LENGTH: 31
<212> TYPE: PRT
<213> ORGANISM: Artificial Sequence
<220> FEATURE:
<223> OTHER INFORMATION: Synthetic construct

<400> SEQUENCE: 203

His Val Glu Gly Thr Phe Thr Ser Asp Val Ser Ser Tyr Leu Glu Gly
1               5                   10                  15
```

```
Gln Ala Ala Lys Glu Phe Ile Glu Trp Leu Val Lys Gly Arg Gly
            20                  25                  30
```

<210> SEQ ID NO 204
<211> LENGTH: 31
<212> TYPE: PRT
<213> ORGANISM: Artificial Sequence
<220> FEATURE:
<223> OTHER INFORMATION: Synthetic construct

<400> SEQUENCE: 204

```
His Gly Glu Gly Thr Phe Thr Ser Asp Val Ser Ser Tyr Leu Glu Gly
1               5                   10                  15

Gln Ala Ala Lys Glu Phe Ile Glu Trp Leu Val Lys Gly Arg Gly
            20                  25                  30
```

<210> SEQ ID NO 205
<211> LENGTH: 31
<212> TYPE: PRT
<213> ORGANISM: Artificial Sequence
<220> FEATURE:
<223> OTHER INFORMATION: Synthetic construct

<400> SEQUENCE: 205

```
His Val Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg His
            20                  25                  30
```

<210> SEQ ID NO 206
<211> LENGTH: 31
<212> TYPE: PRT
<213> ORGANISM: Artificial Sequence
<220> FEATURE:
<223> OTHER INFORMATION: Synthetic construct

<400> SEQUENCE: 206

```
His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg His
            20                  25                  30
```

<210> SEQ ID NO 207
<211> LENGTH: 31
<212> TYPE: PRT
<213> ORGANISM: Artificial Sequence
<220> FEATURE:
<223> OTHER INFORMATION: Synthetic construct

<400> SEQUENCE: 207

```
His Val Glu Gly Thr Phe Thr Ser Asp Val Ser Ser Tyr Leu Glu Glu
1               5                   10                  15

Gln Ala Ala Lys Ala Phe Ile Ala Trp Leu Val Lys Gly Arg His
            20                  25                  30
```

<210> SEQ ID NO 208
<211> LENGTH: 31
<212> TYPE: PRT
<213> ORGANISM: Artificial Sequence
<220> FEATURE:
<223> OTHER INFORMATION: Synthetic construct

<400> SEQUENCE: 208

```
His Val Glu Gly Thr Phe Thr Ser Asp Val Ser Ser Tyr Leu Glu Lys
1               5                   10                  15
```

```
Glu Ala Ala Lys Glu Phe Ile Ala Trp Leu Val Lys Gly Arg His
            20                  25                  30
```

<210> SEQ ID NO 209
<211> LENGTH: 31
<212> TYPE: PRT
<213> ORGANISM: Artificial Sequence
<220> FEATURE:
<223> OTHER INFORMATION: Synthetic construct

<400> SEQUENCE: 209

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30
```

<210> SEQ ID NO 210
<211> LENGTH: 31
<212> TYPE: PRT
<213> ORGANISM: Artificial Sequence
<220> FEATURE:
<223> OTHER INFORMATION: Synthetic construct

<400> SEQUENCE: 210

```
His Ala Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg Gly
            20                  25                  30
```

<210> SEQ ID NO 211
<211> LENGTH: 31
<212> TYPE: PRT
<213> ORGANISM: Artificial Sequence
<220> FEATURE:
<223> OTHER INFORMATION: Synthetic construct

<400> SEQUENCE: 211

```
His Ala Glu Gly Thr Phe Thr Ser Asp Val Ser Ser Tyr Leu Glu Asp
1               5                   10                  15

Gln Ala Ala Lys Glu Phe Ile Ala Trp Leu Val Lys Gly Arg Gly
            20                  25                  30
```

<210> SEQ ID NO 212
<211> LENGTH: 31
<212> TYPE: PRT
<213> ORGANISM: Artificial Sequence
<220> FEATURE:
<223> OTHER INFORMATION: Synthetic construct

<400> SEQUENCE: 212

```
His Ala Glu Gly Thr Phe Thr Ser Asp Val Ser Ser Tyr Leu Glu Arg
1               5                   10                  15

Gln Ala Ala Lys Glu Phe Ile Ala Trp Leu Val Lys Gly Arg Gly
            20                  25                  30
```

<210> SEQ ID NO 213
<211> LENGTH: 31
<212> TYPE: PRT
<213> ORGANISM: Artificial Sequence
<220> FEATURE:
<223> OTHER INFORMATION: Synthetic construct

<400> SEQUENCE: 213

```
His Ala Glu Gly Thr Phe Thr Ser Asp Val Ser Ser Tyr Leu Glu Lys
1               5                   10                  15
```

Gln Ala Ala Lys Glu Phe Ile Ala Trp Leu Val Lys Gly Arg Gly
            20                  25                  30

<210> SEQ ID NO 214
<211> LENGTH: 31
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (16)..(16)

<400> SEQUENCE: 214

His Ala Glu Gly Thr Phe Thr Ser Asp Val Ser Ser Tyr Leu Glu Ala
1               5                   10                  15

Gln Ala Ala Lys Glu Phe Ile Ala Trp Leu Val Lys Gly Arg Gly
            20                  25                  30

<210> SEQ ID NO 215
<211> LENGTH: 31
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (16)..(16)

<400> SEQUENCE: 215

His Val Glu Gly Thr Phe Thr Ser Asp Val Ser Ser Tyr Leu Glu Ala
1               5                   10                  15

Gln Ala Ala Lys Glu Phe Ile Ala Trp Leu Val Lys Gly Arg Gly
            20                  25                  30

<210> SEQ ID NO 216
<211> LENGTH: 31
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (16)..(16)

<400> SEQUENCE: 216

His Gly Glu Gly Thr Phe Thr Ser Asp Val Ser Ser Tyr Leu Glu Ala
1               5                   10                  15

Gln Ala Ala Lys Glu Phe Ile Ala Trp Leu Val Lys Gly Arg Gly
            20                  25                  30

<210> SEQ ID NO 217
<211> LENGTH: 30
<212> TYPE: PRT
<213> ORGANISM: Artificial Sequence
<220> FEATURE:
<223> OTHER INFORMATION: Synthetic construct

<400> SEQUENCE: 217

His Ala Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg
            20                  25                  30

<210> SEQ ID NO 218
<211> LENGTH: 30
<212> TYPE: PRT

-continued

```
<213> ORGANISM: Artificial Sequence
<220> FEATURE:
<223> OTHER INFORMATION: Synthetic construct

<400> SEQUENCE: 218

His Ala Glu Gly Thr Phe Thr Ser Asp Val Ser Ser Tyr Leu Glu Asp
1               5                   10                  15

Gln Ala Ala Lys Glu Phe Ile Ala Trp Leu Val Lys Gly Arg
            20                  25                  30

<210> SEQ ID NO 219
<211> LENGTH: 30
<212> TYPE: PRT
<213> ORGANISM: Artificial Sequence
<220> FEATURE:
<223> OTHER INFORMATION: Synthetic construct

<400> SEQUENCE: 219

His Ala Glu Gly Thr Phe Thr Ser Asp Val Ser Ser Tyr Leu Glu Arg
1               5                   10                  15

Gln Ala Ala Lys Glu Phe Ile Ala Trp Leu Val Lys Gly Arg
            20                  25                  30

<210> SEQ ID NO 220
<211> LENGTH: 30
<212> TYPE: PRT
<213> ORGANISM: Artificial Sequence
<220> FEATURE:
<223> OTHER INFORMATION: Synthetic construct

<400> SEQUENCE: 220

His Ala Glu Gly Thr Phe Thr Ser Asp Val Ser Ser Tyr Leu Glu Lys
1               5                   10                  15

Gln Ala Ala Lys Glu Phe Ile Ala Trp Leu Val Lys Gly Arg
            20                  25                  30

<210> SEQ ID NO 221
<211> LENGTH: 30
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (16)..(16)

<400> SEQUENCE: 221

His Ala Glu Gly Thr Phe Thr Ser Asp Val Ser Ser Tyr Leu Glu Ala
1               5                   10                  15

Gln Ala Ala Lys Glu Phe Ile Ala Trp Leu Val Lys Gly Arg
            20                  25                  30

<210> SEQ ID NO 222
<211> LENGTH: 30
<212> TYPE: PRT
<213> ORGANISM: Artificial Sequence
<220> FEATURE:
<223> OTHER INFORMATION: Synthetic construct

<400> SEQUENCE: 222

His Val Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg
            20                  25                  30
```

```
<210> SEQ ID NO 223
<211> LENGTH: 30
<212> TYPE: PRT
<213> ORGANISM: Artificial Sequence
<220> FEATURE:
<223> OTHER INFORMATION: Synthetic construct

<400> SEQUENCE: 223

His Val Glu Gly Thr Phe Thr Ser Asp Val Ser Ser Tyr Leu Glu Asp
1               5                   10                  15

Gln Ala Ala Lys Glu Phe Ile Ala Trp Leu Val Lys Gly Arg
            20                  25                  30

<210> SEQ ID NO 224
<211> LENGTH: 30
<212> TYPE: PRT
<213> ORGANISM: Artificial Sequence
<220> FEATURE:
<223> OTHER INFORMATION: Synthetic construct

<400> SEQUENCE: 224

His Val Glu Gly Thr Phe Thr Ser Asp Val Ser Ser Tyr Leu Glu Arg
1               5                   10                  15

Gln Ala Ala Lys Glu Phe Ile Ala Trp Leu Val Lys Gly Arg
            20                  25                  30

<210> SEQ ID NO 225
<211> LENGTH: 30
<212> TYPE: PRT
<213> ORGANISM: Artificial Sequence
<220> FEATURE:
<223> OTHER INFORMATION: Synthetic construct

<400> SEQUENCE: 225

His Val Glu Gly Thr Phe Thr Ser Asp Val Ser Ser Tyr Leu Glu Lys
1               5                   10                  15

Gln Ala Ala Lys Glu Phe Ile Ala Trp Leu Val Lys Gly Arg
            20                  25                  30

<210> SEQ ID NO 226
<211> LENGTH: 30
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (16)..(16)

<400> SEQUENCE: 226

His Val Glu Gly Thr Phe Thr Ser Asp Val Ser Ser Tyr Leu Glu Ala
1               5                   10                  15

Gln Ala Ala Lys Glu Phe Ile Ala Trp Leu Val Lys Gly Arg
            20                  25                  30

<210> SEQ ID NO 227
<211> LENGTH: 30
<212> TYPE: PRT
<213> ORGANISM: Artificial Sequence
<220> FEATURE:
<223> OTHER INFORMATION: Synthetic construct

<400> SEQUENCE: 227

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Arg
```

<210> SEQ ID NO 228
<211> LENGTH: 30
<212> TYPE: PRT
<213> ORGANISM: Artificial Sequence
<220> FEATURE:
<223> OTHER INFORMATION: Synthetic construct

<400> SEQUENCE: 228

His Gly Glu Gly Thr Phe Thr Ser Asp Val Ser Ser Tyr Leu Glu Asp
1               5                   10                  15

Gln Ala Ala Lys Glu Phe Ile Ala Trp Leu Val Lys Gly Arg
            20                  25                  30

<210> SEQ ID NO 229
<211> LENGTH: 30
<212> TYPE: PRT
<213> ORGANISM: Artificial Sequence
<220> FEATURE:
<223> OTHER INFORMATION: Synthetic construct

<400> SEQUENCE: 229

His Gly Glu Gly Thr Phe Thr Ser Asp Val Ser Ser Tyr Leu Glu Arg
1               5                   10                  15

Gln Ala Ala Lys Glu Phe Ile Ala Trp Leu Val Lys Gly Arg
            20                  25                  30

<210> SEQ ID NO 230
<211> LENGTH: 30
<212> TYPE: PRT
<213> ORGANISM: Artificial Sequence
<220> FEATURE:
<223> OTHER INFORMATION: Synthetic construct

<400> SEQUENCE: 230

His Gly Glu Gly Thr Phe Thr Ser Asp Val Ser Ser Tyr Leu Glu Lys
1               5                   10                  15

Gln Ala Ala Lys Glu Phe Ile Ala Trp Leu Val Lys Gly Arg
            20                  25                  30

<210> SEQ ID NO 231
<211> LENGTH: 30
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (16)..(16)

<400> SEQUENCE: 231

His Gly Glu Gly Thr Phe Thr Ser Asp Val Ser Ser Tyr Leu Glu Ala
1               5                   10                  15

Gln Ala Ala Lys Glu Phe Ile Ala Trp Leu Val Lys Gly Arg
            20                  25                  30

<210> SEQ ID NO 232
<211> LENGTH: 31
<212> TYPE: PRT
<213> ORGANISM: Artificial Sequence
<220> FEATURE:
<223> OTHER INFORMATION: Synthetic construct

<400> SEQUENCE: 232

His Val Glu Gly Thr Phe Thr Ser Asp Val Ser Ser Tyr Leu Glu Gly

-continued

```
                1               5                   10                  15
Lys Ala Ala Lys Glu Phe Ile Ala Trp Leu Val Lys Gly Arg Gly
            20                  25                  30

<210> SEQ ID NO 233
<211> LENGTH: 31
<212> TYPE: PRT
<213> ORGANISM: Artificial Sequence
<220> FEATURE:
<223> OTHER INFORMATION: Synthetic construct

<400> SEQUENCE: 233

His Val Glu Gly Thr Phe Thr Ser Asp Val Ser Ser Tyr Leu Glu Gly
1               5                   10                  15
Gln Ala Ala Lys Ala Phe Ile Ala Trp Leu Val Lys Gly Arg Gly
            20                  25                  30

<210> SEQ ID NO 234
<211> LENGTH: 31
<212> TYPE: PRT
<213> ORGANISM: Artificial Sequence
<220> FEATURE:
<223> OTHER INFORMATION: Synthetic construct

<400> SEQUENCE: 234

His Val Glu Gly Thr Phe Thr Ser Asp Val Ser Ser Tyr Leu Glu Gly
1               5                   10                  15
Gln Ala Ala Lys Glu Phe Ile Glu Trp Leu Val Lys Gly Arg Gly
            20                  25                  30

<210> SEQ ID NO 235
<211> LENGTH: 31
<212> TYPE: PRT
<213> ORGANISM: Artificial Sequence
<220> FEATURE:
<223> OTHER INFORMATION: Synthetic construct

<400> SEQUENCE: 235

His Gly Glu Gly Thr Phe Thr Ser Asp Val Ser Ser Tyr Leu Glu Gly
1               5                   10                  15
Gln Ala Ala Lys Glu Phe Ile Glu Trp Leu Val Lys Gly Arg Gly
            20                  25                  30

<210> SEQ ID NO 236
<211> LENGTH: 31
<212> TYPE: PRT
<213> ORGANISM: Artificial Sequence
<220> FEATURE:
<223> OTHER INFORMATION: Synthetic construct

<400> SEQUENCE: 236

His Val Glu Gly Thr Phe Thr Ser Asp Val Ser Ser Tyr Leu Glu Gly
1               5                   10                  15
Gln Ala Ala Lys Glu Phe Ile Ala Trp Leu Val Lys His Arg Gly
            20                  25                  30

<210> SEQ ID NO 237
<211> LENGTH: 31
<212> TYPE: PRT
<213> ORGANISM: Artificial Sequence
<220> FEATURE:
<223> OTHER INFORMATION: Synthetic construct

<400> SEQUENCE: 237

His Val Glu Gly Thr Phe Thr Ser Asp Val Ser Ser Tyr Leu Glu Gly
```

```
                1               5                  10                 15
Gln Ala Ala Lys Glu Phe Ile Ala Trp Leu Val Lys Gly Arg His
                20                  25                 30

<210> SEQ ID NO 238
<211> LENGTH: 31
<212> TYPE: PRT
<213> ORGANISM: Artificial Sequence
<220> FEATURE:
<223> OTHER INFORMATION: Synthetic construct

<400> SEQUENCE: 238

His Val Glu Gly Thr Phe Thr Ser Asp Val Ser Ser Tyr Leu Glu Glu
1               5                   10                  15

Lys Ala Ala Lys Glu Phe Ile Ala Trp Leu Val Lys Gly Arg Gly
                20                  25                  30

<210> SEQ ID NO 239
<211> LENGTH: 31
<212> TYPE: PRT
<213> ORGANISM: Artificial Sequence
<220> FEATURE:
<223> OTHER INFORMATION: Synthetic construct

<400> SEQUENCE: 239

His Val Glu Gly Thr Phe Thr Ser Asp Val Ser Ser Tyr Leu Glu Glu
1               5                   10                  15

Glu Ala Ala Lys Glu Phe Ile Ala Trp Leu Val Lys Gly Arg Gly
                20                  25                  30

<210> SEQ ID NO 240
<211> LENGTH: 31
<212> TYPE: PRT
<213> ORGANISM: Artificial Sequence
<220> FEATURE:
<223> OTHER INFORMATION: Synthetic construct

<400> SEQUENCE: 240

His Val Glu Gly Thr Phe Thr Ser Asp Val Ser Ser Tyr Leu Glu Glu
1               5                   10                  15

Gln Ala Ala Lys Ala Phe Ile Ala Trp Leu Val Lys Gly Arg Gly
                20                  25                  30

<210> SEQ ID NO 241
<211> LENGTH: 31
<212> TYPE: PRT
<213> ORGANISM: Artificial Sequence
<220> FEATURE:
<223> OTHER INFORMATION: Synthetic construct

<400> SEQUENCE: 241

His Val Glu Gly Thr Phe Thr Ser Asp Val Ser Ser Tyr Leu Glu Gly
1               5                   10                  15

Gln Ala Ala Lys Glu Phe Ile Ala Trp Leu Val Gly Lys Arg Gly
                20                  25                  30

<210> SEQ ID NO 242
<211> LENGTH: 31
<212> TYPE: PRT
<213> ORGANISM: Artificial Sequence
<220> FEATURE:
<223> OTHER INFORMATION: Synthetic construct

<400> SEQUENCE: 242

His Val Glu Gly Thr Phe Thr Ser Asp Val Ser Ser Tyr Leu Glu Gly
```

-continued

```
                1               5                  10                 15
Gln Ala Ala Lys Glu Phe Ile Ala Trp Leu Val Lys Gly Arg His
                20                 25                 30

<210> SEQ ID NO 243
<211> LENGTH: 31
<212> TYPE: PRT
<213> ORGANISM: Artificial Sequence
<220> FEATURE:
<223> OTHER INFORMATION: Synthetic construct

<400> SEQUENCE: 243

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg His
                20                  25                  30

<210> SEQ ID NO 244
<211> LENGTH: 32
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: (2)..(2)
<223> OTHER INFORMATION: Gly, Ala, Val, Leu, Ile, Ser or Thr
<220> FEATURE:
<221> NAME/KEY: VARIANT
<222> LOCATION: (5)..(5)
<223> OTHER INFORMATION: Asp, Glu, Arg, Thr, Ala, Lys or His
<220> FEATURE:
<221> NAME/KEY: VARIANT
<222> LOCATION: (6)..(6)
<223> OTHER INFORMATION: His, Trp, Phe, or Tyr
<220> FEATURE:
<221> NAME/KEY: VARIANT
<222> LOCATION: (10)..(10)
<223> OTHER INFORMATION: Leu, Ser, Thr, Trp, His, Phe, Asp, Val, Glu or
     Ala
<220> FEATURE:
<221> NAME/KEY: VARIANT
<222> LOCATION: (16)..(16)
<223> OTHER INFORMATION: Gly, Asp, Glu, Gln, Asn, Lys, Arg, Cys or
     cysteic acid
<220> FEATURE:
<221> NAME/KEY: VARIANT
<222> LOCATION: (17)..(17)
<223> OTHER INFORMATION: His, Asp, Lys, Glu, or Gln
<220> FEATURE:
<221> NAME/KEY: VARIANT
<222> LOCATION: (18)..(18)
<223> OTHER INFORMATION: Glu, His, Ala, or Lys
<220> FEATURE:
<221> NAME/KEY: VARIANT
<222> LOCATION: (20)..(20)
<223> OTHER INFORMATION: Asp, Lys, Glu, or His
<220> FEATURE:
<221> NAME/KEY: VARIANT
<222> LOCATION: (21)..(21)
<223> OTHER INFORMATION: Ala, Glu, His, Phe, Try, Trp, Arg, or Lys
<220> FEATURE:
<221> NAME/KEY: VARIANT
<222> LOCATION: (25)..(25)
<223> OTHER INFORMATION: Ala, Glu, Asp, Ser, or His
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: VARIANT
<222> LOCATION: (28)..(28)
<223> OTHER INFORMATION: Glu, Lys, or Asp
<220> FEATURE:
<221> NAME/KEY: VARIANT
```

```
<222> LOCATION: (29)..(29)
<223> OTHER INFORMATION: Thr, Ser, Lys, Arg, Trp, Tyr, Phe, Asp, Gly,
      Pro, His, or Glu
<220> FEATURE:
<221> NAME/KEY: VARIANT
<222> LOCATION: (30)..(30)
<223> OTHER INFORMATION: Arg, Glu or His
<220> FEATURE:
<221> NAME/KEY: VARIANT
<222> LOCATION: (31)..(31)
<223> OTHER INFORMATION: Lys, Arg, Thr, Ser, Glu, Asp, Trp, Tyr, Phe,
      His, Gly or absent and optionally amidated if position 32 absent
<220> FEATURE:
<221> NAME/KEY: VARIANT
<222> LOCATION: (32)..(32)
<223> OTHER INFORMATION: Pro if position 31 is Gly or absent and if
      present is optionally amidated

<400> SEQUENCE: 244

His Xaa Glu Gly Xaa Xaa Thr Ser Asp Xaa Ser Ser Tyr Leu Glu Xaa
1               5                  10                  15

Xaa Xaa Ala Xaa Xaa Phe Ile Ala Xaa Leu Xaa Xaa Xaa Xaa Xaa Xaa
            20                  25                  30

<210> SEQ ID NO 245
<211> LENGTH: 32
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: (2)..(2)
<223> OTHER INFORMATION: Gly, Ala, Val, Leu, Ile, Ser, or Thr
<220> FEATURE:
<221> NAME/KEY: VARIANT
<222> LOCATION: (6)..(6)
<223> OTHER INFORMATION: His, Trp, Phe or Try
<220> FEATURE:
<221> NAME/KEY: VARIANT
<222> LOCATION: (10)..(10)
<223> OTHER INFORMATION: Leu, Ser, Thr, Trp, His, Phe, Asp, Val, Glu, or
      Ala
<220> FEATURE:
<221> NAME/KEY: VARIANT
<222> LOCATION: (16)..(16)
<223> OTHER INFORMATION: Gly, Asp, Glu, Gln, Asn, Lys, Arg, Cys, or
      cysteic acid (3-sulfoalanine)
<220> FEATURE:
<221> NAME/KEY: VARIANT
<222> LOCATION: (17)..(17)
<223> OTHER INFORMATION: His, Asp, Lys, Glu, or Gln
<220> FEATURE:
<221> NAME/KEY: VARIANT
<222> LOCATION: (20)..(20)
<223> OTHER INFORMATION: Asp, Lys, Glu, or His
<220> FEATURE:
<221> NAME/KEY: VARIANT
<222> LOCATION: (24)..(24)
<223> OTHER INFORMATION: Ala, Glu, Asp, Ser, or His
<220> FEATURE:
<221> NAME/KEY: VARIANT
<222> LOCATION: (29)..(29)
<223> OTHER INFORMATION: Thr, Ser, Lys, Arg, Trp, Tyr, Phe, Asp, Gly,
      Pro, His, or Glu
<220> FEATURE:
<221> NAME/KEY: VARIANT
<222> LOCATION: (31)..(31)
<223> OTHER INFORMATION: Lys, Arg, Thr, Ser, Glu, Asp, Trp, Tyr, Phe,
      His, Gly or absent and optionally amidated if position 32 is
      absent
<220> FEATURE:
<221> NAME/KEY: VARIANT
<222> LOCATION: (32)..(32)
<223> OTHER INFORMATION: Pro if position 31 is Gly or absent and if
      present is optionally amidated
```

```
<400> SEQUENCE: 245

His Xaa Glu Gly Thr Xaa Thr Ser Asp Xaa Ser Ser Tyr Leu Glu Xaa
1               5                   10                  15

Xaa Ala Ala Xaa Glu Phe Ile Xaa Trp Leu Val Lys Xaa Arg Xaa Xaa
            20                  25                  30

<210> SEQ ID NO 246
<211> LENGTH: 32
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: (2)..(2)
<223> OTHER INFORMATION: Gly, Ala, Val, Leu, Ile, Ser, or Thr
<220> FEATURE:
<221> NAME/KEY: VARIANT
<222> LOCATION: (16)..(16)
<223> OTHER INFORMATION: Gly, Asp, Glu, Gln, Asn, Lys, Arg, Cys, or
      cysteic acid (3-sulfoalanine)
<220> FEATURE:
<221> NAME/KEY: VARIANT
<222> LOCATION: (17)..(17)
<223> OTHER INFORMATION: His, Asp, Lys, Glu or Gln
<220> FEATURE:
<221> NAME/KEY: VARIANT
<222> LOCATION: (21)..(21)
<223> OTHER INFORMATION: Ala, Glu, His, Phe, Try, Trp, Arg, or Lys
<220> FEATURE:
<221> NAME/KEY: VARIANT
<222> LOCATION: (24)..(24)
<223> OTHER INFORMATION: Ala, Glu, Asp, Ser, or His
<220> FEATURE:
<221> NAME/KEY: VARIANT
<222> LOCATION: (31)..(31)
<223> OTHER INFORMATION: Lys, Arg, Thr, Ser, Glu, Asp, Trp, Tyr, Phe,
      His, Gly or absent and optionally amidated if position 32 is
      absent
<220> FEATURE:
<221> NAME/KEY: VARIANT
<222> LOCATION: (32)..(32)
<223> OTHER INFORMATION: Pro if position 31 is Gly or absent and
      optionally amidated

<400> SEQUENCE: 246

His Xaa Glu Gly Thr Phe Thr Ser Asp Val Ser Ser Tyr Leu Glu Xaa
1               5                   10                  15

Xaa Ala Ala Lys Xaa Phe Ile Xaa Trp Leu Val Lys Gly Arg Xaa Xaa
            20                  25                  30

<210> SEQ ID NO 247
<211> LENGTH: 31
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: (1)..(1)
<223> OTHER INFORMATION: L-histidine, D-histidine, desamino-histidine,
      2amino-histidine, beta-hydroxy-histidine, homohistidine,
      alpha-flurormethyl-histidine or alpha-methyl-histidine
<220> FEATURE:
<221> NAME/KEY: VARIANT
<222> LOCATION: (2)..(2)
<223> OTHER INFORMATION: Gly, Ala, Val, Leu, Ile, Ser or Thr
<220> FEATURE:
<221> NAME/KEY: VARIANT
<222> LOCATION: (16)..(16)
<223> OTHER INFORMATION: Asp, Glu, Gln, Asn, Lys, Arg, Cys, or cysteic
      acid
<220> FEATURE:
<221> NAME/KEY: VARIANT
```

```
<222> LOCATION: (30)..(30)
<223> OTHER INFORMATION: amidated if position 31 is absent
<220> FEATURE:
<221> NAME/KEY: VARIANT
<222> LOCATION: (31)..(31)
<223> OTHER INFORMATION: Gly or absent

<400> SEQUENCE: 247

Xaa Xaa Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Arg Xaa
            20                  25                  30

<210> SEQ ID NO 248
<211> LENGTH: 37
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: (1)..(1)
<223> OTHER INFORMATION: Lys, Ala, Ser or H
<220> FEATURE:
<221> NAME/KEY: VARIANT
<222> LOCATION: (2)..(2)
<223> OTHER INFORMATION: amino acid having side chains chemically bonded
      to amino acid at position 7 to form an intramolecular linkage
<220> FEATURE:
<221> NAME/KEY: VARIANT
<222> LOCATION: (7)..(7)
<223> OTHER INFORMATION: amino acid having side chains chemically bonded
      to amino acid at position 2 to form an intramolecular linkage
<220> FEATURE:
<221> NAME/KEY: VARIANT
<222> LOCATION: (13)..(13)
<223> OTHER INFORMATION: Ala, Ser or Thr
<220> FEATURE:
<221> NAME/KEY: VARIANT
<222> LOCATION: (17)..(17)
<223> OTHER INFORMATION: Val, Leu, or Ile
<220> FEATURE:
<221> NAME/KEY: VARIANT
<222> LOCATION: (18)..(18)
<223> OTHER INFORMATION: His or Arg
<220> FEATURE:
<221> NAME/KEY: VARIANT
<222> LOCATION: (19)..(19)
<223> OTHER INFORMATION: Ser or Thr
<220> FEATURE:
<221> NAME/KEY: VARIANT
<222> LOCATION: (20)..(20)
<223> OTHER INFORMATION: Ser, Thr, Gln, or Asn
<220> FEATURE:
<221> NAME/KEY: VARIANT
<222> LOCATION: (21)..(21)
<223> OTHER INFORMATION: Asn, Gln or His
<220> FEATURE:
<221> NAME/KEY: VARIANT
<222> LOCATION: (23)..(23)
<223> OTHER INFORMATION: Phe, Leu or Tyr
<220> FEATURE:
<221> NAME/KEY: VARIANT
<222> LOCATION: (25)..(25)
<223> OTHER INFORMATION: Ala or Pro
<220> FEATURE:
<221> NAME/KEY: VARIANT
<222> LOCATION: (26)..(26)
<223> OTHER INFORMATION: Ile, Val, Ala, or Leu
<220> FEATURE:
<221> NAME/KEY: VARIANT
<222> LOCATION: (28)..(28)
<223> OTHER INFORMATION: Ser, Pro, Leu, Ile, or Thr
<220> FEATURE:
<221> NAME/KEY: VARIANT
<222> LOCATION: (29)..(29)
<223> OTHER INFORMATION: Ser, Pro, or Thr
```

```
<220> FEATURE:
<221> NAME/KEY: VARIANT
<222> LOCATION: (31)..(31)
<223> OTHER INFORMATION: Asn, Asp, or Gln
<220> FEATURE:
<221> NAME/KEY: VARIANT
<222> LOCATION: (37)..(37)
<223> OTHER INFORMATION: amino, alkylamino, dialkylamino,
      cycloalkylamino, arylamino, aralkylamino, alkyloxy, aryloxy or
      aralkyloxy

<400> SEQUENCE: 248

Xaa Xaa Asn Thr Ala Thr Xaa Ala Thr Gln Arg Leu Xaa Asn Phe Leu
1               5                   10                  15

Xaa Xaa Xaa Xaa Xaa Asn Xaa Gly Xaa Xaa Leu Xaa Xaa Thr Xaa Val
            20                  25                  30

Gly Ser Asn Thr Tyr
        35

<210> SEQ ID NO 249
<211> LENGTH: 37
<212> TYPE: PRT
<213> ORGANISM: Artificial Sequence
<220> FEATURE:
<223> OTHER INFORMATION: Synthetic construct

<400> SEQUENCE: 249

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 250
<211> LENGTH: 37
<212> TYPE: PRT
<213> ORGANISM: Artificial Sequence
<220> FEATURE:
<223> OTHER INFORMATION: Synthetic construct

<400> SEQUENCE: 250

Lys Cys Asn Thr Ala Thr Cys Ala Thr Gln Arg Leu Ala Asn Phe Leu
1               5                   10                  15

Ile Arg Ser Ser Asn Asn Leu Gly Ala Ile Leu Ser Pro Thr Asn Val
            20                  25                  30

Gly Ser Asn Thr Tyr
        35

<210> SEQ ID NO 251
<211> LENGTH: 37
<212> TYPE: PRT
<213> ORGANISM: Artificial Sequence
<220> FEATURE:
<223> OTHER INFORMATION: Synthetic construct

<400> SEQUENCE: 251

Lys Cys Asn Thr Ala Thr Cys Ala Thr Gln Arg Leu Ala Asn Phe Leu
1               5                   10                  15

Val Arg Thr Ser Asn Asn Leu Gly Ala Ile Leu Ser Pro Thr Asn Val
            20                  25                  30

Gly Ser Asn Thr Tyr
        35
```

<210> SEQ ID NO 252
<211> LENGTH: 37
<212> TYPE: PRT
<213> ORGANISM: Artificial Sequence
<220> FEATURE:
<223> OTHER INFORMATION: Synthetic construct

<400> SEQUENCE: 252

Lys Cys Asn Thr Ala Thr Cys Ala Thr Gln Arg Leu Ala Asn Phe Leu
1               5                   10                  15

Val Arg Ser Ser Asn Asn Leu Gly Pro Val Leu Pro Pro Thr Asn Val
            20                  25                  30

Gly Ser Asn Thr Tyr
        35

<210> SEQ ID NO 253
<211> LENGTH: 37
<212> TYPE: PRT
<213> ORGANISM: Artificial Sequence
<220> FEATURE:
<223> OTHER INFORMATION: Synthetic construct

<400> SEQUENCE: 253

Lys Cys Asn Thr Ala Thr Cys Ala Thr Gln Arg Leu Ala Asn Phe Leu
1               5                   10                  15

Val His Ser Asn Asn Asn Leu Gly Pro Val Leu Ser Pro Thr Asn Val
            20                  25                  30

Gly Ser Asn Thr Tyr
        35

<210> SEQ ID NO 254
<211> LENGTH: 37
<212> TYPE: PRT
<213> ORGANISM: Artificial Sequence
<220> FEATURE:
<223> OTHER INFORMATION: Synthetic construct

<400> SEQUENCE: 254

Lys Cys Asn Thr Ala Thr Cys Ala Thr Gln Arg Leu Thr Asn Phe Leu
1               5                   10                  15

Val Arg Ser Ser His Asn Leu Gly Ala Ala Leu Leu Pro Thr Asp Val
            20                  25                  30

Gly Ser Asn Thr Tyr
        35

<210> SEQ ID NO 255
<211> LENGTH: 36
<212> TYPE: PRT
<213> ORGANISM: Artificial Sequence
<220> FEATURE:
<223> OTHER INFORMATION: Synthetic construct

<400> SEQUENCE: 255

Cys Asn Thr Ala Thr Cys Ala Thr Gln Arg Leu Ala Asn Phe Leu Val
1               5                   10                  15

His Ser Ser Asn Asn Phe Gly Ala Ile Leu Ser Ser Thr Asn Val Gly
            20                  25                  30

Ser Asn Thr Tyr
        35

<210> SEQ ID NO 256
<211> LENGTH: 37
<212> TYPE: PRT
<213> ORGANISM: Artificial Sequence
<220> FEATURE:
<223> OTHER INFORMATION: Synthetic construct

<400> SEQUENCE: 256

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Pro Ser Thr Asn Val
            20                  25                  30

Gly Ser Asn Thr Tyr
        35

<210> SEQ ID NO 257
<211> LENGTH: 37
<212> TYPE: PRT
<213> ORGANISM: Artificial Sequence
<220> FEATURE:
<223> OTHER INFORMATION: Synthetic construct

<400> SEQUENCE: 257

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn Val
            20                  25                  30

Gly Ser Asn Thr Tyr
        35

<210> SEQ ID NO 258
<211> LENGTH: 37
<212> TYPE: PRT
<213> ORGANISM: Artificial Sequence
<220> FEATURE:
<223> OTHER INFORMATION: Synthetic construct

<400> SEQUENCE: 258

Lys Cys Asn Thr Ala Thr Cys Ala Thr Gln Arg Leu Ala Asn Phe Leu
1               5                   10                  15

Val Arg Ser Ser Asn Asn Phe Gly Pro Ile Leu Pro Ser Thr Asn Val
            20                  25                  30

Gly Ser Asn Thr Tyr
        35

<210> SEQ ID NO 259
<211> LENGTH: 36
<212> TYPE: PRT
<213> ORGANISM: Artificial Sequence
<220> FEATURE:
<223> OTHER INFORMATION: Synthetic construct

<400> SEQUENCE: 259

Cys Asn Thr Ala Thr Cys Ala Thr Gln Arg Leu Ala Asn Phe Leu Val
1               5                   10                  15

His Arg Ser Asn Asn Phe Gly Pro Ile Leu Pro Ser Thr Asn Val Gly
            20                  25                  30

Ser Asn Thr Tyr
        35

<210> SEQ ID NO 260
<211> LENGTH: 37
<212> TYPE: PRT
<213> ORGANISM: Artificial Sequence
<220> FEATURE:
<223> OTHER INFORMATION: Synthetic construct

<400> SEQUENCE: 260

```
Lys Cys Asn Thr Ala Thr Cys Ala Thr Gln Arg Leu Ala Asn Phe Leu
1               5                   10                  15

Val His Ser Ser Asn Asn Phe Gly Pro Val Leu Pro Pro Thr Asn Val
            20                  25                  30

Gly Ser Asn Thr Tyr
            35

<210> SEQ ID NO 261
<211> LENGTH: 37
<212> TYPE: PRT
<213> ORGANISM: Artificial Sequence
<220> FEATURE:
<223> OTHER INFORMATION: Synthetic construct

<400> SEQUENCE: 261

Lys Cys Asn Thr Ala Thr Cys Ala Thr Gln Arg Leu Ala Asn Phe Leu
1               5                   10                  15

Val Arg Ser Ser Asn Asn Phe Gly Pro Ile Leu Pro Pro Thr Asn Val
            20                  25                  30

Gly Ser Asn Thr Tyr
            35

<210> SEQ ID NO 262
<211> LENGTH: 36
<212> TYPE: PRT
<213> ORGANISM: Artificial Sequence
<220> FEATURE:
<223> OTHER INFORMATION: Synthetic construct

<400> SEQUENCE: 262

Cys Asn Thr Ala Thr Cys Ala Thr Gln Arg Leu Ala Asn Phe Leu Val
1               5                   10                  15

Arg Ser Ser Asn Asn Phe Gly Pro Ile Leu Pro Pro Ser Asn Val Gly
            20                  25                  30

Ser Asn Thr Tyr
            35

<210> SEQ ID NO 263
<211> LENGTH: 36
<212> TYPE: PRT
<213> ORGANISM: Artificial Sequence
<220> FEATURE:
<223> OTHER INFORMATION: Synthetic construct

<400> SEQUENCE: 263

Cys Asn Thr Ala Thr Cys Ala Thr Gln Arg Leu Ala Asn Phe Leu Val
1               5                   10                  15

His Ser Ser Asn Asn Phe Gly Pro Ile Leu Pro Pro Ser Asn Val Gly
            20                  25                  30

Ser Asn Thr Tyr
            35

<210> SEQ ID NO 264
<211> LENGTH: 37
<212> TYPE: PRT
<213> ORGANISM: Artificial Sequence
<220> FEATURE:
<223> OTHER INFORMATION: Synthetic construct

<400> SEQUENCE: 264

Lys Cys Asn Thr Ala Thr Cys Ala Thr Gln Arg Leu Ala Asn Phe Leu
1               5                   10                  15
```

Val His Ser Ser Asn Asn Leu Gly Pro Val Leu Pro Thr Asn Val
            20                  25                  30

Gly Ser Asn Thr Tyr
        35

<210> SEQ ID NO 265
<211> LENGTH: 37
<212> TYPE: PRT
<213> ORGANISM: Artificial Sequence
<220> FEATURE:
<223> OTHER INFORMATION: Synthetic construct

<400> SEQUENCE: 265

Lys Cys Asn Thr Ala Thr Cys Ala Thr Gln Arg Leu Ala Asn Phe Leu
1               5                   10                  15

Val His Ser Ser Asn Asn Leu Gly Pro Val Leu Pro Ser Thr Asn Val
            20                  25                  30

Gly Ser Asn Thr Tyr
        35

<210> SEQ ID NO 266
<211> LENGTH: 36
<212> TYPE: PRT
<213> ORGANISM: Artificial Sequence
<220> FEATURE:
<223> OTHER INFORMATION: Synthetic construct

<400> SEQUENCE: 266

Cys Asn Thr Ala Thr Cys Ala Thr Gln Arg Leu Ala Asn Phe Leu Val
1               5                   10                  15

His Ser Ser Asn Asn Leu Gly Pro Val Leu Pro Ser Thr Asn Val Gly
            20                  25                  30

Ser Asn Thr Tyr
        35

<210> SEQ ID NO 267
<211> LENGTH: 37
<212> TYPE: PRT
<213> ORGANISM: Artificial Sequence
<220> FEATURE:
<223> OTHER INFORMATION: Synthetic construct

<400> SEQUENCE: 267

Lys Cys Asn Thr Ala Thr Cys Ala Thr Gln Arg Leu Ala Asn Phe Leu
1               5                   10                  15

Val Arg Ser Ser Asn Asn Leu Gly Pro Val Leu Pro Ser Thr Asn Val
            20                  25                  30

Gly Ser Asn Thr Tyr
        35

<210> SEQ ID NO 268
<211> LENGTH: 37
<212> TYPE: PRT
<213> ORGANISM: Artificial Sequence
<220> FEATURE:
<223> OTHER INFORMATION: Synthetic construct

<400> SEQUENCE: 268

Lys Cys Asn Thr Ala Thr Cys Ala Thr Gln Arg Leu Ala Asn Phe Leu
1               5                   10                  15

Val Arg Ser Ser Asn Asn Leu Gly Pro Ile Leu Pro Thr Asn Val
            20                  25                  30

Gly Ser Asn Thr Tyr

-continued

<210> SEQ ID NO 269
<211> LENGTH: 37
<212> TYPE: PRT
<213> ORGANISM: Artificial Sequence
<220> FEATURE:
<223> OTHER INFORMATION: Synthetic construct

<400> SEQUENCE: 269

Lys Cys Asn Thr Ala Thr Cys Ala Thr Gln Arg Leu Ala Asn Phe Leu
1               5                   10                  15

Val Arg Ser Ser Asn Asn Leu Gly Pro Ile Leu Pro Ser Thr Asn Val
            20                  25                  30

Gly Ser Asn Thr Tyr
        35

<210> SEQ ID NO 270
<211> LENGTH: 37
<212> TYPE: PRT
<213> ORGANISM: Artificial Sequence
<220> FEATURE:
<223> OTHER INFORMATION: Synthetic construct

<400> SEQUENCE: 270

Lys Cys Asn Thr Ala Thr Cys Ala Thr Gln Arg Leu Ala Asn Phe Leu
1               5                   10                  15

Ile His Ser Ser Asn Asn Leu Gly Pro Ile Leu Pro Pro Thr Asn Val
            20                  25                  30

Gly Ser Asn Thr Tyr
        35

<210> SEQ ID NO 271
<211> LENGTH: 37
<212> TYPE: PRT
<213> ORGANISM: Artificial Sequence
<220> FEATURE:
<223> OTHER INFORMATION: Synthetic construct

<400> SEQUENCE: 271

Lys Cys Asn Thr Ala Thr Cys Ala Thr Gln Arg Leu Ala Asn Phe Leu
1               5                   10                  15

Val Ile Ser Ser Asn Asn Phe Gly Pro Ile Leu Pro Ser Thr Asn Val
            20                  25                  30

Gly Ser Asn Thr Tyr
        35

<210> SEQ ID NO 272
<211> LENGTH: 36
<212> TYPE: PRT
<213> ORGANISM: Artificial Sequence
<220> FEATURE:
<223> OTHER INFORMATION: Synthetic construct

<400> SEQUENCE: 272

Cys Asn Thr Ala Thr Cys Ala Thr Gln Arg Leu Ala Asn Phe Leu Ile
1               5                   10                  15

His Ser Ser Asn Asn Leu Gly Pro Ile Leu Pro Pro Thr Asn Val Gly
            20                  25                  30

Ser Asn Thr Tyr
        35

<210> SEQ ID NO 273

```
<211> LENGTH: 37
<212> TYPE: PRT
<213> ORGANISM: Artificial Sequence
<220> FEATURE:
<223> OTHER INFORMATION: Synthetic construct

<400> SEQUENCE: 273

Lys Cys Asn Thr Ala Thr Cys Ala Thr Gln Arg Leu Ala Asn Phe Leu
1               5                   10                  15

Ile Arg Ser Ser Asn Asn Leu Gly Ala Ile Leu Ser Ser Thr Asn Val
            20                  25                  30

Gly Ser Asn Thr Tyr
        35

<210> SEQ ID NO 274
<211> LENGTH: 37
<212> TYPE: PRT
<213> ORGANISM: Artificial Sequence
<220> FEATURE:
<223> OTHER INFORMATION: Synthetic construct

<400> SEQUENCE: 274

Lys Cys Asn Thr Ala Thr Cys Ala Thr Gln Arg Leu Ala Asn Phe Leu
1               5                   10                  15

Ile Arg Ser Ser Asn Asn Leu Gly Ala Val Leu Ser Pro Thr Asn Val
            20                  25                  30

Gly Ser Asn Thr Tyr
        35

<210> SEQ ID NO 275
<211> LENGTH: 37
<212> TYPE: PRT
<213> ORGANISM: Artificial Sequence
<220> FEATURE:
<223> OTHER INFORMATION: Synthetic construct

<400> SEQUENCE: 275

Lys Cys Asn Thr Ala Thr Cys Ala Thr Gln Arg Leu Ala Asn Phe Leu
1               5                   10                  15

Ile Arg Ser Ser Asn Asn Leu Gly Pro Val Leu Pro Pro Thr Asn Val
            20                  25                  30

Gly Ser Asn Thr Tyr
        35

<210> SEQ ID NO 276
<211> LENGTH: 37
<212> TYPE: PRT
<213> ORGANISM: Artificial Sequence
<220> FEATURE:
<223> OTHER INFORMATION: Synthetic construct

<400> SEQUENCE: 276

Lys Cys Asn Thr Ala Thr Cys Ala Thr Gln Arg Leu Thr Asn Phe Leu
1               5                   10                  15

Val His Ser Ser His Asn Leu Gly Ala Ala Leu Leu Pro Thr Asp Val
            20                  25                  30

Gly Ser Asn Thr Tyr
        35

<210> SEQ ID NO 277
<211> LENGTH: 37
<212> TYPE: PRT
<213> ORGANISM: Artificial Sequence
<220> FEATURE:
```

<223> OTHER INFORMATION: Synthetic construct

<400> SEQUENCE: 277

Lys Cys Asn Thr Ala Thr Cys Ala Thr Gln Arg Leu Thr Asn Phe Leu
1               5                   10                  15

Val His Ser Ser His Asn Leu Gly Ala Ala Leu Ser Pro Thr Asp Val
            20                  25                  30

Gly Ser Asn Thr Tyr
        35

<210> SEQ ID NO 278
<211> LENGTH: 36
<212> TYPE: PRT
<213> ORGANISM: Artificial Sequence
<220> FEATURE:
<223> OTHER INFORMATION: Synthetic construct

<400> SEQUENCE: 278

Cys Asn Thr Ala Thr Cys Ala Thr Gln Arg Leu Thr Asn Phe Leu Val
1               5                   10                  15

His Ser Ser His Asn Leu Gly Ala Val Leu Pro Ser Thr Asp Val Gly
            20                  25                  30

Ser Asn Thr Tyr
        35

<210> SEQ ID NO 279
<211> LENGTH: 37
<212> TYPE: PRT
<213> ORGANISM: Artificial Sequence
<220> FEATURE:
<223> OTHER INFORMATION: Synthetic construct

<400> SEQUENCE: 279

Lys Cys Asn Thr Ala Thr Cys Ala Thr Gln Arg Leu Thr Asn Phe Leu
1               5                   10                  15

Val Arg Ser Ser His Asn Leu Gly Ala Ala Leu Ser Pro Thr Asp Val
            20                  25                  30

Gly Ser Asn Thr Tyr
        35

<210> SEQ ID NO 280
<211> LENGTH: 37
<212> TYPE: PRT
<213> ORGANISM: Artificial Sequence
<220> FEATURE:
<223> OTHER INFORMATION: Synthetic construct

<400> SEQUENCE: 280

Lys Cys Asn Thr Ala Thr Cys Ala Thr Gln Arg Leu Thr Asn Phe Leu
1               5                   10                  15

Val Arg Ser Ser His Asn Leu Gly Ala Ile Leu Pro Pro Thr Asp Val
            20                  25                  30

Gly Ser Asn Thr Tyr
        35

<210> SEQ ID NO 281
<211> LENGTH: 37
<212> TYPE: PRT
<213> ORGANISM: Artificial Sequence
<220> FEATURE:
<223> OTHER INFORMATION: Synthetic construct

<400> SEQUENCE: 281

```
Lys Cys Asn Thr Ala Thr Cys Ala Thr Gln Arg Leu Thr Asn Phe Leu
1               5                   10                  15

Val Arg Ser Ser His Asn Leu Gly Pro Ala Leu Pro Pro Thr Asp Val
            20                  25                  30

Gly Ser Asn Thr Tyr
        35

<210> SEQ ID NO 282
<211> LENGTH: 37
<212> TYPE: PRT
<213> ORGANISM: Artificial Sequence
<220> FEATURE:
<223> OTHER INFORMATION: Synthetic construct

<400> SEQUENCE: 282

Lys Asp Asn Thr Ala Thr Lys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 283
<211> LENGTH: 37
<212> TYPE: PRT
<213> ORGANISM: Artificial Sequence
<220> FEATURE:
<223> OTHER INFORMATION: Synthetic construct

<400> SEQUENCE: 283

Ala Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 284
<211> LENGTH: 37
<212> TYPE: PRT
<213> ORGANISM: Artificial Sequence
<220> FEATURE:
<223> OTHER INFORMATION: Synthetic construct

<400> SEQUENCE: 284

Ser Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 285
<211> LENGTH: 37
<212> TYPE: PRT
<213> ORGANISM: Artificial Sequence
<220> FEATURE:
<223> OTHER INFORMATION: Synthetic construct

<400> SEQUENCE: 285

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Pro Thr Asn Val
```

```
                20                  25                  30

Gly Ser Asn Thr Tyr
        35

<210> SEQ ID NO 286
<211> LENGTH: 37
<212> TYPE: PRT
<213> ORGANISM: Artificial Sequence
<220> FEATURE:
<223> OTHER INFORMATION: Synthetic construct

<400> SEQUENCE: 286

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Ser Thr Asn Val
                20                  25                  30

Gly Ser Asn Thr Tyr
        35

<210> SEQ ID NO 287
<211> LENGTH: 36
<212> TYPE: PRT
<213> ORGANISM: Artificial Sequence
<220> FEATURE:
<223> OTHER INFORMATION: Synthetic construct

<400> SEQUENCE: 287

Cys Asn Thr Ala Thr Cys Ala Thr Gln Arg Leu Ala Asn Phe Leu Val
1               5                   10                  15

His Ser Ser Asn Asn Phe Gly Pro Ile Leu Pro Ser Thr Asn Val Gly
                20                  25                  30

Ser Asn Thr Tyr
        35

<210> SEQ ID NO 288
<211> LENGTH: 36
<212> TYPE: PRT
<213> ORGANISM: Artificial Sequence
<220> FEATURE:
<223> OTHER INFORMATION: Synthetic construct

<400> SEQUENCE: 288

Cys Asn Thr Ala Thr Cys Ala Thr Gln Arg Leu Ala Asn Phe Leu Val
1               5                   10                  15

His Ser Ser Asn Asn Phe Gly Pro Val Leu Pro Pro Ser Asn Val Gly
                20                  25                  30

Ser Asn Thr Tyr
        35

<210> SEQ ID NO 289
<211> LENGTH: 37
<212> TYPE: PRT
<213> ORGANISM: Artificial Sequence
<220> FEATURE:
<223> OTHER INFORMATION: Synthetic construct

<400> SEQUENCE: 289

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
                20                  25                  30

Gly Ser Asn Thr Tyr
        35
```

```
<210> SEQ ID NO 290
<211> LENGTH: 37
<212> TYPE: PRT
<213> ORGANISM: Artificial Sequence
<220> FEATURE:
<223> OTHER INFORMATION: Synthetic construct

<400> SEQUENCE: 290

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn Val
            20                  25                  30

Gly Ser Asn Thr Tyr
        35

<210> SEQ ID NO 291
<211> LENGTH: 32
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (32)..(32)
<223> OTHER INFORMATION: AMIDATION

<400> SEQUENCE: 291

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 292
<211> LENGTH: 32
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (32)..(32)
<223> OTHER INFORMATION: AMIDATION

<400> SEQUENCE: 292

Cys Ser Asn Leu Ser Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30
```